(12) United States Patent
Lu et al.

(10) Patent No.: US 9,572,879 B2
(45) Date of Patent: Feb. 21, 2017

(54) ROBO2 INHIBITORY COMPOSITIONS COMPRISING SLIT2-BINDING EXTRACELLULAR DOMAIN OF ROBO2

(71) Applicant: BOSTON MEDICAL CENTER CORPORATION, Boston, MA (US)

(72) Inventors: Weining Lu, West Roxbury, MA (US); Xueping Fan, Braintree, MA (US); David J. Salant, Newton, MA (US)

(73) Assignee: Boston Medical Center Corporation, Boston, MA (US)

( * ) Notice: Subject to any disclaimer, the term of this patent is extended or adjusted under 35 U.S.C. 154(b) by 0 days.

(21) Appl. No.: 14/369,094

(22) PCT Filed: Jan. 4, 2013

(86) PCT No.: PCT/US2013/020280
§ 371 (c)(1),
(2) Date: Jun. 26, 2014

(87) PCT Pub. No.: WO2013/103811
PCT Pub. Date: Jul. 11, 2013

(65) Prior Publication Data
US 2015/0037325 A1 Feb. 5, 2015

Related U.S. Application Data

(60) Provisional application No. 61/583,379, filed on Jan. 5, 2012.

(51) Int. Cl.
| | |
|---|---|
| *C07K 14/705* | (2006.01) |
| *A61K 38/17* | (2006.01) |
| *A61K 39/395* | (2006.01) |
| *C12Q 1/68* | (2006.01) |
| *G01N 33/68* | (2006.01) |
| *A61K 45/06* | (2006.01) |
| *A61K 31/7088* | (2006.01) |
| *A61K 31/713* | (2006.01) |
| *C07K 14/47* | (2006.01) |
| *C07K 16/18* | (2006.01) |
| *C12N 15/113* | (2010.01) |
| *C12N 15/115* | (2010.01) |
| *A61P 13/12* | (2006.01) |

(52) U.S. Cl.
CPC ....... *A61K 39/3955* (2013.01); *A61K 31/7088* (2013.01); *A61K 31/713* (2013.01); *A61K 38/177* (2013.01); *A61K 38/1709* (2013.01); *A61K 38/1774* (2013.01); *A61K 45/06* (2013.01); *C07K 14/47* (2013.01); *C07K 14/70503* (2013.01); *C07K 16/18* (2013.01); *C12N 15/113* (2013.01); *C12N 15/115* (2013.01); *C12Q 1/6883* (2013.01); *G01N 33/6893* (2013.01); *C07K 2317/24* (2013.01); *C07K 2319/70* (2013.01); *C12N 2310/11* (2013.01); *C12N 2310/14* (2013.01); *C12N 2310/16* (2013.01); *C12Q 2600/158* (2013.01); *G01N 2333/70503* (2013.01); *G01N 2800/347* (2013.01)

(58) Field of Classification Search
None
See application file for complete search history.

(56) References Cited

U.S. PATENT DOCUMENTS

| | | |
|---|---|---|
| 2005/0059040 A1 | 3/2005 | Goodman et al. |
| 2013/0273049 A1 | 10/2013 | Dol-Gleizes et al. |

FOREIGN PATENT DOCUMENTS

WO 2011/128561 A1 10/2011

OTHER PUBLICATIONS

Lu et al, 2007. The American Journal of Human Genetics. 80: 616-632.*
Zhang et al, 2010. Journal of Chemical Neuroanatomy. 39: 256-261.*
Robo-Fc Product Sheet, R&D Systems, Revised Aug. 2, 2013; 1 page; no author listed.*
Wells (1990) Biochemistry 29(37): 8509-8517.*
Ngo et al (1994) "The Protein Folding Problem and Tertiary Structure Prediction, Chapter 14: Computational Complexity Protein Structure Prediction, and the Levinthal Paradox" pp. 433-440 and 492-495 only.*
Bork (2000) Genome Research 10:398.*
Skolnick et al (2000) Trends in Biotech. 18(1): 34.*
Doerks et al (1998) Trends in Genetics 14(6): 248.*
Brenner (1999) Trends in Genetics 15(4): 132.*
Liu et al, 2004 (Mol Cell Neurosci. 26: 232-240).*
Fan et al. "Robo2 is a Podocyte Protein Required for Normal Glomerular Filtration Barrier Function." ASN Renal Week 2009, free communication. San Diego: American Society of Nephrology. Retrieved on Apr. 3, 2012. Retrieved from the internet <URL: sitemason.vanderbilt.edu/files/jZZLgs/Free%20Communication.pdf> Abstract F-FC272, p. 64A.
Lindenmeyer et al. "Systematic analysis of a novel human renal glomerulus-enriched gene expression dataset." PLoS One. Jul. 12, 2010, vol. 5, No. 7, article e 11545, pp. 1-12.
Schlondorff. "Nephrin AKTs on actin: The slit diaphragm-actin cytoskeleton signaling network expands." Kidney Int. Mar. 2008, vol. 73, No. 5, pp. 524-525.
Lu et al. "Disruption of ROBO2 is associated with urinary tract anomalies and confers risk of vesicoureteral reflux." Am. J. of Hum. Genet. Apr. 2007, vol. 80, No. 4, pp. 616-632.
Grieshammer et al. "SLIT2-mediated ROBO2 signaling restricts kidney induction to a single site." Dev. Cell. May 2004, vol. 6, No. 5, pp. 709-717.

(Continued)

*Primary Examiner* — Zachary Howard
(74) *Attorney, Agent, or Firm* — Nixon Peabody LLP; Ronald I. Eisenstein; Susanna C. Benn

(57) ABSTRACT

Provided herein are methods for the treatment of chronic kidney disease and proteinuria and for the diagnosis of chronic kidney disease and monitoring the effects of treatment on the progression of chronic kidney disease and proteinuria based on unexpected roles for the SLIT-ROBO signaling pathway in the regulation of podocyte F-actin cytoskeleton and foot process structure in the kidney.

11 Claims, 19 Drawing Sheets

(56) References Cited

OTHER PUBLICATIONS

Bertoli-Avella et al. "ROBO2 gene variants are associated with familial vesicoureteral reflux." J. Am. Soc. Nephrol. Apr. 2008, vol. 19, No. 4, pp. 825-831.
Fan et al. "Inhibitory effects of Robo2 on nephrin: a crosstalk between positive and negative signals regulating podocyte structure." Cell Rep. Jul. 26, 2012, vol. 2, No. 1, pp. 52-61.
Han et al. "Over-expression of Slit2 induces vessel formation and changes blood vessel permeability in mouse brain." Acta Pharm. Sinica: 2011, vol. 32, p. 1327-1336.
Kanellis et al. "Modulation of Inflammation by Slit Protein in Vivo in Experimental Crescentic Glomerulonephritis." Am. J. Pathol., Jul. 2004, vol. 165, No. 1, p. 341-352.
Zhou et al. "The role of SLIT-ROBO signaling in proliferation diabetic retinopathy and retinal pigment epithelial cells." Mol. Vision, Jun. 8, 2011, vol. 17, pp. 1526-1536.
Bashaw et al., "Repulsive axon guidance: Abelson and Enabled play opposing roles downstream of the roundabout receptor", Cell , 101:703-715 (2000).
Dickinson et al., "The SLIT/ROBO pathway: a regulatory of cell function woth implication for the reproductive system", Reproduction, 139(4):697-704 (2010).
Dickson et al., "Regulation of commissural axon pathfinding by slit and its Robo receptors", Annu Rev Cell Dev Biol 22, 651-675 (2006).
Guan et al., "Signaling mechanisms mediating neuronal responses to guidance cues", Nat Rev Neurosci 4, 941-956 (2003).
Hivert et al. "Robot and Robo2 are homophilic binding molecules that promote axonal growth", Mol Cell Neurosci. Dec;21(4):534-545 (2002).
Piper et al., "Signaling mechanisms underlying slit2-induced collapse of xenopus retinal growth cones", Neuron, 49(2):215-228 (2006).
Fan et al., "Robo2 is a podocyte protein required for normal glomerular filtration barrier function", J. Am. Soc. Nephrol. 20: p. 64A, abstract No. F-FC272 (2009).
Halaby et al. Protein Eng. (1999) 12 (7): pp. 563-571.
Ferrari, P., "Prescribing angiotensin-converting enzyme inhibitors and angiotensin receptor blockers in chronic kidney disease", Nephrology, 12(1): 81-89 (2007).
Kidd et al., "Roundabout Controls Axon Crossing of the CNS Midline and Defines a Novel Subfamily of Evolutionarily Conserved Guidance Receptors", Cell, 92(2): 205-215 (1998).
Shiau et al., "Robo2-Slit1 dependent cell-cell interactions mediate assembly of the trigeminal ganglion", Nature Neuroscience, 11(3): 269-276 (2008).
Small et al., "MicroRNA0218 regulates vascular patterning by modulation of Slit-Robo signaling", Circulation Research, 107(11): 1336-1344 (2010).
Dickinson et al., "Novel Regulated Expression of the SLIT/ROBO Pathway in the Ovary: Possible Role during Luteolysis in Women", Endocrinology 149(10): 5024-5034 (2008).
Hocking et al., "Distinct roles for ROBO2 in the regulation of axon and dendrite growth by retinal ganglion cells" Mechanisms of Development 127: 36-48 (2010).
Japanese Notice of Reasons of Rejection received in JP application No. 2014-551337, Mailed Sep. 14, 2016. 10pp.

* cited by examiner

TELEHYAVEQQENGYOSDSWCPPLPVQTYLHQGLEDELEEDDDRVPTPPVRGVASSPA
ISFGQQSTATLTPSPREEMQPMLQAHLDELTRAYQFDIAKQTWHIQSNNQPPQPPVPPL
GYVSGALISDLETDVADDDADDEEEALEIPRPLRALDQTPGSSMDNLDSSVTGKAFTSS
QRPRPTSPFSTDSNTSAALSQSQRPRPTKHKGGRMDQQPA

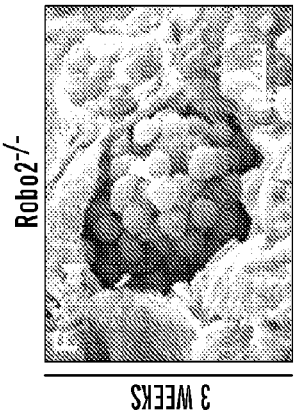
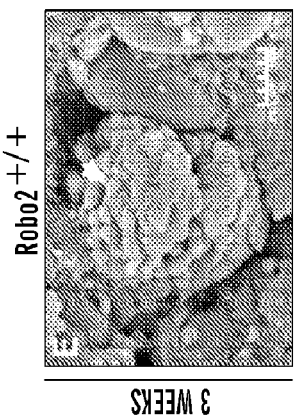
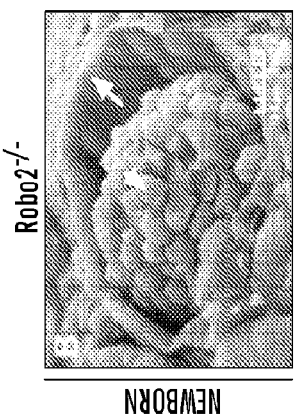
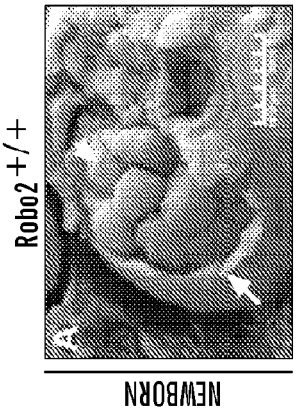
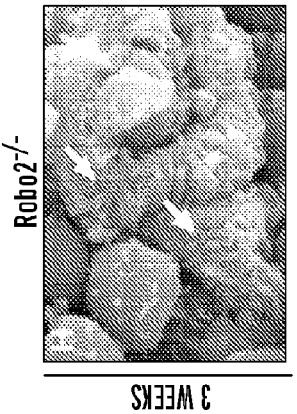
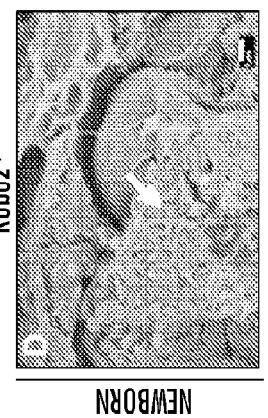
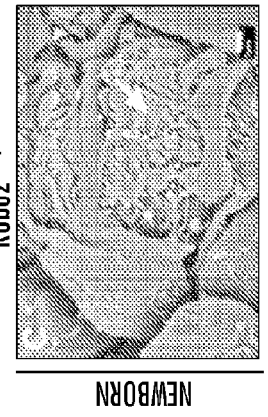
FIG. 4A  FIG. 4B  FIG. 4C  FIG. 4D
FIG. 4E  FIG. 4F  FIG. 4G  FIG. 4H

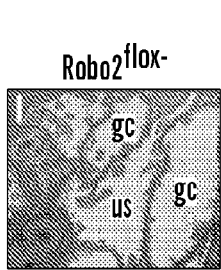
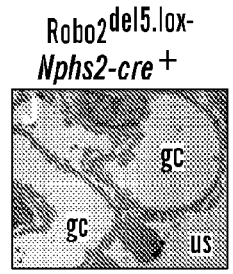
FIG. 4I   FIG. 4J
FIG. 4K   FIG. 4L
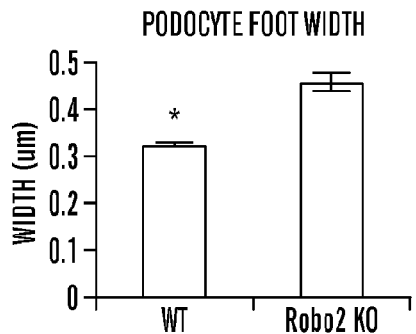
FIG. 4M
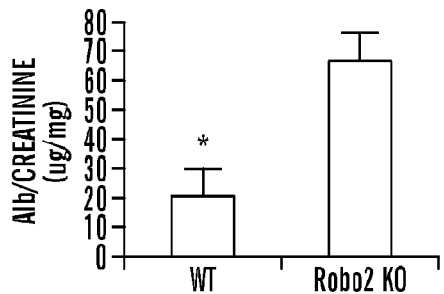
FIG. 4N
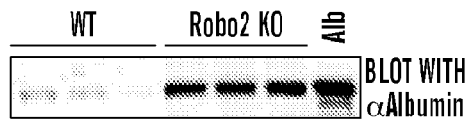
FIG. 4O Robo2+/-; Nphs1-/-

Robo2+/-; Nphs1-/-

Robo2-/-; Nphs1+/-

Robo2-/-; Nphs1+/-

Robo2-/-; Nphs1-/-

Robo2-/-; Nphs1-/-

Robo2+/+; Nphs1+/+

Robo2+/+; Nphs1+/+

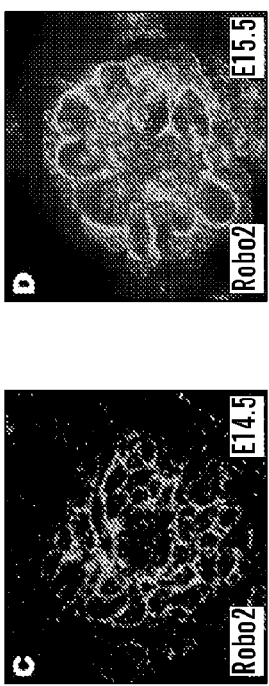

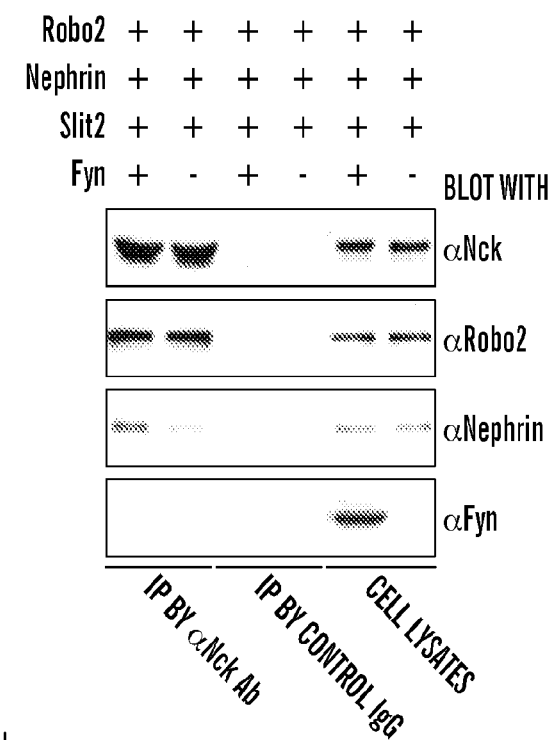
FIG. 6A
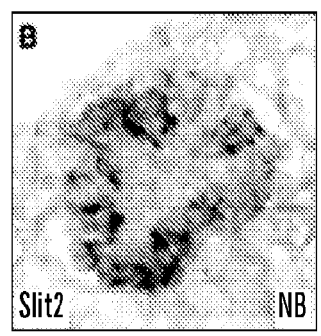   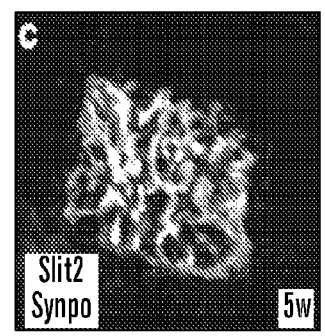
FIG. 6B   FIG. 6C

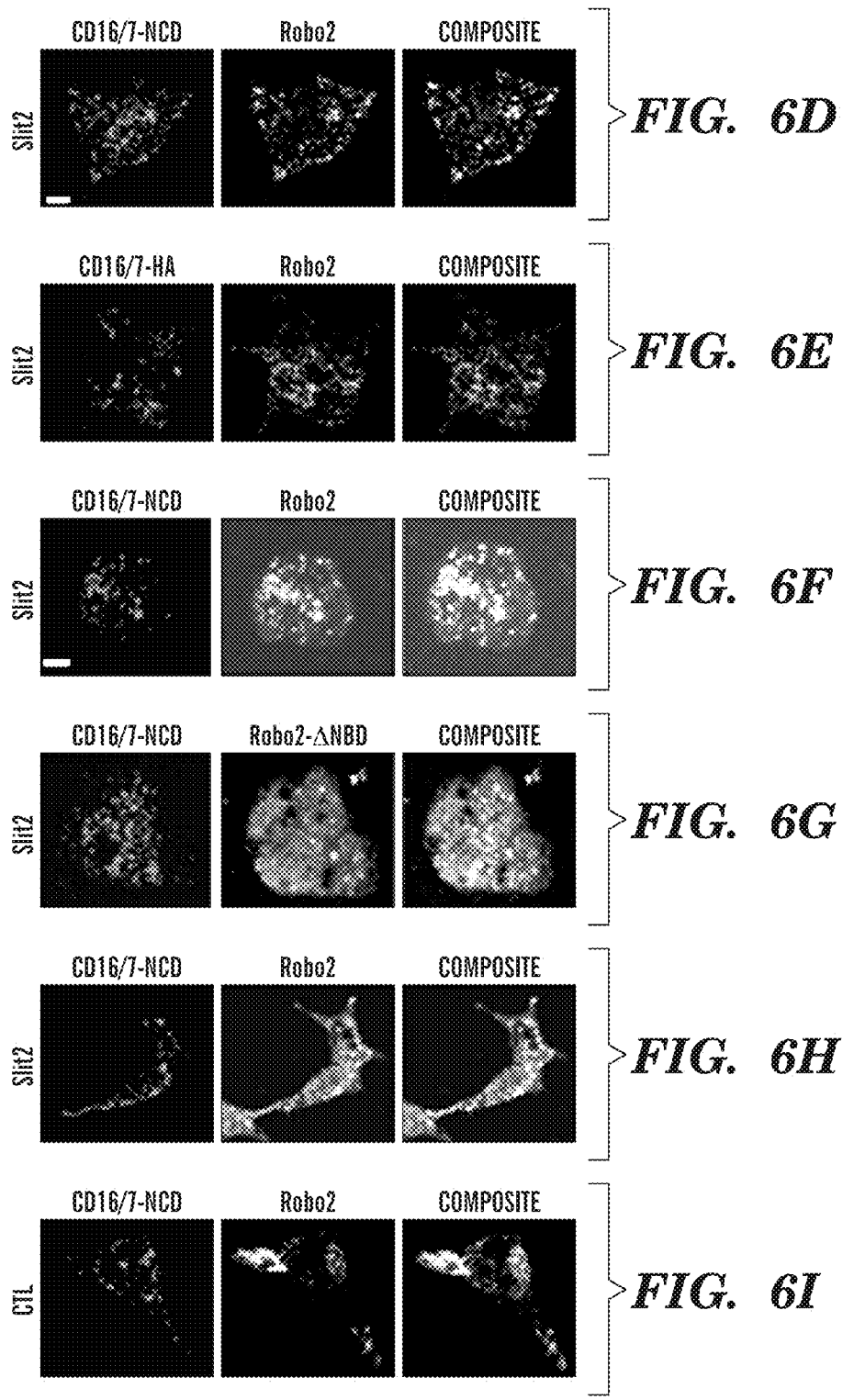

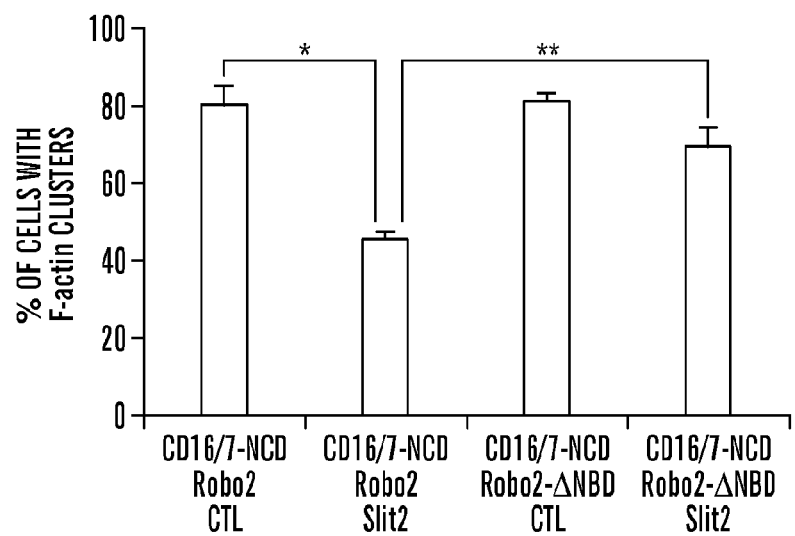
FIG. 7C
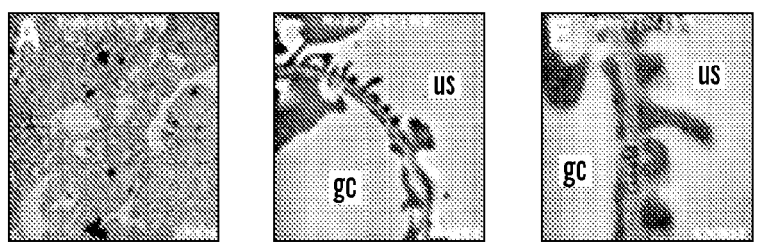
FIG. 8A　FIG. 8C　FIG. 8E
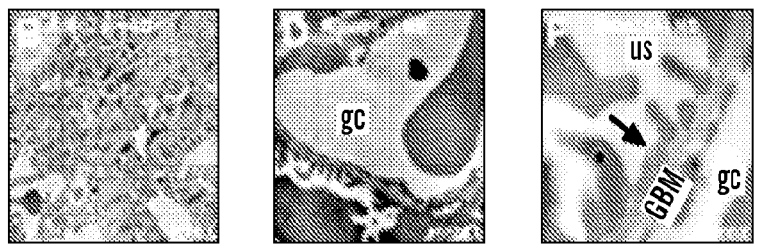
FIG. 8B　FIG. 8D　FIG. 8F

SEQUENCE LISTING

```
<160> NUMBER OF SEQ ID NOS: 6

<210> SEQ ID NO 1
<211> LENGTH: 1394
<212> TYPE: PRT
<213> ORGANISM: Homo sapiens

<400> SEQUENCE: 1

Met Ala Arg Arg His Glu Arg Val Thr Arg Arg Met Trp Thr Trp Ala
1               5                   10                  15

Pro Gly Leu Leu Met Met Thr Val Val Phe Trp Gly His Gln Gly Asn
            20                  25                  30

Gly Gln Gly Gln Gly Ser Arg Leu Arg Gln Glu Asp Phe Pro Pro Arg
        35                  40                  45

Ile Val Glu His Pro Ser Asp Val Ile Val Ser Lys Gly Glu Pro Thr
    50                  55                  60

Thr Leu Asn Cys Lys Ala Glu Gly Arg Pro Thr Pro Thr Ile Glu Trp
65                  70                  75                  80

Tyr Lys Asp Gly Glu Arg Val Glu Thr Asp Lys Asp Asp Pro Arg Ser
                85                  90                  95

His Arg Met Leu Leu Pro Ser Gly Ser Leu Phe Phe Leu Arg Ile Val
            100                 105                 110

His Gly Arg Arg Ser Lys Pro Asp Glu Gly Ser Tyr Val Cys Val Ala
        115                 120                 125

Arg Asn Tyr Leu Gly Glu Ala Val Ser Arg Asn Ala Ser Leu Glu Val
    130                 135                 140

Ala Leu Leu Arg Asp Asp Phe Arg Gln Asn Pro Thr Asp Val Val Val
145                 150                 155                 160

Ala Ala Gly Glu Pro Ala Ile Leu Glu Cys Gln Pro Pro Arg Gly His
                165                 170                 175

Pro Glu Pro Thr Ile Tyr Trp Lys Lys Asp Lys Val Arg Ile Asp Asp
            180                 185                 190

Lys Glu Glu Arg Ile Ser Ile Arg Gly Gly Lys Leu Met Ile Ser Asn
        195                 200                 205

Thr Arg Lys Ser Asp Ala Gly Met Tyr Thr Cys Val Gly Thr Asn Met
    210                 215                 220

Val Gly Glu Arg Asp Ser Asp Pro Ala Glu Leu Thr Val Phe Glu Arg
225                 230                 235                 240

Pro Thr Phe Leu Arg Arg Pro Ile Asn Gln Val Val Leu Glu Glu Glu
                245                 250                 255

Ala Val Glu Phe Arg Cys Gln Val Gln Gly Asp Pro Gln Pro Thr Val
            260                 265                 270

Arg Trp Lys Lys Asp Asp Ala Asp Leu Pro Arg Gly Arg Tyr Asp Ile
```

```
            275                 280                 285
Lys Asp Asp Tyr Thr Leu Arg Ile Lys Lys Thr Met Ser Thr Asp Glu
290                 295                 300

Gly Thr Tyr Met Cys Ile Ala Glu Asn Arg Val Gly Lys Met Glu Ala
305                 310                 315                 320

Ser Ala Thr Leu Thr Val Arg Ala Pro Pro Gln Phe Val Val Arg Pro
                325                 330                 335

Arg Asp Gln Ile Val Ala Gln Gly Arg Thr Val Thr Phe Pro Cys Glu
                340                 345                 350

Thr Lys Gly Asn Pro Gln Pro Ala Val Phe Trp Gln Lys Glu Gly Ser
            355                 360                 365

Gln Asn Leu Leu Phe Pro Asn Gln Pro Gln Pro Asn Ser Arg Cys
370                 375                 380

Ser Val Ser Pro Thr Gly Asp Leu Thr Ile Thr Asn Ile Gln Arg Ser
385                 390                 395                 400

Asp Ala Gly Tyr Tyr Ile Cys Gln Ala Leu Thr Val Ala Gly Ser Ile
                405                 410                 415

Leu Ala Lys Ala Gln Leu Glu Val Thr Asp Val Leu Thr Asp Arg Pro
                420                 425                 430

Pro Pro Ile Ile Leu Gln Gly Pro Ala Asn Gln Thr Leu Ala Val Asp
            435                 440                 445

Gly Thr Ala Leu Leu Lys Cys Lys Ala Thr Gly Asp Pro Leu Pro Val
450                 455                 460

Ile Ser Trp Leu Lys Glu Gly Phe Thr Phe Pro Gly Arg Asp Pro Arg
465                 470                 475                 480

Ala Thr Ile Gln Glu Gln Gly Thr Leu Gln Ile Lys Asn Leu Arg Ile
                485                 490                 495

Ser Asp Thr Gly Thr Tyr Thr Cys Val Ala Thr Ser Ser Gly Glu
                500                 505                 510

Thr Ser Trp Ser Ala Val Leu Asp Val Thr Glu Ser Gly Ala Thr Ile
            515                 520                 525

Ser Lys Asn Tyr Asp Leu Ser Asp Leu Pro Gly Pro Pro Ser Lys Pro
530                 535                 540

Gln Val Thr Asp Val Thr Lys Asn Ser Val Thr Leu Ser Trp Gln Pro
545                 550                 555                 560

Gly Thr Pro Gly Thr Leu Pro Ala Ser Ala Tyr Ile Ile Glu Ala Phe
                565                 570                 575

Ser Gln Ser Val Ser Asn Ser Trp Gln Thr Val Ala Asn His Val Lys
                580                 585                 590

Thr Thr Leu Tyr Thr Val Arg Gly Leu Arg Pro Asn Thr Ile Tyr Leu
            595                 600                 605

Phe Met Val Arg Ala Ile Asn Pro Gln Gly Leu Ser Asp Pro Ser Pro
610                 615                 620

Met Ser Asp Pro Val Arg Thr Gln Asp Ile Ser Pro Pro Ala Gln Gly
625                 630                 635                 640

Val Asp His Arg Gln Val Gln Lys Glu Leu Gly Asp Val Leu Val Arg
                645                 650                 655

Leu His Asn Pro Val Val Leu Thr Pro Thr Thr Val Gln Val Thr Trp
                660                 665                 670

Thr Val Asp Arg Gln Pro Gln Phe Ile Gln Gly Tyr Arg Val Met Tyr
            675                 680                 685

Arg Gln Thr Ser Gly Leu Gln Ala Thr Ser Ser Trp Gln Asn Leu Asp
690                 695                 700
```

-continued

Ala Lys Val Pro Thr Glu Arg Ser Ala Val Leu Val Asn Leu Lys Lys
705                 710                 715                 720

Gly Val Thr Tyr Glu Ile Lys Val Arg Pro Tyr Phe Asn Glu Phe Gln
            725                 730                 735

Gly Met Asp Ser Glu Ser Lys Thr Val Arg Thr Thr Glu Glu Ala Pro
                740                 745                 750

Ser Ala Pro Pro Gln Ser Val Thr Val Leu Thr Val Gly Ser Tyr Asn
            755                 760                 765

Ser Thr Ser Ile Ser Val Ser Trp Asp Pro Pro Pro Asp His Gln
    770                 775                 780

Asn Gly Ile Ile Gln Glu Tyr Lys Ile Trp Cys Leu Gly Asn Glu Thr
785                 790                 795                 800

Arg Phe His Ile Asn Lys Thr Val Asp Ala Ala Ile Arg Ser Val Ile
                805                 810                 815

Ile Gly Gly Leu Phe Pro Gly Ile Gln Tyr Arg Val Glu Val Ala Ala
            820                 825                 830

Ser Thr Ser Ala Gly Val Gly Val Lys Ser Glu Pro Gln Pro Ile Ile
            835                 840                 845

Ile Gly Arg Arg Asn Glu Val Val Ile Thr Glu Asn Asn Asn Ser Ile
    850                 855                 860

Thr Glu Gln Ile Thr Asp Val Val Lys Gln Pro Ala Phe Ile Ala Gly
865                 870                 875                 880

Ile Gly Gly Ala Cys Trp Val Ile Leu Met Gly Phe Ser Ile Trp Leu
                885                 890                 895

Tyr Trp Arg Arg Lys Lys Arg Lys Gly Leu Ser Asn Tyr Ala Val Thr
            900                 905                 910

Phe Gln Arg Gly Asp Gly Gly Leu Met Ser Asn Gly Ser Arg Pro Gly
        915                 920                 925

Leu Leu Asn Ala Gly Asp Pro Ser Tyr Pro Trp Leu Ala Asp Ser Trp
    930                 935                 940

Pro Ala Thr Ser Leu Pro Val Asn Asn Ser Asn Ser Gly Pro Asn Glu
945                 950                 955                 960

Ile Gly Asn Phe Gly Arg Gly Asp Val Leu Pro Pro Val Pro Gly Gln
                965                 970                 975

Gly Asp Lys Thr Ala Thr Met Leu Ser Asp Gly Ala Ile Tyr Ser Ser
            980                 985                 990

Ile Asp Phe Thr Thr Lys Thr Ser  Tyr Asn Ser Ser Ser  Gln Ile Thr
                995                 1000                1005

Gln Ala  Thr Pro Tyr Ala Thr  Thr Gln Ile Leu His  Ser Asn Ser
    1010                1015                    1020

Ile His  Glu Leu Ala Val Asp  Leu Pro Asp Pro Gln  Trp Lys Ser
    1025                1030                    1035

Ser Ile  Gln Gln Lys Thr Asp  Leu Met Gly Phe Gly  Tyr Ser Leu
    1040                1045                    1050

Pro Asp  Gln Asn Lys Gly Asn  Asn Gly Gly Lys Gly  Gly Lys Lys
    1055                1060                    1065

Lys Lys  Asn Lys Asn Ser Ser  Lys Pro Gln Lys Asn  Asn Gly Ser
    1070                1075                    1080

Thr Trp  Ala Asn Val Pro Leu  Pro Pro Pro Pro Val  Gln Pro Leu
    1085                1090                    1095

Pro Gly  Thr Glu Leu Glu His  Tyr Ala Val Glu Gln  Gln Glu Asn
    1100                1105                    1110

| | | | | | | | | | | | |
|---|---|---|---|---|---|---|---|---|---|---|---|
| Gly | Tyr | Asp | Ser | Asp | Ser | Trp | Cys | Pro | Pro | Leu | Pro | Val | Gln | Thr |

Gly Tyr Asp Ser Asp Ser Trp Cys Pro Pro Leu Pro Val Gln Thr
1115                1120               1125

Tyr Leu His Gln Gly Leu Glu Asp Glu Leu Glu Asp Asp Asp
1130                1135               1140

Arg Val Pro Thr Pro Pro Val Arg Gly Val Ala Ser Ser Pro Ala
1145                1150               1155

Ile Ser Phe Gly Gln Gln Ser Thr Ala Thr Leu Thr Pro Ser Pro
1160                1165               1170

Arg Glu Glu Met Gln Pro Met Leu Gln Ala His Leu Asp Glu Leu
1175                1180               1185

Thr Arg Ala Tyr Gln Phe Asp Ile Ala Lys Gln Thr Trp His Ile
1190                1195               1200

Gln Ser Asn Asn Gln Pro Pro Gln Pro Pro Val Pro Pro Leu Gly
1205                1210               1215

Tyr Val Ser Gly Ala Leu Ile Ser Asp Leu Glu Thr Asp Val Ala
1220                1225               1230

Asp Asp Asp Ala Asp Asp Glu Glu Ala Leu Glu Ile Pro Arg
1235                1240               1245

Pro Leu Arg Ala Leu Asp Gln Thr Pro Gly Ser Ser Met Asp Asn
1250                1255               1260

Leu Asp Ser Ser Val Thr Gly Lys Ala Phe Thr Ser Ser Gln Arg
1265                1270               1275

Pro Arg Pro Thr Ser Pro Phe Ser Thr Asp Ser Asn Thr Ser Ala
1280                1285               1290

Ala Leu Ser Gln Ser Gln Arg Pro Arg Pro Thr Lys Lys His Lys
1295                1300               1305

Gly Gly Arg Met Asp Gln Gln Pro Ala Leu Pro His Arg Arg Glu
1310                1315               1320

Gly Met Thr Asp Glu Glu Ala Leu Val Pro Tyr Ser Lys Pro Ser
1325                1330               1335

Phe Pro Ser Pro Gly Gly His Ser Ser Ser Gly Thr Ala Ser Ser
1340                1345               1350

Lys Gly Ser Thr Gly Pro Arg Lys Thr Glu Val Leu Arg Ala Gly
1355                1360               1365

His Gln Arg Asn Ala Ser Asp Leu Leu Asp Ile Gly Tyr Met Gly
1370                1375               1380

Ser Asn Ser Gln Gly Gln Phe Thr Gly Glu Leu
1385                1390

```
<210> SEQ ID NO 2
<211> LENGTH: 8374
<212> TYPE: DNA
<213> ORGANISM: Homo sapiens

<400> SEQUENCE: 2
gcgctggagg agggaggcgg aaggacagcg ctgcgccacc acccggagga gggagcgcgg      60
tagctgcagg caggggaggg agaggaaaga aaaggaagga cggctcccag acagagagtg    120
ggagaaaccg gggagcagcg ggagcagcag gtccgggggg agctgttccg ctgcgctgcc    180
ctcgttattc acacggacgc tgcggagctt cccaggctg cttccctgtc ccctggggtg     240
gaggctgccg tctaaacctg actccagagt ttaagatgca atggccagaa gacatgaacg    300
tgtcactaga aggatgtgga catgggctcc gggactgttg atgatgactg tggtgttttg    360
gggtcatcag gggaatggac aaggccaagg atcgcgtctt cgccaggagg actttccccc    420
```

```
gcggattgtg gagcatcctt ccgatgtcat cgtctctaag ggcgagccca cgactctgaa    480
ctgcaaggcg gagggccggc caacgcccac cattgagtgg tacaaagatg gggagcgagt    540
ggagactgac aaggacgatc cccggtccca caggatgctt ctgcccagcg atccttatt     600 cttcttgcgc atcgtgcacg ggcgcaggag taaacctgat gaaggaagct acgtttgtgt    660
tgcgaggaac tatcttggtg aagcagtgag tcgaaatgcg tctctggaag tggcattgtt    720
acgagatgac ttccgacaaa accccacaga tgttgtagtg gcagctggag agcctgcaat    780
cctggagtgc cagcctcccc ggggacaccc agaacccacc atctactgga aaaagacaa     840 agttcgaatt gatgacaagg aagaaagaat aagtatccgt ggtggaaaac tgatgatctc    900
caataccagg aaaagtgatg cagggatgta acttgtgtt ggtaccaata tggtgggaga     960
aagggacagt gacccagcag agctgactgt ctttgaacga cccacatttc tcaggaggcc   1020
aattaaccag gtggtactgg aggaagaagc tgtagaattt cgttgtcaag tccaaggaga   1080
tcctcaacca actgtgaggt ggaaaaagga tgatgcagac ttgccaagag aaggtatga    1140 catcaaagac gattacacac taagaattaa aaagaccatg agtacagatg aaggcaccta   1200
tatgtgtatt gctgagaatc gggttggaaa aatggaagcc tctgctacac tcaccgtccg   1260
agctccccca cagtttgtgg ttcggccaag agatcagatt gttgctcaag gtcgaacagt   1320
gacatttccc tgtgaaacta aaggaaaccc acagccagct gttttttggc agaaagaagg   1380
cagccagaac ctacttttcc caaaccaacc ccagcagccc aacagtagat gctcagtgtc   1440
accaactgga gacctcacaa tcaccaacat tcaacgttcc gacgcgggtt actacatctg   1500
ccaggcttta actgtggcag gaagcatttt agcaaaagct caactggagg ttactgatgt   1560
tttgacagat agacctccac ctataattct acaaggccca gccaaccaaa cgctggcagt   1620
ggatggtaca gcgttactga atgtaaagc cactggtgat cctcttcctg taattagctg    1680
gttaaaggag ggatttactt ttccgggtag agatccaaga gcaacaattc aagagcaagg   1740
cacactgcag attaagaatt tacggatttc tgatactggc acttatactt gtgtggctac   1800
aagttcaagt ggagagactt cctggagtgc agtgctggat gtgacagagt ctggagcaac   1860
aatcagtaaa aactatgatt taagtgacct gccagggcca ccatccaaac cgcaggtcac   1920
tgatgttact aagaacagtg tcaccttgtc ctggcagcca ggtacccctg gaacccttcc   1980
agcaagtgca tatatcattg aggctttcag ccaatcagtg agcaacagct ggcagaccgt   2040
ggcaaaccat gtaaagacca ccctctatac tgtaagagga ctgcggccca atacaatcta   2100
cttattcatg gtcagagcga tcaacccca  aggtctcagt gacccaagtc ccatgtcaga   2160
tcctgtgcgc acacaagata tcagcccacc agcacaagga gtggaccaca ggcaagtgca   2220
gaaagagcta ggagatgtcc ttgtccgtct tcataatcca gttgtgctga ctcccaccac   2280
ggttcaggtc acatggacgg ttgatcgcca accccagttt atccaaggct accgagtgat   2340
gtatcgtcag acttcaggtc tgcaggcgac atcttcgtgg cagaatttag atgccaaagt   2400
cccgactgaa cgaagtgctg tcttagtcaa cctgaaaaag gggtgacttt atgaaattaa   2460
agtacggcca tattttaatg agttccaagg aatggatagt gaatctaaaa cggttcgtac   2520
tactgaagaa gccccaagtg ccccaccaca gtctgtcact gtactgacag ttggaagcta   2580
caatagcaca agtattagtg tttcctggga tcctcctcct ccagatcacc agaatggaat   2640
tatccaagaa tacaagatct ggtgtctagg aaatgaaacg cgattccata tcaacaaaac   2700
tgtggatgca gccattcggt ccgtaataat tggtggatta ttcccaggta ttcaataccg   2760
ggtagaggtt gcagctagta ccagtgcagg ggttggagta aagagtgagc cacagccaat   2820
```

```
aataatcggg agacgcaatg aagttgtcat tactgaaaac aataacagca taactgagca    2880
aatcactgat gtggtgaagc aaccagcctt tatagctggt attggtggtg cctgctgggt    2940
aattctgatg ggttttagca tatggttgta ttggcgaaga agaagagga agggactcag     3000 taattatgct gttacgtttc aaagaggaga tggaggacta atgagcaatg gaagccgtcc    3060
aggtcttctc aatgctggtg atcccagcta ccatggctt gctgattctt ggccagccac     3120
gagcttgcca gtaaataata gcaacagtgg cccaaatgag attggaaatt ttggccgtgg    3180
agatgtgctg ccaccagttc caggccaagg ggataaaaca gcaacgatgc tctcagatgg    3240
agccatttat agtagcattg acttcactac caaaaccagt tacaacagtt ccagccaaat    3300
aacacaggct accccatatg ccacgacaca gatcttgcat ccaacagca tacatgaatt     3360 ggctgtcgat ctgcctgatc cacaatggaa aagctcaatt cagcaaaaaa cagatctgat    3420
gggatttggt tattctctac ctgatcagaa caaaggtaac aatggtggga aggtggaaa     3480 aaagaagaaa aataaaaact cttctaaacc acagaaaaac aatggatcca cttgggccaa    3540
tgtccctcta cctccccccc cagtccagcc ccttcctggc acggagctgg aacactatgc    3600
agtggaacaa caagaaaatg ctatgacag tgatagctgg tgcccaccat tgccagtaca     3660
aacttactta caccaaggtc tggaagatga actggaagaa gatgatgata gggtcccaac    3720
acctcctgtt cgaggcgtgg cttcttctcc tgctatctcc tttggacagc agtccactgc    3780
aactcttact ccatccccac gggaagagat gcaacccatg ctgcaggctc acctggatga    3840
gttgacaaga gcctatcagt ttgatatagc aaaacaaaca tggcacattc aaagcaataa    3900
tcaacctcca cagcctccag ttccaccgtt aggttatgtg tctggagcct tgatttctga    3960
tttgaaaacg gatgttgcag atgatgatgc cgacgacgaa gaggaagctt tagaaatccc    4020
caggcccctg agagcactgg accagactcc tggatccagc atggacaatc tagacagctc    4080
tgtgacagga aaagccttta cctcctctca aagacctcga cctaccagcc cattttctac    4140
tgacagtaac accagtgcag ccctgagtca aagtcagagg cctcggccca ctaaaaaaca    4200
caagggaggg cggatggacc aacaaccagc attgcctcat cgaagggaag gaatgacaga    4260
tgaggaggcc ttggtgccct atagcaagcc cagtttccca tctccaggtg ccacagctc     4320 atcaggaaca gcttcttcta agggatccac tggacctagg aaaaccgagg tgttgagagc    4380
aggccaccag cgcaatgcca gcgaccttct tgacatagga tatatgggct ccaacagtca    4440
aggacagttt acaggtgaat tatagtaaat gagaggagac atacaaagct gctctgaagg    4500
accatcaggt ccggactcat ggaagtgatg actctaaaca gtgcaatgaa caatttattt    4560
atgtactatt aaaagaactg taaatgcaat gtaaagacac acagccacac atatcccaca    4620
gatattttca ttgtgttctt ctcttaagta caccacccac cttaactctt tcttgtcagg    4680
agtatataaa aagaaagaa aacaaaactc gccctacagg aagaaaagga ttctcctctg     4740
tatataattt cttttgtgca ttgctatgca agctcactct ttttagctct gctcatatta    4800
ttgtctgttc ttattggtct gttgtactat atgtgaatta ataggctgtg gtgccatata    4860
ttaaccttta attgtgtaac ttttatgttt aaattttgca ctgcaatttt atttggtgat    4920
aagcacaaat ctctactcct catgacatga agaaaaagac tgaatgtgaa gggagttttct   4980 gtactgtaag ctagattgga taatgatggc tgtaacaaat catgttagat ggttttcagt    5040
tggggtgtag aaataggaag atgcaaagga acaatggtgt tggcaaagtc ttctttgaat    5100
atcagggact gagtcaataa aaaaaatagt agaaaggtgg cttttactat tgacaaaagc    5160
```

```
cggggtcaaa aaaagtagtt taagtcttaa gactgaatat gcattaaagt atgcaggtag    5220
caaagatgta ataaatttgc ttaaaaaaag aaattaaagt tttatttaga atcaattta    5280 cctgtcattg taattgaccc atctgagaat tacaataagc aagaggaaat taaggtgttt    5340
tgcaagagct gtatttatat tacagttttt taaaaacatt ttctgaatta tcgtaattaa    5400
gctctccaac tcgttaagtc agaatataat atgaagttcc ccaaggaaac gaacaaaatg    5460
aactctagaa tatctagcaa atagttaaag aagcaattta ttattagggc atactcgggc    5520
tgtttccaaa tataaactct attgcaatat cttatttcat cttcctaata catgtacagt    5580
gcacactaga ggatagagct gcatcactta aattcatgac ttaaaaaata atacagttta    5640
tatacaactt gtttttat tgattaagaa gtgaagttta cgccacccaa tgtatagcca    5700
aattgtacgt gcttaaaaaa cagtgccgag agtatgttca gttcgcagta agtagattta    5760
ttggaataaa tattctatgg tacattctca gaaattggct tccaactaaa atacgtttga    5820 cccatttga ataaggaaat tgaaaagaaa aatttaaaag gagaaaaaaa tgcatgttta    5880 taaactttt aaataaaacc agaccttgta agtggacatt aataattgtc ctgcctcatt    5940
tgttttcacg actttgacaa caagaagttc ctgaacatta gtcatgtatg ctcagaataa    6000
atgtgacttt gaaatatatg ttagctactg tacatgtata gtcagtcaag tagaagagga    6060
ccttcctgaa attcccactt gtgacatttt cccatgggtt tcctacacaa tcttaaattt    6120
tatttctgtc tatactttct caaatttttc ctatgataag ttcagttgtt ggtactcttc    6180 taaaatatt caacgtgatt aggatcagtt ctaaaatacg ggaccccttt gagtgacaat    6240
tcgcactcca tgcattattg gctcagtagc caatttttgt cacgtcgtta taacaaggag    6300
atgacataat taaacatttc catcctttct attccctgag actgcatcag cacaggcaag    6360
tatagaatgt aatgttcttc atgggcccca ccagcttttt ggtgccatgt aatttatttc    6420
ttcgctgaag agaaaagaa ttctgagaca cagttattaa acccttttatc aactttctac    6480 catcagtgcc tgaattctaa tgcagtgtga tttctctggg acaaagagac tgaggaagat    6540
gaaaagtttc ttcaaagagt gaatacatac ttattcacaa ctctaggatg tgaggacttt    6600
aaatatctct ttatgaagtt ccctgcctaa cctctttcta tttaaaggca aacaaatttc    6660
gaagaggttt tgtgttccct ctttatgttt ctctatgacc cagtttagtc taaaacctta    6720
gttcattaca tatacaacac atagccttg atccctggta actggcaggt gttggtgatt    6780
aataaaccaa ggcttcaaag tgaagtatgt gtgtgcagat gacttttgga ataacgtggg    6840
catagcatca taccttcctg attgtcttca gcatataaaa attaactgtt gtagttaaaa    6900
ttatgtcagt gcagagcttg tggttacttg gaatgttctt tcagaatagt ccatgttgcc    6960
tattaaacct agttttaaac acattgggca gtcaatttat gcacccaaaa tatcacccctc    7020 aggtagattg agggcaagat aaaatgctgt atgtagctat acaaaggaat tcagaaacat    7080
tactggaaag caaagccttt gtcagcttgc tactgacaaa gtagtaaaaa gctactaatc    7140
agtgttgagt cagatgtcaa cagaaaaata caaatacccta tgagagccac agcagtttct    7200
cgtttcatag ccgattcaat gaatatgatt agaaattcac tgagctcact cttgcaggtt    7260
taaatggagg cctgcataag gactgcaaga ggaaatctgg gtgggagaga atgtaatctg    7320
atcttgcact cataggcaat gctgcaatgc aatcatgtcc aatacaagca cagcttcatt    7380
cataacagga aacgtcttct ttgggaaaat agctctattg gtgcccaaac tcaggtatgc    7440
cagtgtatgc aggtggagtc gccctacccc tcttccaaac atgtcctgtg agattttaa    7500 aataagatgg gatagtacag gggcatgaaa agaattgatt ccttcacagg atttgaatcc    7560
```

-continued

```
agttcaaggg agaatgtaga aaattcaaaa ccaacatata aggtatcaca caaccaagaa    7620
aagtaaaacc attgcaagtt tacttgcgtt gagtacaaaa cagatttaat ggtgttctat    7680
gtcatagttt aatgctctgg gtatttaaat atgttttcaa caggatttga gttgaaagtt    7740
tgtaatgtgc tttgatggaa cacctctcaa tttctattca ataaactyat gtaattgtcc    7800
attgacaata taatgataac agtaccattg aactctaaac tgtggtttat cttcactact    7860
gggaagcaac tgtgcatcag tattaaagat atgcagaaac ataatattca ctaatttgtt    7920
catctgcttc tgtatattgt ttatggaatt acatggcaag aactgttcta aagcaacatg    7980
tctttccaca ttatttttaga ggtgaaatta cttttgtttt gcttctctat aatgtgtact    8040
tcaaatgaaa caccatactt ttttctaaaa aaagatgttc aatttactaa ttttttttaaa   8100
tctcataatt taaaaagcat ttgttgtgat tttaaagtgt tgcaagaaaa gggatttttgt   8160
ggccgtgggt agacttttta tactttgttt tatagatgga ttttttttaa ctgtagtttg    8220
tttaagtcac caagcagcat ccaaaatctt aatgtgtttc atttgatgtt gttagatcag    8280
agaagaaatt ggcataaaat cggttaatag tattgtcaaa gaattgtgta ttgtgtactc    8340
actgggaaaa aataaaatat attcacattt caaa                                8374
```

<210> SEQ ID NO 3
<211> LENGTH: 1378
<212> TYPE: PRT
<213> ORGANISM: Homo sapiens

<400> SEQUENCE: 3

```
Met Ser Leu Leu Met Phe Thr Gln Leu Leu Leu Cys Gly Phe Leu Tyr
1               5                   10                  15

Val Arg Val Asp Gly Ser Arg Leu Arg Gln Glu Asp Phe Pro Pro Arg
            20                  25                  30

Ile Val Glu His Pro Ser Asp Val Ile Val Ser Lys Gly Glu Pro Thr
        35                  40                  45

Thr Leu Asn Cys Lys Ala Glu Gly Arg Pro Thr Pro Thr Ile Glu Trp
    50                  55                  60

Tyr Lys Asp Gly Glu Arg Val Glu Thr Asp Lys Asp Asp Pro Arg Ser
65                  70                  75                  80

His Arg Met Leu Leu Pro Ser Gly Ser Leu Phe Phe Leu Arg Ile Val
                85                  90                  95

His Gly Arg Arg Ser Lys Pro Asp Glu Gly Ser Tyr Val Cys Val Ala
            100                 105                 110

Arg Asn Tyr Leu Gly Glu Ala Val Ser Arg Asn Ala Ser Leu Glu Val
        115                 120                 125

Ala Leu Leu Arg Asp Asp Phe Arg Gln Asn Pro Thr Asp Val Val Val
    130                 135                 140

Ala Ala Gly Glu Pro Ala Ile Leu Glu Cys Gln Pro Pro Arg Gly His
145                 150                 155                 160

Pro Glu Pro Thr Ile Tyr Trp Lys Lys Asp Lys Val Arg Ile Asp Asp
                165                 170                 175

Lys Glu Glu Arg Ile Ser Ile Arg Gly Gly Lys Leu Met Ile Ser Asn
            180                 185                 190

Thr Arg Lys Ser Asp Ala Gly Met Tyr Thr Cys Val Gly Thr Asn Met
        195                 200                 205

Val Gly Glu Arg Asp Ser Asp Pro Ala Glu Leu Thr Val Phe Glu Arg
    210                 215                 220
```

```
Pro Thr Phe Leu Arg Arg Pro Ile Asn Gln Val Val Leu Glu Glu Glu
225                 230                 235                 240

Ala Val Glu Phe Arg Cys Gln Val Gln Gly Asp Pro Gln Pro Thr Val
        245                 250                 255

Arg Trp Lys Lys Asp Asp Ala Asp Leu Pro Arg Gly Arg Tyr Asp Ile
            260                 265                 270

Lys Asp Asp Tyr Thr Leu Arg Ile Lys Lys Thr Met Ser Thr Asp Glu
            275                 280                 285

Gly Thr Tyr Met Cys Ile Ala Glu Asn Arg Val Gly Lys Met Glu Ala
        290                 295                 300

Ser Ala Thr Leu Thr Val Arg Ala Pro Pro Gln Phe Val Val Arg Pro
305                 310                 315                 320

Arg Asp Gln Ile Val Ala Gln Gly Arg Thr Val Thr Phe Pro Cys Glu
                325                 330                 335

Thr Lys Gly Asn Pro Gln Pro Ala Val Phe Trp Gln Lys Glu Gly Ser
            340                 345                 350

Gln Asn Leu Leu Phe Pro Asn Gln Pro Gln Pro Asn Ser Arg Cys
        355                 360                 365

Ser Val Ser Pro Thr Gly Asp Leu Thr Ile Thr Asn Ile Gln Arg Ser
370                 375                 380

Asp Ala Gly Tyr Tyr Ile Cys Gln Ala Leu Thr Val Ala Gly Ser Ile
385                 390                 395                 400

Leu Ala Lys Ala Gln Leu Glu Val Thr Asp Val Leu Thr Asp Arg Pro
                405                 410                 415

Pro Pro Ile Ile Leu Gln Gly Pro Ala Asn Gln Thr Leu Ala Val Asp
            420                 425                 430

Gly Thr Ala Leu Leu Lys Cys Lys Ala Thr Gly Asp Pro Leu Pro Val
        435                 440                 445

Ile Ser Trp Leu Lys Glu Gly Phe Thr Phe Pro Gly Arg Asp Pro Arg
450                 455                 460

Ala Thr Ile Gln Glu Gln Gly Thr Leu Gln Ile Lys Asn Leu Arg Ile
465                 470                 475                 480

Ser Asp Thr Gly Thr Tyr Thr Cys Val Ala Thr Ser Ser Ser Gly Glu
                485                 490                 495

Thr Ser Trp Ser Ala Val Leu Asp Val Thr Glu Ser Gly Ala Thr Ile
            500                 505                 510

Ser Lys Asn Tyr Asp Leu Ser Asp Leu Pro Gly Pro Pro Ser Lys Pro
        515                 520                 525

Gln Val Thr Asp Val Thr Lys Asn Ser Val Thr Leu Ser Trp Gln Pro
530                 535                 540

Gly Thr Pro Gly Thr Leu Pro Ala Ser Ala Tyr Ile Ile Glu Ala Phe
545                 550                 555                 560

Ser Gln Ser Val Ser Asn Ser Trp Gln Thr Val Ala Asn His Val Lys
                565                 570                 575

Thr Thr Leu Tyr Thr Val Arg Gly Leu Arg Pro Asn Thr Ile Tyr Leu
            580                 585                 590

Phe Met Val Arg Ala Ile Asn Pro Gln Gly Leu Ser Asp Pro Ser Pro
        595                 600                 605

Met Ser Asp Pro Val Arg Thr Gln Asp Ile Ser Pro Pro Ala Gln Gly
            610                 615                 620

Val Asp His Arg Gln Val Gln Lys Glu Leu Gly Asp Val Leu Val Arg
625                 630                 635                 640

Leu His Asn Pro Val Val Leu Thr Pro Thr Thr Val Gln Val Thr Trp
```

-continued

```
                645                 650                 655
Thr Val Asp Arg Gln Pro Gln Phe Ile Gln Gly Tyr Arg Val Met Tyr
                    660                 665                 670
Arg Gln Thr Ser Gly Leu Gln Ala Thr Ser Ser Trp Gln Asn Leu Asp
            675                 680                 685
Ala Lys Val Pro Thr Glu Arg Ser Ala Val Leu Val Asn Leu Lys Lys
690                 695                 700
Gly Val Thr Tyr Glu Ile Lys Val Arg Pro Tyr Phe Asn Glu Phe Gln
705                 710                 715                 720
Gly Met Asp Ser Glu Ser Lys Thr Val Arg Thr Thr Glu Glu Ala Pro
                725                 730                 735
Ser Ala Pro Pro Gln Ser Val Thr Val Leu Thr Val Gly Ser Tyr Asn
                740                 745                 750
Ser Thr Ser Ile Ser Val Ser Trp Asp Pro Pro Pro Asp His Gln
            755                 760                 765
Asn Gly Ile Ile Gln Glu Tyr Lys Ile Trp Cys Leu Gly Asn Glu Thr
770                 775                 780
Arg Phe His Ile Asn Lys Thr Val Asp Ala Ala Ile Arg Ser Val Ile
785                 790                 795                 800
Ile Gly Gly Leu Phe Pro Gly Ile Gln Tyr Arg Val Glu Val Ala Ala
                805                 810                 815
Ser Thr Ser Ala Gly Val Gly Val Lys Ser Glu Pro Gln Pro Ile Ile
                820                 825                 830
Ile Gly Arg Arg Asn Glu Val Val Ile Thr Glu Asn Asn Ser Ile
            835                 840                 845
Thr Glu Gln Ile Thr Asp Val Val Lys Gln Pro Ala Phe Ile Ala Gly
        850                 855                 860
Ile Gly Gly Ala Cys Trp Val Ile Leu Met Gly Phe Ser Ile Trp Leu
865                 870                 875                 880
Tyr Trp Arg Arg Lys Lys Arg Lys Gly Leu Ser Asn Tyr Ala Val Thr
                885                 890                 895
Phe Gln Arg Gly Asp Gly Gly Leu Met Ser Asn Gly Ser Arg Pro Gly
                900                 905                 910
Leu Leu Asn Ala Gly Asp Pro Ser Tyr Pro Trp Leu Ala Asp Ser Trp
        915                 920                 925
Pro Ala Thr Ser Leu Pro Val Asn Asn Ser Asn Ser Gly Pro Asn Glu
        930                 935                 940
Ile Gly Asn Phe Gly Arg Gly Asp Val Leu Pro Pro Val Pro Gly Gln
945                 950                 955                 960
Gly Asp Lys Thr Ala Thr Met Leu Ser Asp Gly Ala Ile Tyr Ser Ser
                965                 970                 975
Ile Asp Phe Thr Thr Lys Thr Ser Tyr Asn Ser Ser Gln Ile Thr
            980                 985                 990
Gln Ala Thr Pro Tyr Ala Thr Thr  Gln Ile Leu His Ser  Asn Ser Ile
                995                 1000                1005
His Glu  Leu Ala Val Asp Leu  Pro Asp Pro Gln Trp  Lys Ser Ser
        1010                1015                1020
Ile Gln  Gln Lys Thr Asp Leu  Met Gly Phe Gly Tyr  Ser Leu Pro
        1025                1030                1035
Asp Gln  Asn Lys Gly Asn Asn  Gly Gly Lys Gly  Lys Lys Lys
        1040                1045                1050
Lys Asn  Lys Asn Ser Ser Lys  Pro Gln Lys Asn Asn  Gly Ser Thr
        1055                1060                1065
```

| | | | | | | | | | | |
|---|---|---|---|---|---|---|---|---|---|---|
| Trp | Ala | Asn | Val | Pro | Leu | Pro | Pro | Pro | Val | Gln | Pro | Leu | Pro |
| | 1070 | | | | 1075 | | | | 1080 | | | |

Trp Ala Asn Val Pro Leu Pro Pro Pro Val Gln Pro Leu Pro
    1070                       1075                     1080

Gly Thr Glu Leu Glu His Tyr Ala Val Glu Gln Gln Glu Asn Gly
    1085                       1090                     1095

Tyr Asp Ser Asp Ser Trp Cys Pro Pro Leu Pro Val Gln Thr Tyr
    1100                       1105                     1110

Leu His Gln Gly Leu Glu Asp Glu Leu Glu Glu Asp Asp Asp Arg
    1115                       1120                     1125

Val Pro Thr Pro Pro Val Arg Gly Val Ala Ser Ser Pro Ala Ile
    1130                       1135                     1140

Ser Phe Gly Gln Gln Ser Thr Ala Thr Leu Thr Pro Ser Pro Arg
    1145                       1150                     1155

Glu Glu Met Gln Pro Met Leu Gln Ala His Leu Asp Glu Leu Thr
    1160                       1165                     1170

Arg Ala Tyr Gln Phe Asp Ile Ala Lys Gln Thr Trp His Ile Gln
    1175                       1180                     1185

Ser Asn Asn Gln Pro Pro Gln Pro Pro Val Pro Pro Leu Gly Tyr
    1190                       1195                     1200

Val Ser Gly Ala Leu Ile Ser Asp Leu Glu Thr Asp Val Ala Asp
    1205                       1210                     1215

Asp Asp Ala Asp Asp Glu Glu Ala Leu Glu Ile Pro Arg Pro
    1220                       1225                     1230

Leu Arg Ala Leu Asp Gln Thr Pro Gly Ser Ser Met Asp Asn Leu
    1235                       1240                     1245

Asp Ser Ser Val Thr Gly Lys Ala Phe Thr Ser Ser Gln Arg Pro
    1250                       1255                     1260

Arg Pro Thr Ser Pro Phe Ser Thr Asp Ser Asn Thr Ser Ala Ala
    1265                       1270                     1275

Leu Ser Gln Ser Gln Arg Pro Arg Pro Thr Lys Lys His Lys Gly
    1280                       1285                     1290

Gly Arg Met Asp Gln Gln Pro Ala Leu Pro His Arg Arg Glu Gly
    1295                       1300                     1305

Met Thr Asp Glu Glu Ala Leu Val Pro Tyr Ser Lys Pro Ser Phe
    1310                       1315                     1320

Pro Ser Pro Gly Gly His Ser Ser Ser Gly Thr Ala Ser Ser Lys
    1325                       1330                     1335

Gly Ser Thr Gly Pro Arg Lys Thr Glu Val Leu Arg Ala Gly His
    1340                       1345                     1350

Gln Arg Asn Ala Ser Asp Leu Leu Asp Ile Gly Tyr Met Gly Ser
    1355                       1360                     1365

Asn Ser Gln Gly Gln Phe Thr Gly Glu Leu
    1370                       1375

<210> SEQ ID NO 4
<211> LENGTH: 8689
<212> TYPE: DNA
<213> ORGANISM: Homo sapiens

<400> SEQUENCE: 4

```
ctcctctctt ttggaaaccg agaggtgga  gggagggcaa caccgctgca aaggagaggc      60
ccgccaagtc tgcccgcctg caaagtgttg ctttgacaca ttcttattat ggaagttaag     120 taaaatata  gacatattaa aaaataactc cggacgtgga gctgctacgg agaaggaaac     180
cgggggaaag aaaaccagta ggcaggccaa tggtttttcg gcagcgcgct ggcaagtttg     240
```

```
tggaacactt tctaggaatt aggtcttttc ctcccccttc atcatcttga cttctgaagg     300
aagaacttgg cttttggattg cagtggagcc taaggagaga gggttagaca cactcgaata    360
atccctctgg ctgggctgaa tttgtgggaa tttaggaagc cagagtgctg gaaatacagc    420
agcctttgaa gtaccctctg ttaatttgga tggatctcag tgtgccccgt tcgagacctc    480
tccaccaacc ccttctgatc ttgcgatttg ctcttcttga ctttaattag tatctaggaa    540
agtctaaact ttggacctac ctcttttttt gatactcatt tttgtacttt tgctctctgg    600
gattggtttc ttaaagaatc tggatccttt ttaatatgtc aaaatgagtc tgctgatgtt    660
tacacaacta ctgctctgtg gatttttata tgttcgggtt gatggatcgc gtcttcgcca    720
ggaggacttt cccccgcgga ttgtggagca tccttccgat gtcatcgtct ctaagggcga    780
gcccacgact ctgaactgca aggcggaggg ccggccaacg cccaccattg agtggtacaa    840
agatggggag cgagtggaga ctgacaagga cgatcccgg tcccacagga tgcttctgcc     900
cagcggatcc ttattcttct tgcgcatcgt gcacgggcgc aggagtaaac ctgatgaagg   960
aagctacgtt tgtgttgcga ggaactatct tggtgaagca gtgagtcgaa atgcgtctct   1020
ggaagtggca ttgttacgag atgacttccg acaaaacccc acagatgttg tagtggcagc   1080
tggagagcct gcaatcctgg agtgccagcc tccccgggga cacccagaac ccaccatcta   1140
ctggaaaaaa gacaaagttc gaattgatga caaggaagaa agaataagta ccgtggtgg    1200 aaaactgatg atctccaata ccaggaaaag tgatgcaggg atgtatactt gtgttggtac   1260
caatatggtg ggagaaaggg acagtgaccc agcagagctg actgtctttg aacgacccac   1320
atttctcagg aggccaatta accaggtggt actggaggaa gaagctgtag aatttcgttg   1380
tcaagtccaa ggagatcctc aaccaactgt gaggtggaaa aaggatgatg cagacttgcc   1440
aagaggaagg tatgacatca aagacgatta cacactaaga attaaaaaga ccatgagtac   1500
agatgaaggc acctatatgt gtattgctga gaatcgggtt ggaaaaatgg aagcctctgc   1560
tacactcacc gtccgagctc ccccacagtt tgtggttcgg ccaagagatc agattgttgc   1620
tcaaggtcga acagtgacat ttccctgtga aactaaagga aacccacagc cagctgtttt   1680
ttggcagaaa gaaggcagcc agaacctact tttcccaaac caaccccagc agcccaacag   1740
tagatgctca gtgtcaccaa ctggagacct cacaatcacc aacattcaac gttccgacgc   1800
gggttactac atctgccagg ctttaactgt ggcaggaagc attttagcaa aagctcaact   1860
ggaggttact gatgttttga cagatagacc tccacctata attctacaag gcccagccaa   1920
ccaaacgctg gcagtggatg gtacagcgtt actgaaatgt aaagccactg gtgatcctct   1980
tcctgtaatt agctggttaa aggagggatt tacttttccg ggtagagatc aagagcaac    2040 aattcaagag caaggcacac tgcagattaa gaatttacgg atttctgata ctggcactta   2100
tacttgtgtg gctacaagtt caagtggaga gacttcctgg agtgcagtgc tggatgtgac   2160
agagtctgga gcaacaatca gtaaaaacta tgatttaagt gacctgccag gccaccatc    2220 caaaccgcag gtcactgatg ttactaagaa cagtgtcacc ttgtcctggc agccaggtac   2280
ccctggaacc cttccagcaa gtgcatatat cattgaggct ttcagccaat cagtgagcaa   2340
cagctggcag accgtggcaa accatgtaaa gaccaccctc tatactgtaa gaggactgcg   2400
gcccaataca atctacttat tcatggtcag agcgatcaac cccaaggtc tcagtgaccc    2460 aagtcccatg tcagatcctg tgcgcacaca agatatcagc ccaccagcac aaggagtgga   2520
ccacaggcaa gtgcagaaag agctaggaga tgtccttgtc cgtcttcata atccagttgt   2580
```

```
gctgactccc accacggttc aggtcacatg gacggttgat cgccaacccc agtttatcca    2640
aggctaccga gtgatgtatc gtcagacttc aggtctgcag gcgacatctt cgtggcagaa    2700
tttagatgcc aaagtcccga ctgaacgaag tgctgtctta gtcaacctga aaaggggggt    2760
gacttatgaa attaaagtac ggccatattt taatgagttc caaggaatgg atagtgaatc    2820
taaaacggtt cgtactactg aagaagcccc aagtgcccca ccacagtctg tcactgtact    2880
gacagttgga agctacaata gcacaagtat tagtgtttcc tgggatcctc ctcctccaga    2940
tcaccagaat ggaattatcc aagaatacaa gatctggtgt ctaggaaatg aaacgcgatt    3000
ccatatcaac aaaactgtgg atgcagccat tcggtccgta ataattggtg gattattccc    3060
aggtattcaa taccgggtag aggttgcagc tagtaccagt gcaggggttg gagtaaagag    3120
tgagccacag ccaataataa tcgggagacg caatgaagtt gtcattactg aaaacaataa    3180
cagcataact gagcaaatca ctgatgtggt gaagcaacca gcctttatag ctggtattgg    3240
tggtgcctgc tgggtaattc tgatgggttt tagcatatgg ttgtattggc gaagaaagaa    3300
gaggaaggga ctcagtaatt atgctgttac gtttcaaaga ggagatggag gactaatgag    3360
caatggaagc cgtccaggtc ttctcaatgc tggtgatccc agctatccat ggcttgctga    3420
ttcttggcca gccacgagct tgccagtaaa taatagcaac agtggcccaa atgagattgg    3480
aaattttggc cgtggagatg tgctgccacc agttccaggc caggggata aaacagcaac    3540 gatgctctca gatggagcca tttatagtag cattgacttc actaccaaaa ccagttacaa    3600
cagttccagc caaataacac aggctacccc atatgccacg acacagatct tgcattccaa    3660
cagcatacat gaattggctg tcgatctgcc tgatccacaa tggaaaagct caattcagca    3720
aaaaacagat ctgatgggat ttggttattc tctacctgat cagaacaaag gtaacaatgg    3780
tgggaaaggt ggaaaaaaga agaaaaataa aaactcttct aaaccacaga aaacaatgg    3840 atccacttgg gccaatgtcc ctctacctcc cccccagtc cagcccttc ctggcacgga    3900 gctggaacac tatgcagtgg aacaacaaga aaatggctat gacagtgata gctggtgccc    3960
accattgcca gtacaaactt acttacacca aggtctggaa gatgaactgg aagaagatga    4020
tgatagggtc ccaacacctc ctgttcgagg cgtggcttct tctcctgcta tctcctttgg    4080
acagcagtcc actgcaactc ttactccatc cccacgggaa gagatgcaac ccatgctgca    4140
ggctcacctg gatgagttga caagagccta tcagtttgat atagcaaaac aaacatggca    4200
cattcaaagc aataatcaac ctccacagcc tccagttcca ccgttaggtt atgtgtctgg    4260
agccttgatt tctgatttgg aaacggatgt tgcagatgat gatgccgacg acgaagagga    4320
agctttagaa atccccaggc ccctgagagc actggaccag actcctggat ccagcatgga    4380
caatctagac agctctgtga caggaaaagc ctttacctcc tctcaaagac tcgacctac    4440 cagcccattt tctactgaca gtaacaccag tgcagccctg agtcaaagtc agaggcctcg    4500
gcccactaaa aaacacaagg gagggcggat ggaccaacaa ccagcattgc ctcatcgaag    4560
ggaaggaatg acagatgagg aggccttggt gccctatagc aagcccagtt tcccatctcc    4620
aggtggccac agctcatcag gaacagcttc ttctaaggga tccactggac ctaggaaaac    4680
cgaggtgttg agagcaggcc accagcgcaa tgccagcgca cttcttgaca taggatatat    4740
gggctccaac agtcaaggac agtttacagg tgaattatag taaatgagag gagacataca    4800
aagctgctct gaaggaccat caggtccgga ctcatggaag tgatgactct aaacagtgca    4860
atgaacaatt tatttatgta ctattaaaag aactgtaaat gcaatgtaaa gacacacagc    4920
cacacatatc ccacagatat tttcattgtg ttcttctctt aagtacacca cccacccttaa    4980
```

```
ctctttcttg tcaggagtat ataaaaaaga aagaaaacaa aactcgccct acaggaagaa    5040
aaggattctc ctctgtatat aatttctttt gtgcattgct atgcaagctc actcttttta    5100
gctctgctca tattattgtc tgttcttatt ggtctgttgt actatatgtg aattaatagg    5160
ctgtggtgcc atatattaac ttttaattgt gtaacttttta tgtttaaatt ttgcactgca    5220 atttttatttg gtgataagca caaatctcta ctcctcatga catgaagaaa aagactgaat    5280
gtgaagggag tttctgtact gtaagctaga ttggataatg atggctgtaa caaatcatgt    5340
tagatggttt tcagttgggg tgtagaaata ggaagatgca aaggaacaat ggtgttggca    5400
aagtcttctt tgaatatcag ggactgagtc aataaaaaaa atagtagaaa ggtggctttt    5460
actattgaca aaagccgggg tcaaaaaaag tagtttaagt cttaagactg aatatgcatt    5520
aaagtatgca ggtagcaaag atgtaataaa tttgcttaaa aaaagaaatt aaagttttat    5580
ttagaatcaa ttttacctgt cattgtaatt gacccatctg agaattacaa taagcaagag    5640
gaaattaagg tgttttgcaa gagctgtatt tatattacag ttttttaaaa acattttctg    5700
aattatcgta attaagctct ccaactcgtt aagtcagaat ataatatgaa gttccccaag    5760
gaaacgaaca aaatgaactc tagaatatct agcaaatagt taaagaagca atttattatt    5820
agggcatact cgggctgttt ccaaatataa actctattgc aatatcttat ttcatctttc    5880
taatacatgt acagtgcaca ctagaggata gagctgcatc acttaaattc atgacttaaa    5940
aaataataca gtttatatac aacttgtttt ttatttgatt aagaagtgaa gtttacgcca    6000
cccaatgtat agccaaattg tacgtgctta aaaaacagtg ccgagagtat gttcagttcg    6060
cagtaagtag atttattgga ataaatattc tatggtacat tctcagaaat tggcttccaa    6120
ctaaaatacg tttgacccat tttgaataag gaaattgaaa agaaaaattt aaaaggagaa    6180
aaaaatgcat gtttataaac ttttttaaata aaaccagacc ttgtaagtgg acattaataa    6240
ttgtcctgcc tcatttgttt tcacgacttt gacaacaaga agttcctgaa cattagtcat    6300
gtatgctcag aataaatgtg actttgaaat atatgttagc tactgtacat gtatagtcag    6360
tcaagtagaa gaggaccttc ctgaaattcc cacttgtgac attttcccat gggtttccta    6420
cacaatctta aattttatttt ctgtctatac tttctcaaat ttttcctatg ataagttcag    6480
ttgttggtac tcttctaaaa atattcaacg tgattaggat cagttctaaa atacgggacc    6540
cctttgagtg acaattcgca ctccatgcat tattggctca gtagccaatt tttgtcacgt    6600
cgttataaca aggagatgac ataattaaac atttccatcc tttctattcc ctgagactgc    6660
atcagcacac gcaagtatag aatgtaatgt tcttcatggg ccccaccagc ttttggtgc    6720 catgtaattt atttcttcgc tgaagagaaa aagaattctg agacacagtt attaaaccct    6780
ttatcaactt tctaccatca gtgcctgaat tctaatgcag tgtgatttct ctgggacaaa    6840
gagactgagg aagatgaaaa gtttcttcaa agagtgaata catacttatt cacaactcta    6900
ggatgtgagg actttaaata tctctttatg aagttccctg cctaacctct ttctatttaa    6960
aggcaaacaa atttcgaaga ggttttgtgt tccctctttta tgtttctcta tgacccagtt    7020
tagtctaaaa ccttagttca ttacatatac aacacatagc ctttgatccc tggtaactgg    7080
caggtgttgg tgattaataa accaaggctt caaagtgaag tatgtgtgtg cagatgactt    7140
ttggaataac gtgggcatag catcataccT tcctgattgt cttcagcata taaaaattaa    7200
ctgttgtagt taaaattatg tcagtgcaga gcttgtggtt acttggaatg ttctttcaga    7260
atagtccatg ttgcctatta aacctagttt taaacacatt gggcagtcaa tttatgcacc    7320
```

```
caaaatatca ccctcaggta gattgagggc aagataaaat gctgtatgta gctatacaaa      7380
ggaattcaga acattactg gaaagcaaag cctttgtcag cttgctactg acaaagtagt        7440
aaaaagctac taatcagtgt tgagtcagat gtcaacagaa aaatacaaat acctatgaga      7500
gccacagcag tttctcgttt catagccgat tcaatgaata tgattagaaa ttcactgagc      7560
tcactcttgc aggtttaaat ggaggcctgc ataaggactg caagaggaaa tctgggtggg      7620
agagaatgta atctgatctt gcactcatag gcaatgctgc aatgcaatca tgtccaatac      7680
aagcacagct tcattcataa caggaaacgt cttctttggg aaaatagctc tattggtgcc      7740
caaactcagg tatgccagtg tatgcaggtg gagtcgccct accctcttc caaacatgtc       7800
ctgtgagatt tttaaaataa gatgggatag tacaggggca tgaaaagaat tgattccttc      7860
acaggatttg aatccagttc aagggagaat gtagaaaatt caaaccaac atataaggta       7920
tcacacaacc aagaaaagta aaaccattgc aagtttactt gcgttgagta caaaacagat      7980
ttaatggtgt tctatgtcat agtttaatgc tctgggtatt taaatatgtt ttcaacagga      8040
tttgagttga aagtttgtaa tgtgctttga tggaacacct ctcaatttct attcaataaa      8100
cttatgtaat tgtccattga caatataatg ataacagtac cattgaactc taaactgtgg      8160
tttatcttca ctactgggaa gcaactgtgc atcagtatta aagatatgca gaaacataat      8220
attcactaat ttgttcatct gcttctgtat attgtttatg gaattacatg caagaactg       8280
ttctaaagca acatgtcttt ccacattatt ttagaggtga attactttt gttttgcttc       8340
tctataatgt gtacttcaaa tgaaacacca tacttttttc taaaaaaaga tgttcaattt      8400
actaattttt ttaaatctca taatttaaaa agcatttgtt gtgattttaa agtgttgcaa      8460
gaaaagggat tttgtggccg tgggtagact ttttatactt tgttttatag atggattttt     8520
tttaactgta gtttgtttaa gtcaccaagc agcatccaaa atcttaatgt gtttcatttg     8580
atgttgttag atcagagaag aaattggcat aaaatcggtt aatagtattg tcaaagaatt    8640
gtgtattgtg tactcactgg gaaaaaataa aatatattca catttcaaa                 8689
```

<210> SEQ ID NO 5
<211> LENGTH: 216
<212> TYPE: PRT
<213> ORGANISM: Homo sapiens

<400> SEQUENCE: 5

Thr Glu Leu Glu His Tyr Ala Val Glu Gln Gln Glu Asn Gly Tyr Asp
1               5                   10                  15

Ser Asp Ser Trp Cys Pro Pro Leu Pro Val Gln Thr Tyr Leu His Gln
            20                  25                  30

Gly Leu Glu Asp Glu Leu Glu Glu Asp Asp Arg Val Pro Thr Pro
        35                  40                  45

Pro Val Arg Gly Val Ala Ser Ser Pro Ala Ile Ser Phe Gly Gln Gln
    50                  55                  60

Ser Thr Ala Thr Leu Thr Pro Ser Pro Arg Glu Met Gln Pro Met
65                  70                  75                  80

Leu Gln Ala His Leu Asp Glu Leu Thr Arg Ala Tyr Gln Phe Asp Ile
                85                  90                  95

Ala Lys Gln Thr Trp His Ile Gln Ser Asn Asn Gln Pro Pro Gln Pro
            100                 105                 110

Pro Val Pro Pro Leu Gly Tyr Val Ser Gly Ala Leu Ile Ser Asp Leu
        115                 120                 125

Glu Thr Asp Val Ala Asp Asp Asp Ala Asp Asp Glu Glu Glu Ala Leu

```
                130                 135                 140
Glu Ile Pro Arg Pro Leu Arg Ala Leu Asp Gln Thr Pro Gly Ser Ser
145                 150                 155                 160

Met Asp Asn Leu Asp Ser Ser Val Thr Gly Lys Ala Phe Thr Ser Ser
                165                 170                 175

Gln Arg Pro Arg Pro Thr Ser Pro Phe Ser Thr Asp Ser Asn Thr Ser
            180                 185                 190

Ala Ala Leu Ser Gln Ser Gln Arg Pro Arg Pro Thr Lys His Lys Gly
        195                 200                 205

Gly Arg Met Asp Gln Gln Pro Ala
    210                 215

<210> SEQ ID NO 6
<211> LENGTH: 217
<212> TYPE: PRT
<213> ORGANISM: Homo sapiens

<400> SEQUENCE: 6

Thr Glu Leu Glu His Tyr Ala Val Glu Gln Gln Glu Asn Gly Tyr Asp
1               5                   10                  15

Ser Asp Ser Trp Cys Pro Pro Leu Pro Val Gln Thr Tyr Leu His Gln
                20                  25                  30

Gly Leu Glu Asp Glu Leu Glu Glu Asp Asp Asp Arg Val Pro Thr Pro
            35                  40                  45

Pro Val Arg Gly Val Ala Ser Ser Pro Ala Ile Ser Phe Gly Gln Gln
        50                  55                  60

Ser Thr Ala Thr Leu Thr Pro Ser Pro Arg Glu Glu Met Gln Pro Met
65                  70                  75                  80

Leu Gln Ala His Leu Asp Glu Leu Thr Arg Ala Tyr Gln Phe Asp Ile
                85                  90                  95

Ala Lys Gln Thr Trp His Ile Gln Ser Asn Asn Gln Pro Pro Gln Pro
                100                 105                 110

Pro Val Pro Pro Leu Gly Tyr Val Ser Gly Ala Leu Ile Ser Asp Leu
            115                 120                 125

Glu Thr Asp Val Ala Asp Asp Ala Asp Asp Glu Glu Glu Ala Leu
        130                 135                 140

Glu Ile Pro Arg Pro Leu Arg Ala Leu Asp Gln Thr Pro Gly Ser Ser
145                 150                 155                 160

Met Asp Asn Leu Asp Ser Ser Val Thr Gly Lys Ala Phe Thr Ser Ser
                165                 170                 175

Gln Arg Pro Arg Pro Thr Ser Pro Phe Ser Thr Asp Ser Asn Thr Ser
            180                 185                 190

Ala Ala Leu Ser Gln Ser Gln Arg Pro Arg Pro Thr Lys Lys His Lys
        195                 200                 205

Gly Gly Arg Met Asp Gln Gln Pro Ala
    210                 215
```

ROBO2 INHIBITORY COMPOSITIONS COMPRISING SLIT2-BINDING EXTRACELLULAR DOMAIN OF ROBO2

CROSS REFERENCE TO RELATED APPLICATIONS

This application is a 35 U.S.C. §371 National Phase Entry Application of International Application No. PCT/US2013/020280 filed Jan. 4, 2013, which designates the U.S., and which claims benefit under 35 U.S.C. §119(e) of U.S. Provisional Patent Application Ser. No. 61/583,379 filed on 5 Jan. 2012, the contents of which are incorporated herein by reference in its entirety.

GOVERNMENT SUPPORT

This invention was made with Government Support under Contract No. DK078226 awarded by the National Institutes of Health. The Government has certain rights in the invention.

FIELD OF THE INVENTION

The field of the invention relates to methods for the treatment of chronic kidney disease and proteinuria and for the diagnosis of chronic kidney disease and monitoring the effects of treatment on the progression of chronic kidney disease and proteinuria.

SEQUENCE LISTING

The instant application contains a Sequence Listing which has been submitted in ASCII format via EFS-Web and is hereby incorporated by reference in its entirety. Said ASCII copy, created on Feb. 14, 2013, is named 701586-072811-PCT_SL.txt and is 50,526 bytes in size.

SUMMARY OF THE INVENTION

Provided herein are novel methods for the treatment of chronic kidney disease and proteinuria and for the diagnosis of chronic kidney disease, and monitoring the effects of treatment on the progression of chronic kidney disease and proteinuria based, in part, on the inventors' discovery of a novel and unexpected role for the SLIT-ROBO signaling pathway in the regulation of podocyte F-actin cytoskeleton and foot process structure in the kidney.

Accordingly, in some aspects, provided herein are methods for the treatment of chronic kidney disease in a subject in need thereof, the methods comprising administering to a subject having or at risk for a chronic kidney disease a therapeutically effective amount of a composition comprising a ROBO2 inhibitor.

Also provided herein, in some aspects, are method for the reduction of proteinuria in a subject in need thereof, comprising administering to a subject having or at risk for proteinuria a therapeutically effective amount of a composition comprising a ROBO2 inhibitor.

In some embodiments of these methods and all such methods described herein, the ROBO2 inhibitor is a blocking antibody or antigen-binding fragment thereof specific for ROBO2, an antisense molecule specific for ROBO2, a short interfering RNA (siRNA) specific for ROBO2, a small molecule inhibitor of ROBO2, a ROBO2 inhibitory polypeptide, or a ROBO2 structural analog.

In some embodiments of these methods and all such methods described herein, the ROBO2 inhibitor blocks or reduces binding of ROBO2 to SLIT, to Nck, or to both.

In some embodiments of these methods and all such methods described herein, the ROBO2 inhibitor is specific for the Ig1 SLIT binding domain, the Ig1 and Ig2 SLIT binding domains, the Nck intracellular binding domain, or any combination thereof.

In some embodiments of these methods and all such methods described herein, the ROBO2 inhibitory polypeptide is a dominant negative ROBO2 fusion protein, a polypeptide comprising a ROBO2 extracellular domain without the intracellular domain, or a polypeptide comprising a ROBO2 intracellular domain without the extracellular domain.

In some embodiments of these methods and all such methods described herein, the subject having or at risk for a chronic kidney disease has diabetic nephropathy or high blood pressure.

In some embodiments of these methods and all such methods described herein, the method further comprises administering to the subject an additional therapeutic agent.

In some embodiments of these methods and all such methods described herein, the additional therapeutic agent is an angiotensin-converting enzyme (ACE) inhibitor or an angiotensin II receptor blocker (ARB).

Also provided herein, in some aspects, are methods comprising:
  a. assaying a biological test sample from a subject to determine an expression level of ROBO2 polypeptide or an RNA encoding a ROBO2 polypeptide;
  b. determining whether the expression level of ROBO2 polypeptide or the expression level of the RNA encoding a ROBO2 polypeptide in the biological test sample is above a reference threshold level; and
  c. diagnosing the subject as in need of treatment or therapy for chronic kidney disease.

In some embodiments of these methods and all such methods described herein, assaying the expression level of ROBO2 polypeptide is performed using an antibody or antigen-binding fragment thereof specific for the ROBO2 polypeptide.

In some embodiments of these methods and all such methods described herein, assaying the expression level of the RNA encoding a ROBO2 polypeptide is performed using PCR or a hybridization assay.

In some embodiments of these methods and all such methods described herein, the biological test sample is a kidney biopsy, urine, blood, serum sample, or cells pelleted from a urine sample.

In some embodiments of these methods and all such methods described herein, the expression level of ROBO2 polypeptide or the expression level of the RNA encoding a ROBO2 polypeptide is at least 20% above the reference threshold level.

In some embodiments of these methods and all such methods described herein, the expression level of ROBO2 polypeptide or the expression level of the RNA encoding a ROBO2 polypeptide is at least two standard deviations above the reference threshold level.

Also provided herein, in some aspects, are assays comprising:
  a. contacting a biological test sample isolated from a subject with a reagent that detects ROBO2 polypeptide or an RNA encoding a ROBO2 polypeptide; and
  b. measuring the level of ROBO2 polypeptide or an RNA encoding a ROBO2 polypeptide, wherein an increased level of said ROBO2 polypeptide or said RNA encoding a ROBO2 polypeptide, relative to a normal biological sample, identifies a subject having chronic kidney disease and/or progression of chronic kidney disease or proteinuria.

In some embodiments of these assays and all such assays described herein, detecting the expression level of ROBO2 polypeptide is performed using an antibody or antigen-binding fragment thereof specific for the ROBO2 polypeptide.

In some embodiments of these assays and all such assays described herein, detecting the expression level of the RNA encoding a ROBO2 polypeptide is performed using PCR or a hybridization assay.

In some embodiments of these assays and all such assays described herein, the biological test sample is a kidney biopsy, urine, blood, serum sample, or cells pelleted from a urine sample.

In some embodiments of these assays and all such assays described herein, the expression level of ROBO2 polypeptide or the expression level of the RNA encoding a ROBO2 polypeptide is at least 20% above the reference threshold level.

In some embodiments of these assays and all such assays described herein, the expression level of ROBO2 polypeptide or the expression level of the RNA encoding a ROBO2 polypeptide is at least two standard deviations above the reference threshold level.

In some embodiments of these assays and all such assays described herein, the subject has been diagnosed with diabetes or high blood pressure.

In some aspects, provided herein are systems for determining if a subject is at risk for chronic kidney disease or proteinuria, or has chronic kidney disease comprising:
   a. a measuring module configured to determine the expression level of ROBO2 polypeptide or the expression level of the RNA encoding a ROBO2 polypeptide in a biological sample obtained from a subject;
   b. a comparison module configured to receive said expression level of ROBO2 polypeptide or the expression level of the RNA encoding a ROBO2 polypeptide determined by the measuring module and perform at least one analysis to determine whether the expression level of ROBO2 polypeptide or the expression level of the RNA encoding a ROBO2 polypeptide is greater than a pre-determined reference level or ratio, and to provide a retrieved content; and
   c. a display module for displaying a content based the data output from said comparison module, wherein the content comprises a signal indicative that the expression level or ratio of ROBO2 polypeptide or RNA is greater than the pre-determined reference level or ratio, or a signal indicative that the level or expression ratio of ROBO2 is not greater than the reference level or pre-determined ratio.

In some embodiments of these systems and all such systems described herein, the content displayed on the display module further comprises a signal indicative of the subject being recommended to receive a particular treatment regimen.

In some aspects, provided herein are systems for determining if a subject is at risk for chronic kidney disease or proteinuria, or has chronic kidney disease comprising:
   a. a determination module configured to receive at least one test sample obtained from a subject and perform at least one analysis on said at least one test sample to determine the presence or absence of either of the following conditions:
      i. an expression ratio of ROBO2 greater than a pre-determined ratio, or
      ii. an expression level of ROBO2 greater than a pre-determined level
   b. a storage device configured to store data output from said determination module; and
   c. a display module for displaying a content based on the data output from said determination module, wherein the content comprises a signal indicative that the expression ratio of ROBO2 is greater than the pre-determined ratio or level of ROBO2 greater than a pre-determined level, or a signal indicative that the expression ratio of ROBO2 is not greater than the pre-determined ratio or not greater than a pre-determined level.

In some embodiments of these systems and all such systems described herein, the content displayed on the display module further comprises a signal indicative of the subject being recommended to receive a particular treatment regimen.

Also provided herein, in some aspects, are methods for treating a human subject with a risk of chronic kidney disease or proteinuria, comprising administering a treatment or therapy to prevent the occurrence of chronic kidney disease or proteinuria to a human subject who is determined to have a level of ROBO2 protein above a reference threshold level.

In some embodiments of these methods and all such methods described herein, the level of ROBO2 protein is at least 20% above the reference level.

In some embodiments of these methods and all such methods described herein, the level of ROBO2 protein is at least two standard deviations above the reference level.

In some embodiments of these methods and all such methods described herein, the treatment or therapy to prevent the occurrence of chronic kidney disease or proteinuria comprises a ROBO2 inhibitor.

In some embodiments of these methods and all such methods described herein, the ROBO2 inhibitor is a blocking antibody or antigen-binding fragment thereof specific for ROBO2, an antisense molecule specific for ROBO2, a short interfering RNA (siRNA) specific for ROBO2, a small molecule inhibitor of ROBO2, a ROBO2 inhibitory polypeptide, or a ROBO2 structural analog.

In some embodiments of these methods and all such methods described herein, ROBO2 inhibitor blocks or reduces binding of ROBO2 to SLIT, to Nck, or to both.

In some embodiments of these methods and all such methods described herein, the ROBO2 inhibitor is specific for the Ig1 SLIT binding domain, the Ig1 and Ig2 SLIT binding domains, the Nck intracellular binding domain, or any combination thereof.

In some embodiments of these methods and all such methods described herein, the ROBO2 inhibitory polypeptide is a dominant negative ROBO2 fusion protein, a polypeptide comprising a ROBO2 extracellular domain without the intracellular domain, or a polypeptide comprising a ROBO2 intracellular domain without the extracellular domain.

Also provided herein, in some aspects, are ROBO2 inhibitors for use in treating a chronic kidney disease, and ROBO2 inhibitor for use in treating proteinuria.

In some embodiments of these uses and all such uses described herein, the ROBO2 inhibitor is a blocking antibody or antigen-binding fragment thereof specific for ROBO2, an antisense molecule specific for ROBO2, a short interfering RNA (siRNA) specific for ROBO2, a small molecule inhibitor of ROBO2, a ROBO2 inhibitory polypeptide, or a ROBO2 structural analog.

In some embodiments of these uses and all such uses described herein, the ROBO2 inhibitor blocks or reduces binding of ROBO2 to SLIT, to Nck, or to both.

In some embodiments of these uses and all such uses described herein, the ROBO2 inhibitor is specific for the Ig1 SLIT binding domain, the Ig1 and Ig2 SLIT binding domains, the Nck intracellular binding domain, or any combination thereof.

In some embodiments of these uses and all such uses described herein, the ROBO2 inhibitory polypeptide is a dominant negative ROBO2 fusion protein, a polypeptide comprising a ROBO2 extracellular domain without the intracellular domain, or a polypeptide comprising a ROBO2 intracellular domain without the extracellular domain.

In some embodiments of these uses and all such uses described herein, the chronic kidney disease or proteinuria is caused by diabetic nephropathy or high blood pressure.

In some embodiments of any of these aspects and all such aspects described herein, ROBO2 refers to human ROBO2 having the amino acid sequence of SEQ ID NO: 1 encoded by the mRNA sequence of SEQ ID NO: 2. In some embodiments of any of these aspects and all such aspects described herein, ROBO2 refers to human ROBO2 having the amino acid sequence of SEQ ID NO: 3 encoded by the mRNA sequence of SEQ ID NO: 4.

DEFINITIONS

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and the include plural references unless the context clearly dictates otherwise. Thus for example, references to "the method" includes one or more methods, and/or steps of the type described herein and/or which will become apparent to those persons skilled in the art upon reading this disclosure and so forth.

Other than in the operating examples, or where otherwise indicated, all numbers expressing quantities of ingredients or reaction conditions used herein should be understood as modified in all instances by the term "about." The term "about" when used in connection with percentages can mean±10%, ±5%, or ±1%.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology, and molecular biology can be found in The Merck Manual of Diagnosis and Therapy, 18th Edition, published by Merck Research Laboratories, 2006 (ISBN 0-911910-18-2); Robert S. Porter et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006. Definitions of common terms in molecular biology are found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl Eds., Academic Press Inc., San Diego, USA (1987); Current Protocols in Molecular Biology (CPMB) (Fred M. Ausubel, et al. ed., John Wiley and Sons, Inc.), Current Protocols in Protein Science (CPPS) (John E. Coligan, et. al., ed., John Wiley and Sons, Inc.) and Current Protocols in Immunology (CPI) (John E. Coligan, et. al., ed. John Wiley and Sons, Inc.), which are all incorporated by reference herein in their entireties.

It is understood that the following detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of

BRIEF DESCRIPTION OF THE DRAWINGS

(FIGS. 1A-1C) Robo2 co-localizes with podocyte slit-diaphragm protein nephrin. (FIG. 1R) Immunogold electron microscopy shows localization of gold partials (arrows) conjugated to Robo2 antibody in the foot process (fp) of a podocyte from a 3-week old mouse. GBM, glomerular basement membrane. Magnification: 50,000×. See also FIGS. 5A-5M.

(FIG. 2A) Yeast two-hybrid assays show a positive interaction between Robo2 intracellular domain (Robo2-ICD) and Nck1. LacZ reporter (X-gal): +++, yeast turned dark; ++, light; −, white in 24 hours. Leucine reporter (−Leu): +, yeast grew; −, yeast did not grow. CC, cytoplasmic conserved region. Numbers indicate residue positions in the full-length protein. (FIG. 2B) Yeast two-hybrid assays show the first two SH3 domains of Nck1 are required for its interaction with Robo2-ICD. (FIG. 2C, FIG. 2C discloses SEQ ID NO: 5) Yeast two-hybrid assays show potential binding domains that mediate Robo2 and Nck1 interaction. The sequence is the potential binding region in Robo2 for Nck1. Proline-rich regions are highlighted. (FIG. 2D) Co-precipitation of Robo2 and Nck. Cell lysates in lane 5 are collected from His-myc-Robo2 transfected cells (used in lanes 1 and 2); Cell lysates in lane 6 are collected from His-myc-Robo2-ANBD transfected cells (used in lanes 3 and 4). (FIG. 2E) Co-precipitation of Robo2, Nck, and nephrin. (FIG. 2F) A similar co-precipitation as (FIG. 2E) except that His-myc-nephrin is pulled-down instead of His-myc-Robo2. (FIG. 2G) Co-immunoprecipitation of kidney endogenous Robo2, Nck, and nephrin. (FIG. 2H) A similar assay as (FIG. 2G) except that precipitates are prepared using mouse anti-nephrin antibody. (I) Slit2 enhances Robo2-Nck-nephrin complex formation. His-myc-Robo2, nephrin, and Fyn are expressed in HEK cells that are stimulated with Slit2 conditioned medium (lanes 1, 3) or control conditioned medium (lane 2, 4). (FIG. 2J) Intensity quantification of (FIG. 2I). Data are represented as mean±SEM; n=7, *p<0.05, **p<0.01 compared with the control, paired student's t-test. See also FIGS. 6A-6I.

(FIG. 3A) CD16/7-NCD is co-expressed with Robo2 in HEK cells, which are treated with anti-CD16 antibody and rhodamine-conjugated anti-IgG antibody in the presence of Slit2 conditioned medium (Slit) or control conditioned medium (CTL). Cells are then fixed and stained with FITC-conjugated phalloidin to reveal F-actin. Scale bar, 5 µm. NCD: nephrin cytoplasmic domain. (FIG. 3B) A similar assay as (FIG. 3A) except that CD16/7-NCD is replaced by CD16/7-HA and is used as a control assay. (FIG. 3C) The percentage of cells with F-actin tails over total cells with CD16/7 clusters in each group is quantified. Data are represented as mean±SEM, *p<0.01, n=5. (FIG. 3D) CD16/7-NCD in (FIG. 3A) is immunoprecipitated by anti-CD16 antibody after Slit2 conditioned medium stimulation (lanes 1 and 3) or control conditioned medium (lanes 2 and 4). Note reduced F-actin in lane 1. CD16/7-HA is used as a negative control. (FIG. 3E) Intensity quantification of (FIG. 3D). Data are represented as mean±SEM; n=4, *p<0.05 compared with the control, paired student's t-test. (FIG. 3F) Immunoprecipitation of nephrin from Robo2 knockout homozygous (Robo2−/−), heterozygous (Robo2+/−), and wild-type (Robo2+/+) mouse kidneys using the anti-nephrin antibody. Note increased F-actin in lane 3. (FIG. 3G) Intensity quantification of (FIG. 3F). Data are represented as mean±SEM; n=4, *p<0.05 compared with the wild-type and heterozygous, ANOVA analysis. See also FIGS. 7A-7C.

FIGS. 4A-4W demonstrate podocyte structural phenotypes in the Robo2 homozygous null, Robo2 podocyte specific knockout, and Robo2 and Nphs1 double knockout mice. (FIGS. 4A and 4B) Representative images of newborn kidneys show podocyte bodies (arrowheads) and Bowman's capsule (arrows) in wild-type (FIG. 4A) and Robo2 homozygous null mice (FIG. 4B). (FIGS. 4C and 4D) High magnification images of (FIGS. 4A and 4B) show podocyte foot processes (arrows) in the newborn kidney. Scale bar, 1 µm. (FIGS. 4E and 4F) Representative images of 3-week kidneys at low magnification show podocyte cell body (arrowheads) in a Robo2 homozygous null mouse (FIG. 4F) compared to an age-matched control (FIG. 4E). (FIGS. 4G and 4H) Higher magnification images of (FIGS. 4E and 4F) show disorganized shorter meandering foot processes (arrow) in a 3-week Robo2 homozygous null mouse (FIG. 4H) compared to well-organized zip-like foot processes in the age-matched control (FIG. 4G). Scale bars: 2 µm. (FIGS. 4I and 4J) Representative transmission electron microscopy images (magnification at 5000×) depict the focal segmental podocyte foot process effacement (arrow in FIG. 4J) in a one month old Robo2 podocyte-specific knockout mouse and the normal phenotype in the control (FIG. 4I). Abbreviations: gc: glomerular capillary; us: urinary space. (FIGS. 4K and 4L) Higher magnification transmission electron microscopy images (40000×) show broader podocyte foot processes (arrow in FIG. 4L) in a two months old Robo2 podocyte-specific mutant mouse compared with the control (FIG. 4K). Abbreviations: fp, podocyte foot process; GBM, glomerular basement membrane. (FIG. 4M) Quantification of podocyte foot process width in one month old Robo2$^{del5/flox}$; Tg$^{Nphs2-Cre+}$ podocyte specific knockout mice (Robo2 KO) and the wild-type littermate controls (WT). Data are represented as mean±SEM, n=333, *p<0.01. (FIG. 4N) ELISA assay of spot urine shows an elevated albumin/creatinine ratio in Robo2$^{del5/flox}$; Nphs2-Cre+ (KO) adult mice compared with control wild-type (WT). Data are represented as mean±SEM, n=20, *p<0.01. (FIG. 4O) Western blot analysis shows the presence of albumin in urine; 1 µl urine was loaded on each well, 0.2 µg albumin was used as a positive control. WT, three wild-type littermates; Robo2 KO, three individual Robo2del5/flox; Nphs2-Cre+ mice. (FIGS. 4V and 4W), Glomeruli from newborn wild type mice with normal regular interdigitating pattern of the foot process (arrows). See also FIGS. 8A-8Z and Tables 1-4.

(FIGS. 5A and 5B) In situ hybridization analysis shows that Robo2 transcripts are expressed in developing glomeruli (arrows) at E16.5. Magnification: 60× (FIG. 5A) and 200× (FIG. 5B). (FIGS. 5C-5F) Immunohistochemistry (IHC) studies reveal that Robo2 is expressed during developing glomeruli from E14.5 to E17.5. Magnification: 600×. (FIG. 5G) IHC shows that Robo2 is specifically expressed in adult mouse glomeruli at 5 weeks of age (FIG. 5G). DAPI marks cell nuclei in the kidney. Magnification: 400×. (FIG. 5H) IHC co-localization stainings of 5 w kidney show Robo2 is co-expressed in the glomerulus with podocyte marker Wt1. Magnification: 600×. (FIGS. 5I-5K) Robo2 and WT1 are co-expressed in the mouse glomerulus at E16.5. Magnification: 600×. (FIGS. 5L and 5M) IHC co-localization stainings of 5 w kidney show Robo2 is co-expressed in the glomerulus with mesangial cell marker Pdgfrb (FIG. 5L), and endothelial cell marker Pecam1 (FIG. 5M). Magnification: 600×.

FIGS. 6A-6I demonstrate that Robo2 interacts with Nck and forms a complex with nephrin, which is enhanced by Slit2 stimulation. (FIG. 6A) Co-IP of Robo2 and nephrin with endogenous Nck. Robo2, nephrin, and Fyn are expressed in HEK cells and stimulated by Slit2. The endogenous Nck is immunoprecipitated by an anti-Nck antibody. The mouse IgG is used as a control. The complex formation with nephrin is enhanced by Slit2 and Fyn expression. (FIGS. 6B and 6C) Slit2 is expressed in the newborn mouse glomeruli by Immunoperoxidase staining (FIG. 6B) and is co-expressed in the glomerulus with the podocyte marker Synaptopodin (FIG. 6C). Magnification: 600×. (FIGS. 6D and 6E) CD16/7-NCD is co-expressed with Robo2 in HEK cells in the presence of Slit2, treated with anti-CD16 antibody and rhodamine-conjugated anti-IgG antibody, then fixed and stained with anti-Robo2 antibody. CD16/7-NCD clusters co-localize with Robo2 (FIG. 6D) but no colocalization is observed in control CD16/7-HA clusters (FIG. 6E). Scale bar: 5μπι. NCD: nephrin cytoplasmic domain. (FIGS. 6F and 6G) Deletion of Nck binding domain (NBD) in Robo2 impairs its co-localization with CD16/7-NCD in the presence of Slit2. CD 16/7-NCD clusters co-localize with Robo2 (FIG. 6F) but no colocalization is observed in Robo2-ΔNBD clusters (FIG. 6G). Scale bar: 5μπι. (FIGS. 6H and 6I) Slit2 stimulation enhances CD16/7-NCD and Robo2 co-localization in HEK cells. CD 16/7-NCD clusters co-localize with Robo2 in the presence of Slit2 (FIG. 6H) but not with control conditioned medium (FIG. 6I). Scale bar: 5μπι.

FIGS. 7A-7C demonstrate deletion of Nck binding domain in Robo2 compromises Slit2-Robo2 inhibition on nephrin-induced actin polymerization. (FIG. 7A) CD16/7-NCD and Robo2 were co-expressed in HEK cells, clustered with anti-CD16 antibody and rhodamine-conjugated anti-IgG antibody in the presence of Slit2 conditioned medium (Slit2) or control conditioned medium (CTL). Cells were then fixed and stained with FITC-conjugated phalloidin to reveal F-actin fibers. Clusters of CD16/7-NCD and F-actin fibers were examined using confocal microscopy. Scale bar, 5 μm. NCD, nephrin cytoplasmic domain. (FIG. 7B) CD16/7-NCD and Robo2-ΔNBD were co-expressed in HEK cells. Scale bar, 5 μm. NBD, Nck binding domain. (FIG. 7C) The percentage of cells with F-actin tails over total cells with CD16/7-NCD clusters in each group was quantified. Data are represented as mean±SEM, *p=1.436×10$^{-5}$, **p=6.32× 10$^{-5}$, n=5, ANOVA.

FIGS. 8A-8Z demonstrate glomerular phenotype in the Robo2 homozygous null, Robo2 podocyte specific knockout, Robo2 and Nphs1 double knockout mice, and a proposed model of Robo2-Nephrin signaling. (FIGS. 8A-8F) Transmission electron microscopy analysis of glomerular ultrastructure in newborn (NB) Robo2$^{del5/del5}$ mutant mice kidney. (FIGS. 8A, 8C, 8E) Glomerular ultrastructure from a newborn heterozygous Robo2 control mouse at low (FIG. 8A, 2200×), medium (FIG. 8C, 15500×) and high (FIG. 8E, 52000×) magnifications. (FIGS. 8B, 8D, 8F) Glomerular ultrastructure from a newborn homozygous Robo2 (−/−) (i.e., Robo2$^{del5/del5}$) mutant mouse at low (FIG. 8B), medium (FIG. 8D) and high (FIG. 8F) magnifications. Arrows indicate focal foot process effacement. Abbreviations: gc: glomerular capillary; us: urinary space; GBM: glomerular basement membrane. (FIGS. 8G-8J) Representative scanning electron microscopy images of glomeruli from one-month old Robo2$^{del5/flox}$; Nphs2-Cre$^+$ podocyte-specific knockout mice and aged matched Robo2$^{flox/+}$ control mice. Mild irregularities of the interdigitating podocyte foot processes were found in a one month old Robo2 podocyte-specific knockout mouse (FIGS. 8K and 8N). At seven months old, Robo2 podocyte-specific knockout mice developed markedly irregular foot processes (FIGS. 8L and 8N). Scale bars: 10 μm (FIGS. 8G, 8H, 8K, 8L at 2000× magnification) and 2 μm (FIGS. 8I, 8J, 8M, 8N at 13000× magnification). (FIGS. 8O-8R) Periodic acid-Schiff (PAS) staining showed mesangial matrix expansion in the glomeruli from 2-month and 6-month old Robo2 podocyte-specific knockout mice (FIGS. 8P, 8R) compared to age-matched controls (FIGS. 8O, 8Q). (FIG. 8S) Quantitative analysis of glomeruli shows mesangial matrix expansion in 12-month old Robo2 podocyte-specific knockout mice (MU) compared to age matched wild-type (WT) controls. Data are represented as mean±SEM, n=5, *p<0.01. (T) Robo2 podocyte specific knockout does not affect podocyte numbers. Podocyte cells were identified using WT-1 staining. The number of podocytes per glomerular cross section was counted in four one-year old Robo2$^{del5/flox}$; Tg$^{Nphs2-Cre+}$ podocyte specific knockout mice (MU) compared to four age-matched wild-type mice (WT). Data are represented as mean±SEM, p=0.645, t-test; mutant: n=165 glomeruli; control: n=166 glomeruli. (FIG. 8U) H&E staining shows glomeruli with characteristic dilatations of the Bowman's space (asterisks) in a Nphs1$^{-/-}$ single homozygous newborn mouse, 400×. (FIG. 8V) Glomeruli from a Robo2$^{-/-}$ single homozygous newborn mouse show absence of Bowman's space dilatations; 400×. (FIG. 8W) Normal looking glomeruli without significant Bowman's space dilatations (arrows) are shown in a Robo2$^{-/-}$; Nphs1$^{-/-}$ double homozygous newborn mouse indicating alleviation of Nphs1$^{-/-}$ glomerular phenotype; 400×. (FIG. 8X) H&E staining of normal kidney and glomeruli from an age-matched wild-type newborn mouse control; 400×. (FIG. 8Y) Quantification of glomeruli with dilated Bowman's space in newborn mice show significant reduction of glomeruli with the characteristic dilatation phenotype of the Bowman's space in Robo2$^{-/-}$; Nphs1$^{-/-}$ double homozygous compared to Nphs1$^{-/-}$ single homozygous (Robo2$^{+/-}$; Nphs1$^{-/-}$). Data are represented as mean±SEM, *p<0.01. (FIG. 8Z) A model of inhibitory effects of Slit2-Robo2 signaling on nephrin to influence podocyte foot process structure: Under physiological conditions (e.g., during foot process development), nephrin intracellular phosphorylated tyrosine domains (YDxV-p) recruit Nck through its interaction with the SH2 domain. Nck in turn recruits cytoskeleton regulators through its SH3 domains to promote actin polymerization. Slit2 binds Robo2 to increase Robo2 intracellular domain interaction with SH3 domains of Nck, which would prevent binding of Nck to cytoskeletal regulators and result in an inhibition of nephrin-induced actin polymerization. Balanced actin polymerization is maintained during podocte development for a normal foot process structure. In the absence of Slit2-Robo2 signaling (e.g., when Robo2 is knocked out), the inhibitory effects of Robo2 on nephrin induced polymerization is lost. The SH3 domains of Nck are able to interact with downstream cytoskeletal regulators to increase actin polymerization, which may explain the altered podocyte foot process structure in Robo2 mutant mice. Abbreviations: Ig: Immunoglobulin domain; FN3: Fibronectin type 3 domain; SH2: Src homolog 2 domain; SH3: Src homolog 3 domain; CC0, CC1, CC2, CC3: Cytoplasmic Conserved region 0, 1, 2, 3.

DETAILED DESCRIPTION

Figure 1A:
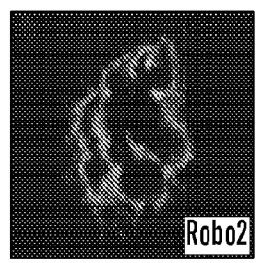
FIGS. 1A-1R demonstrate that Robo2 is expressed and localized to the basal cell surface of podocytes. All immunostainings in (FIGS. 1A-1Q) are performed at mouse E16.5 days at 600× magnification (see FIGS. 5A-5M for immunostainings in adult mouse glomeruli).

Robo2 has been previously shown to be the cell surface receptor for the repulsive guidance cue Slit and to be involved in axon guidance and neuronal migration in the nervous system. Nephrin is a podocyte slit-diaphragm protein that functions in the kidney glomerular filtration barrier. We demonstrate herein that Robo2 is expressed at the basal surface of podocytes, such as mouse podocytes, and co-localizes with nephrin. Biochemical studies indicate that Robo2 forms a complex with nephrin in the kidney through adaptor protein Nck. In contrast to the role of nephrin that promotes actin polymerization, we show herein that Slit2-Robo2 signaling inhibits nephrin-induced actin polymerization. For example, the amount of F-actin associated with nephrin is increased in Robo2 knockout mice that develop an altered podocyte foot process structure and microalbuminuria. Genetic interaction studies further reveal that loss of Robo2 alleviates the abnormal podocyte phenotype in nephrin null mice. The results provided herein show that Robo2 signaling acts as a negative regulator on nephrin to influence podocyte foot process architecture.

In addition, it has been shown that a patient having vesicoureteral reflux (VUR) has a chromosome translocation that disrupts the ROBO2 gene and produces dominant negative ROBO2 fusion proteins that abrogate the SLIT2-ROBO2 signaling pathway. Normally, VUR is a disease characterized by the retrograde flow of urine from the bladder into the ureters and kidney and VUR patients can present with reflux nephropathy, a condition that manifests with severe proteinuria. It has been shown that dominant negative ROBO2 fusion proteins produced by a VUR patient blocks the SLIT2-ROBO2 signaling pathway and protects the patient from reflux nephropathy and proteinuria, thus confirming and further supporting the inventors results in animal models of the therapeutic value of targeting the SLIT2-ROBO2 signaling pathway for the treatment of chronic kidney disease.

In the normal kidney, the trilaminar glomerular capillary wall, composed of fenestrated endothelial cells, basement membrane and podocytes, restricts the permeability to plasma proteins. Podocytes are specialized epithelial cells that extend primary and secondary processes to cover the outer surface of the glomerular basement membrane. The actin-rich interdigitating secondary processes, or foot processes, from neighboring podocytes create filtration slits bridged by a semi-porous slit-diaphragm that forms the final barrier to protein permeation. Whereas genetic mutations of podocyte slit-diaphragm proteins such as nephrin and others are associated with hereditary forms of proteinuric kidney disease (Tryggvason et al., 2006), it has become evident that the proteins that make up and associate with the slit-diaphragm are more than a simple structural barrier. These proteins form a balanced signaling network that can influence podocyte foot process structure and function through interaction with the F-actin cytoskeleton (Faul et al., 2007; Jones et al., 2006; Verma et al., 2006).

Roundabout (Robo) family proteins, Robo1, Robo2, Robo3 and Robo4 are cell surface receptors for the secreted ligand Slit (Dickson and Gilestro, 2006). Slit1, Slit2, and Slit3 were originally found as repulsive guidance cues for axon pathfinding and migrating neurons during nervous system development (Guan and Rao, 2003). The transmembrane protein Robo contains five Ig motifs and three fibronectin type III (FNIII) repeats in its extracellular domain (Dickson and Gilestro, 2006). While both immunoglobulin (Ig) motifs 1 and 2 interact with Slit, the first Ig1 motif of Robo is the primary binding site for Slit (Dickson and Gilestro, 2006). The intracellular domain of Robo has four cytoplasmic conserved (CC) sequences named CC0, CC1, CC2, and CC3 (Bashaw et al., 2000; Kidd et al., 1998; Morlot et al., 2007; Zallen et al., 1998). CC0 and CC1 contain tyrosine, while CC2 and CC3 are proline-rich stretches. The repulsive activity of Slit-Robo signaling inhibits actin polymerization (Guan and Rao, 2003) or induces F-actin depolymerization (Piper et al., 2006).

Slit-Robo signaling also plays crucial roles during early kidney induction and ureteric bud outgrowth. Mouse mutants that lack Slit2 or Robo2 develop supernumerary ureteric buds, which lead to a broad-spectrum of urinary tract phenotype including duplex kidneys, abnormal ureterovesical junctions and hydronephrosis (Grieshammer et al., 2004; Lu et al. 2007). Disruption of ROBO2 in humans causes congenital anomalies of the kidneys and urinary tracts (CAKUT), and point mutations of ROBO2 have been identified in patients with vesicoureteral reflux (VUR) (Lu et al., 2007). Our recent study demonstrates that Robo2 is crucial for the formation of a normal ureteral orifice and for the maintenance of an effective anti-reflux mechanism (Wang et al., 2011).

Herein we demonstrate that Robo2 is a novel podocyte protein expressed at the basal surface of glomerular podocytes in the kidney and is co-localized with nephrin and podocin. Robo2 interacts directly with adaptor protein Nck SH3 domains and forms a complex with nephrin. Whereas Robo2 knockout mice develop altered podocyte foot processes, the loss of Robo2 alleviates the foot process structural abnormalities that are seen in nephrin null mice. These results described herein indicate that Robo2 signaling acts as a negative regulator on nephrin signaling to influence podocyte foot process architecture. In addition, as demonstrated herein, it has been discovered that the dominant negative ROBO2 fusion proteins produced by a patient blocks the SLIT2-ROBO2 signaling pathway and protects the patient from reflux nephropathy and proteinuria, thus confirming and further supporting the results described herein in animal models of the therapeutic value of targeting the SLIT2-ROBO2 signaling pathway for the treatment of chronic kidney disease.

Accordingly, in some aspects, provided herein are methods for the treatment of chronic kidney disease in a subject in need thereof, such method comprising administering to a subject having or at risk for a chronic kidney disease a therapeutically effective amount of a composition comprising a SLIT2-ROBO2 signaling pathway inhibitor.

Also provided herein, in some aspects, are methods for the reduction of proteinuria in a subject in need thereof, comprising administering to a subject having or at risk for proteinuria a therapeutically effective amount of a composition comprising a SLIT2-ROBO2 signaling pathway inhibitor.

In other aspects, provided herein are methods for preventing kidney diseases or promoting prophylaxis of kidney diseases in a subject in need thereof, comprising administering to a subject a therapeutically effective amount of a composition comprising a SLIT2-ROBO2 signaling pathway inhibitor so as to prevent or promote prophylaxis of kidney disease in the subject.

Also provided herein, in some aspects, are methods for mitigating the effects of kidney disease, reducing the severity of kidney disease, reducing the likelihood of developing kidney disease and/or slowing the progression of kidney disease in a subject in need thereof.

As used herein, "ROBO2" refers to the polypeptide having the amino acid sequence of: MARRHERVTRRM-WTWAPGLLMMTVVFWGHQGNGQGQGSRLRQEDF-PPRIVEHPSDVIVSK GEPTTLNCKAEGRPTP-TIEWYKDGERVETDKDDPRSHRMLLPSGSLFFLRIVH GRRSKPDEGS YVCVARNYLGEAVSRNASLEVALL-RDDFRQNPTDVVVAAGEPAILECQPPRGHPEP-TIYWKK DKVRIDDKEERISIRGGKLMISNTRKSDAG-MYTCVGTNMVGERDSDPAELTVFERPTFLRRPI NQVVLEEEAVEFRCQVQGDPQPTVRWKKDDADL-PRGRYDIKDDYTLRIKKTMSTDEGTYM CIAENRVG-KMEASATLTVRAPPQFVVRPRDQIVAQGRTVTFP-CETKGNPQPAVFWQKEGSQ NLLFPNQPQQPNSRCSVSPTGDLTITNIQRSDAGYYIC QALTVAGSILAKAQLEVTDVLTDRPP PIILQGPANQT-LAVDGTALLKCKATGDPLPVISWLKE GFTFPGRD-PRATIQEQGTLQIKNLRIS DTGTYTCVATSSS-GETSWSAVLDVTESGATISKNYDLSDLPGPPSKPQVT DVTKNSVTLSWQ PGTPGTLPASAYIIEAFSQSV SNSWQTVANHVKTTLYTVRGLRPNTIYLFMVRAIN-PQGLSDPS PMSDPVRTQDISPPAQGVDHRQVQKEL-GDVLVRLHNPVVLTPTTVQVTWTVDRQPQFIQGY RVMYRQTSGLQATSSWQNLDAKVPTERSAVLVNLK-KGVTYEIKVRPYFNEFQGMDSESKTV RTTEEAPS APPQSVTVLTVGSYNSTSISVSWDPPPPDHQNGI-IQEYKIWCLGNETRFHINKTVD AAIRSVIIGGLF-PGIQYRVEVAASTSAGVGVKSEPQP IIIGRRNEV-VITENNNSITEQITDVVKQP AFIAGIGGACWVILMGFSIWLYWRRKKRKGL-SNYAVTFQRGDGGLMSNGSRPGLLNAGDPS YPW-LADSWPATSLPVNNSNSGPNEIGNFGRGDVLP-PVPGQGDKTATMLSDGAIYSSIDFTTKT SYNSSSQITQATPYATTQILHSNSIHELAVDLPD-PQWKSSIQQKTDLMGFGYSLPDQNKGNNG GKGGK-KKKNKNSSKPQKNNGSTWANVPLPPPPVQ-PLPGTELEHYAVEQQENGYDSDSWCPP LPVQTYLHQGLEDELEEDDDRVPTPPVRGVASSPAIS-FGQQSTATLTPSPREEMQPMLQAHLD ELTRAYQFDI-AKQTWHIQSNNQPPQPPVPPLGYVSGALISDLETD-VADDDADDEEEALEIPRP LRALDQTPGSSMDNLDSSVTGKAFTSSQR-PRPTSPFSTDSNTSAALSQSQRPRPTKKHKGGRM DQQPALPHRREGMTDEEALVPYSKPSFPSPGGHSSS-GTASSKGSTGPRKTEVLRAGHQRNAS DLLDIGYMG-SNSQGQFTGEL (Homo sapiens roundabout homolog 2 isoform ROBO2a; SEQ ID NO: 1), as described by, e.g., NP_001122401.1 and encoded by NM_001128929.2 (SEQ ID NO: 2); or MSLLMFTQLLLCGFLYVRVDGSRL-RQEDFPPRIVEHPSDVIVSKGEPTTLNCKAEGRPTP-TIE WYKDGERVETDKDDPRSHRMLLPSGSLFFL-RIVHGRRSKPDEGSYVCVARNYLGEAVSRNA SLEVALLRDDFRQNPTDVVVAAGEPAILECQP-PRGHPEPTIYWKKDKVRIDDKEERISIRGGK LMISN-TRKSDAGMYTCVGTNMVGERDSDPAELTVFERPT-FLRRPINQVVLEEEAVEFRCQVQ GDPQPTVRWKKDDADLPRGRYDIKDDYTLRIKKTM-STDEGTYMCIAENRVGKMEASATLTV RAPPQFVVR-PRDQIVAQGRTVTFPCETKGNPQPAVFWQKEGSQN-LLFPNQPQQPNSRCSVSP TGDLTITNIQRSDAGYYICQALTVAGSILAKAQLEVT DVLTDRPPPIILQGPANQTLAVDGTAL LKCKATGD-PLPVISWLKEGFTFPGRDPRATIQEQGTL QIKNLRIS-DTGTYTCVATSSSGETSWS AVLDVTESGATISKNY-DLSDLPGPPSKPQVTDVTKNS VTLSWQPGTPGTLPASAYIIEAFSQSV SNSWQTVAN-HVKTTLYTVRGLRPNTIYLFMVRAINPQGLS-DPSPMSDPVRTQDISPPAQGVD HRQVQKELGDV-LVRLHNPVVLTPTTVQVTWTVDRQPQFIQGYRVMYR QTSGLQATSSWQN LDAKVPTERSAVLVNLKKGV-TYEIKVRPYFNEFQGMDSESKTVRTTEEAPSAPPQS-VTVLTV GSYNSTSISVSWDPPPPDHQNGIIQEYKIW-CLGNET RFHINKTVDAAIRSVIIGGLFPGIQYRVE VAASTSAGVGVKSEPQPIIIGRRNEVVITENNNSITE QITDVVKQPAFIAGIGGACWVILMGFSI WLYWRRK-KRKGLSNYAVTFQRGDGGLMSNGSRPGLL-NAGDPSYPWLADSWPATSLPVNNS NSGPNEIGNF-GRGDVLPPVPGQGDKTATMLSDGAIY SSIDFTTKTSYNSSSQITQATPYATTQI LHSNSI-HELAVDLPDPQWKSSIQQKTDLMGFGYSLPDQNK-GNNGGKGGKKKKNKNSSKPQK NNGSTWANVPLPP-PPVQPLPGTELEHYAVEQQENGYDSDSWCPPLPVQT YLHQGLEDELEED DDRVPTPPVRGVASSPAISF-GQQSTATLTPSPREEMQPMLQAHLDELTRAYQFDI-AKQTWHIQ SNNQPPQPPVPPLGYVSGALISDLETD-VADDDADDEEEALEIPRPLRALDQTPGSSMDNLDSS VTGKAFTSSQRPRPTSPFSTDSNTSAALSQSQRPRPT-KKHKGGRMDQQPALPHRREGMTDEE ALVPYSKPS-FPSPGGHSSSGTASSKGSTGPRKTEVLRAGHQRNAS-DLLDIGYMGSNSQGQFTG EL (Homo sapiens roundabout homolog 2 isoform ROBO2b; SEQ ID NO: 3), as described by, e.g., NP_002933.1 and encoded by NM_002942.4 (SEQ ID NO: 4) together with any naturally occurring allelic, splice variants, and processed forms thereof. Typically, ROBO2 refers to human ROBO2. The ROBO2 gene is conserved in chimpanzee, Rhesus monkey, dog, cow, mouse, rat, chicken, zebrafish, fruit fly, mosquito, and C. elegans. Specific residues of ROBO2 can be referred to as, for example, "ROBO2(30)."

Specific domains of ROBO2 can be referred to by such nomenclature as well. The N-terminal or "extracellular domain of ROBO2", comprising the five immunoglobulin motifs and three fibronectin type III (FNIII) repeats can be referred to as ROBO2(46-848) of SEQ ID NO: 1 or ROBO2 (30-832) of SEQ ID NO: 3, for example. The immunoglobulin (Ig) motifs 1 and 2 that interact with Slit2, or the "Ig SLIT binding domain" can be referred to as ROBO2(46-145) and ROBO2(151-237) respectively of SEQ ID NO: 1, and ROBO2(30-129) and ROBO2(135-221) respectively of SEQ ID NO: 3. Similarly, the "intracellular domain" comprising the "Nck intracellular binding domain," which comprises the four intracellular proline rich motifs, described herein, can be referred to as ROBO2(881-1378) of SEQ ID NO: 3.

As used herein, the terms "ROBO2 inhibitor," "ROBO2 antagonist," "ROBO2 inhibitor agent," and "ROBO2 antagonist agent" refer to a molecule or agent that significantly blocks, inhibits, reduces, or interferes with ROBO2 (mammalian, such as human, ROBO2) biological activity in vitro, in situ, and/or in vivo, including activity of downstream pathways mediated by ROBO2 signaling, such as, for example, ROBO2 interaction with the adaptor protein Nck and/or complex formation with nephrin, SLIT2-ROBO-2 mediated inhibition of nephrin-mediated actin polymerization, and/or elicitation of a cellular response to ROBO2. The term "agent" as used herein in reference to a ROBO2 inhibitor means any compound or substance such as, but not limited to, a small molecule, nucleic acid, polypeptide, peptide, drug, ion, etc. An "agent" can be any chemical, entity, or moiety, including, without limitation, synthetic and naturally-occurring proteinaceous and non-proteinaceous entities. In some embodiments of the aspects described herein, an agent is a nucleic acid, a nucleic acid analogue, a protein, an antibody, a peptide, an aptamer, an oligomer of nucleic acids, an amino acid, or a carbohydrate, and includes, without limitation, proteins, oligonucleotides, ribozymes, DNAzymes, glycoproteins, antisense RNAs, siRNAs, lipoproteins, aptamers, and modifications and combinations thereof etc. Compounds for use in the therapeutic compositions and methods described herein can be known to have a desired activity and/or property, or can be selected from a library of diverse compounds, using screening methods known to one of ordinary skill in the art.

Exemplary ROBO2 inhibitors contemplated for use in the various aspects and embodiments described herein include, but are not limited to, anti-ROBO2 antibodies or antigen-binding fragments thereof that specifically bind to ROBO2; anti-sense molecules directed to a nucleic acid encoding ROBO2 (e.g., ROBO2a or ROBO2b or both); short interfering RNA ("siRNA") molecules directed to a nucleic acid encoding ROBO2 (e.g., ROBO2a or ROBO2b or both); RNA or DNA aptamers that bind to ROBO2, and inhibit/reduce/block ROBO2 mediated signaling; ROBO2 structural analogs; and soluble ROBO2 proteins, inhibitory polypeptides, e.g., dominant negative polypeptides, or fusion polypeptides thereof. In some embodiments of these aspects and all such aspects described herein, a ROBO2 inhibitor (e.g., an antibody or antigen-binding fragment thereof) binds (physically interacts with) ROBO2, targets downstream ROBO2 signaling, and/or inhibits (reduces) ROBO2 synthesis, production or release. In some embodiments of these aspects and all such aspects described herein, a ROBO2 inhibitor binds and prevents its binding a SLIT protein ligand, such as SLIT2. In some embodiments of these aspects and all such aspects described herein, a ROBO2 inhibitor specifically reduces or eliminates expression (i.e., transcription or translation) of one or more ROBO2 isoforms.

As used herein, a ROBO2 inhibitor or antagonist has the ability to reduce the activity and/or expression of ROBO2 in a cell (e.g., podocytes) by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, or more, relative to the activity or expression level in the absence of the ROBO2 inhibitor.

Accordingly, in some embodiments of the compositions and methods described herein, the ROBO2 inhibitor inhibits ROBO2 mediated signal transduction. In some embodiments of the compositions and methods described herein, the ROBO2 inhibitor targets ROBO2 interaction with the adaptor protein Nck and/or complex formation with nephrin, SLIT2-ROBO-2 mediated inhibition of nephrin-mediated actin polymerization, and/or elicitation of a cellular response to ROBO2.

In some embodiments of the compositions and methods described herein, the binding sites of the ROBO2 inhibitors, such as an antibody or antigen-binding fragment thereof, are directed against a ROBO2 ligand interaction site, such as a SLIT2 ligand interaction site. In some embodiments of the compositions and methods described herein, the binding sites of the ROBO2 inhibitor, such as an antibody or antigen-binding fragment thereof, are directed against a ROBO2 adaptor interaction site such as an Nck interaction site or the NCK intracellular binding domain comprising the four intracellular proline rich motifs of ROBO2. In some embodiments of the compositions and methods described herein, the binding sites of the ROBO2 inhibitors are directed against a site on a target in the proximity of the ligand interaction site, in order to provide steric hindrance for the interaction of the receptor (e.g., ROBO2) with its ligand (e.g., SLIT2). By binding to a ROBO2 ligand interaction site, a ROBO2 inhibitor described herein can reduce or inhibit the activity or expression of ROBO2, and downstream ROBO2 signaling consequences (e.g., ROBO2 interaction with the adaptor protein Nck and/or complex formation with nephrin, SLIT2-ROBO-2 mediated inhibition of nephrin-mediated actin polymerization, and/or elicitation of a cellular response to ROBO2). For example, in some embodiments of the compositions and methods described herein, the binding sites of the ROBO2 inhibitors block or target at least the Ig1, and preferably both the Ig1 and Ig2 sites, on ROBO2, i.e., ROBO2(46-145) and ROBO2(151-237) respectively of SEQ ID NO: 1, and ROBO2(30-129) and ROBO2(135-221) respectively of SEQ ID NO: 3, for example. In some embodiments of the compositions and methods described herein, the binding sites of the ROBO2 inhibitors block or target the ROBO2 intracellular domain comprising the Nck intracellular binding domain, i.e., ROBO2(881-1378) of SEQ ID NO: 3. In some embodiments of the compositions and methods described herein, the binding sites of the ROBO2 inhibitors block or target the ROBO2 Nck intracellular binding domain comprising the four intracellular proline rich motifs of ROBO2. This can be accomplished by a variety of means well known in the art, such as antibodies and antigen-binding fragments thereof, inhibitor RNAs, etc., and as described herein.

Accordingly, in some embodiments of the compositions and methods described herein, the ROBO2 inhibitor is an antibody or antigen-binding fragment thereof that selectively binds or physically interacts with ROBO2. In some embodiments of the compositions and methods described herein, the ROBO2 inhibitor is an antibody or antigen-binding fragment thereof that binds to ROBO2 and inhibits and/or blocks and/or prevents interaction with Nck and/or complex formation with nephrin. In some embodiments of the compositions and methods described herein, the antibody or antigen-binding fragment thereof binds to the Ig SLIT binding domain of ROBO2. In some embodiments of the compositions and methods described herein, the antibody or antigen-binding fragment thereof binds to the Ig1SLIT binding domain of ROBO2 or both the Ig1 and Ig2 SLIT binding domains of ROBO2, i.e., ROBO2(46-145) and ROBO2(151-237) respectively of SEQ ID NO: 1, and ROBO2(30-129) and ROBO2(135-221) respectively of SEQ ID NO: 3. In some embodiments of the compositions and methods described herein, the antibody or antigen-binding fragment thereof binds to or blocks the ROBO2 intracellular domain, i.e., ROBO2(881-1378) of SEQ ID NO: 3. In some embodiments of the compositions and methods described herein, the antibody or antigen-binding fragment thereof binds to or blocks the Nck intracellular binding domain comprising the four intracellular proline rich motifs of ROBO2.

Antibodies specific for or that selectively bind ROBO2, suitable for use in the compositions and for practicing the methods described herein are preferably monoclonal, and can include, but are not limited to, human, humanized or chimeric antibodies, comprising single chain antibodies, Fab fragments, F(ab') fragments, fragments produced by a Fab expression library, and/or binding fragments of any of the above. Antibodies also refer to immunoglobulin molecules and immunologically active portions of immunoglobulin molecules, i.e., molecules that contain antigen or target binding sites or "antigen-binding fragments." The immunoglobulin molecules described herein can be of any type (e.g., IgG, IgE, IgM, IgD, IgA and IgY), class (e.g., IgG1, IgG2, IgG3, IgG4, IgA1 and IgA2) or subclass of immunoglobulin molecule, as is understood by one of skill in the art.

Accordingly, in some embodiments of the compositions and methods described herein, a ROBO2 inhibitor as described herein is a monoclonal anti-ROBO2 antibody or antigen-binding fragment.

In some embodiments of the compositions and methods described herein, a ROBO2 inhibitor as described herein is a ROBO2 antibody fragment or antigen-binding fragment. The terms "antibody fragment," "antigen binding fragment," and "antibody derivative" as used herein, refer to a protein fragment that comprises only a portion of an intact antibody, generally including an antigen binding site of the intact antibody and thus retaining the ability to bind antigen. Examples of antibody fragments encompassed by the terms antibody fragment or antigen-binding fragment include: (i) the Fab fragment, having $V_L$, $C_L$, $V_H$ and $C_H1$ domains; (ii) the Fab' fragment, which is a Fab fragment having one or more cysteine residues at the C-terminus of the $C_H1$ domain; (iii) the Fd fragment having $V_H$ and $C_H1$ domains; (iv) the Fd' fragment having $V_H$ and $C_H1$ domains and one or more cysteine residues at the C-terminus of the CH1 domain; (v) the Fv fragment having the $V_L$ and $V_H$ domains of a single arm of an antibody; (vi) a dAb fragment (Ward et al., Nature 341, 544-546 (1989)) which consists of a $V_H$ domain or a $V_L$ domain; (vii) isolated CDR regions; (viii) F(ab')$_2$ fragments, a bivalent fragment including two Fab' fragments linked by a disulphide bridge at the hinge region; (ix) single chain antibody molecules (e.g. single chain Fv; scFv) (Bird et al., Science 242:423-426 (1988); and Huston et al., PNAS (USA) 85:5879-5883 (1988)); (x) "diabodies" with two antigen binding sites, comprising a heavy chain variable domain ($V_H$) connected to a light chain variable domain ($V_L$) in the same polypeptide chain (see, e.g., EP 404,097; WO 93/11161; and Hollinger et al., Proc. Natl. Acad. Sci. USA, 90:6444-6448 (1993)); (xi) "linear antibodies" comprising a pair of tandem Fd segments ($V_H$-$C_H1$-$V_H$-$C_H1$) which, together with complementary light chain polypeptides, form a pair of antigen binding regions (Zapata et al. Protein Eng. 8(10):1057-1062 (1995); and U.S. Pat. No. 5,641,870); and modified versions of any of the foregoing (e.g., modified by the covalent attachment of polyalkylene glycol (e.g., polyethylene glycol, polypropylene glycol, polybutylene glycol) or other suitable polymer).

In some embodiments of the compositions and methods described herein, a ROBO2 inhibitor or antagonist is a chimeric antibody derivative of a ROBO2 antagonist antibody or antigen-binding fragment thereof.

The ROBO2 inhibitor or antagonist antibodies and antigen-binding fragments thereof described herein can also be, in some embodiments, a humanized antibody derivative.

In some embodiments, the ROBO2 inhibitor or antagonist antibodies and antigen-binding fragments thereof described herein include derivatives that are modified, i.e., by the covalent attachment of any type of molecule to the antibody, provided that the covalent attachment does not prevent the antibody from binding to the target antigen, e.g., ROBO2.

In some embodiments of the compositions and methods described herein, completely human antibodies are used, which are particularly desirable for the therapeutic treatment of human patients.

In some embodiments of the compositions and methods described herein, the ROBO2 inhibitor comprises at least one antisense molecule capable of blocking or decreasing the expression of a particular functional ROBO2 by targeting nucleic acids encoding ROBO2, e.g., SEQ ID NO: 2 or SEQ ID NO: 4 or both, or relevant domains thereof. In some embodiments of the compositions and methods described herein, the at least one antisense molecule targets nucleic acids encoding the Ig SLIT binding domain of ROBO2. In some embodiments of the compositions and methods described herein, the at least one antisense molecule targets nucleic acids encoding the Ig1 SLIT binding domain of ROBO2 or both the Ig1 and Ig2 SLIT binding domains of ROBO2. In some embodiments of the compositions and methods described herein, the at least one antisense molecule targets nucleic acids encoding the ROBO2 intracellular domain. In some embodiments of the compositions and methods described herein, the at least one antisense molecule targets nucleic acids encoding the Nck intracellular binding domain comprising the four intracellular proline rich motifs of ROBO2. Methods are known to those of ordinary skill in the art for the preparation of antisense oligonucleotide molecules that will specifically bind ROBO2 mRNA without cross-reacting with other polynucleotides. Exemplary sites of targeting include, but are not limited to, the initiation codon, the 5' regulatory regions, including promoters or enhancers, the coding sequence, including any conserved consensus regions, and the 3' untranslated region. In some embodiment of these aspects and all such aspects described herein, the antisense oligonucleotides are about 10 to about 100 nucleotides in length, about 15 to about 50 nucleotides in length, about 18 to about 25 nucleotides in length, or more. In certain embodiments, the antisense oligonucleotides further comprise chemical modifications to increase nuclease resistance and the like, such as, for example, phosphorothioate linkages and 2'-O-sugar modifications known to those of ordinary skill in the art.

In some embodiments of the compositions and methods described herein, the ROBO2 inhibitor comprises at least one short interfering RNA (siRNA) molecule capable of blocking or decreasing the expression of functional ROBO2 by targeting nucleic acids encoding or both isoforms of ROBO2, e.g., SEQ ID NO: 2 or SEQ ID NO: 4, or relevant domains thereof. In some embodiments of the compositions and methods described herein, the at least one siRNA molecule targets nucleic acids encoding the Ig SLIT binding domain of ROBO2. In some embodiments of the compositions and methods described herein, the at least one siRNA molecule targets nucleic acids encoding the Ig1 SLIT binding domain of ROBO2 or both the Ig1 and Ig2 SLIT binding domains of ROBO2. In some embodiments of the compositions and methods described herein, the at least one siRNA molecule targets nucleic acids encoding the ROBO2 intracellular domain. In some embodiments of the compositions and methods described herein, the at least one siRNA molecule targets nucleic acids encoding the Nck intracellular binding domain comprising the four intracellular proline rich motifs of ROBO2. It is routine to prepare siRNA molecules that will specifically target ROBO2 mRNA without cross-reacting with other polynucleotides. siRNA molecules for use in the compositions and methods described herein can be generated by methods known in the art, such as by typical solid phase oligonucleotide synthesis, and often will incorporate chemical modifications to increase half-life and/or efficacy of the siRNA agent, and/or to allow for a more robust delivery formulation. Alternatively, siRNA molecules are delivered using a vector encoding an expression cassette for intracellular transcription of siRNA.

In some embodiments of the compositions and methods described herein, the ROBO2 inhibitor is an RNA or DNA aptamer that binds to one or more isoforms of ROBO2. In some embodiments of the compositions and methods described herein, a ROBO2 inhibitor or antagonist is an RNA or DNA aptamer that binds or physically interacts with ROBO2, and blocks interactions between ROBO2 and a ligand or adaptor molecule, for example, SLIT2 or Nck, respectively. In some embodiments of the compositions and methods described herein, a ROBO-2 inhibitor or antagonist is an RNA or DNA aptamer that binds or physically interacts with ROBO2, and reduces, impedes, or blocks downstream ROBO2 signaling, such as SLIT2-ROBO-2 mediated inhibition of nephrin-mediated actin polymerization, and/or elicitation of a cellular response to ROBO2. In some embodiments of the compositions and methods described herein, the RNA or DNA aptamer binds to or physically interacts with the Ig SLIT binding domain of ROBO2. In some embodiments of the compositions and methods described herein, the RNA or DNA aptamer binds to or physically interacts with the Ig1SLIT binding domain of ROBO2 or both the Ig1 and Ig2 SLIT binding domains of ROBO2, i.e., ROBO2(46-145) and ROBO2(151-237) respectively of SEQ ID NO: 1, and ROBO2(30-129) and ROBO2(135-221) respectively of SEQ ID NO: 3. In some embodiments of the compositions and methods described herein, the RNA or DNA aptamer binds to or physically interacts with the ROBO2 intracellular domain, i.e., ROBO2 (881-1378) of SEQ ID NO: 3. In some embodiments of the compositions and methods described herein, the RNA or DNA aptamer binds to or physically interacts with or blocks the Nck intracellular binding domain comprising the four intracellular proline rich motifs of ROBO2.

In some embodiments of the compositions and methods described herein, the ROBO2 inhibitor is a small molecule compound or agent that targets or binds to ROBO2, including, but not limited to, small peptides or peptide-like molecules, soluble peptides, and synthetic non-peptidyl organic or inorganic compounds. As used herein, the term "small molecule" refers to a chemical agent which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (e.g., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. Exemplary sites of small molecule binding include, but are not limited to, the portion of ROBO2 that binds to SLIT2 or to the adaptor Nck, i.e., the Ig1SLIT binding domain of ROBO2 or both the Ig1 and Ig2 SLIT binding domains of ROBO2, the ROBO2 intracellular domain or the Nck intracellular binding domain comprising the four intracellular proline rich motifs of ROBO2.

In some embodiments of the compositions and methods described herein, a ROBO2 inhibitor or antagonist comprises a small molecule that binds to ROBO2 and inhibits ROBO2 biological activity.

In some embodiments of the compositions and methods described herein, the ROBO2 inhibitor or antagonist comprises at least one ROBO2 structural analog, such as a dominant negative ROBO2 polypeptide. The term ROBO2 structural analogs, as used herein, refers to compounds that have a similar three dimensional structure as part of that of ROBO2 and which bind to SLIT2 and/or to Nck under physiological conditions in vitro or in vivo, wherein the binding at least partially inhibits a ROBO2 biological activity, such as SLIT2-ROBO2 mediated inhibition of nephrin-mediated actin polymerization, and/or elicitation of a cellular response to ROBO2. Suitable ROBO2 structural analogs can be designed and synthesized through molecular modeling of ROBO2-SLIT2 binding, for example. The ROBO2 structural analogs can be monomers, dimers, or higher order multimers in any desired combination of the same or different structures to obtain improved affinities and biological effects.

In some embodiments of the compositions and methods described herein, a ROBO2 inhibitor or antagonist comprises at least one soluble ROBO2 receptor or fusion polypeptide thereof, such as, for example, a ROBO2 inhibitory polypeptide. In some such embodiments, the ROBO2 inhibitory polypeptide is a dominant negative ROBO2 fusion protein. In some embodiments of the compositions and methods described herein, the ROBO2 inhibitory polypeptide comprises the ROBO2 extracellular domain, for example, the Ig1SLIT binding domain of ROBO2 or both the Ig1 and Ig2 SLIT binding domains of ROBO2, with no intracellular ROBO2 domains.

ROBO2 inhibitors or antagonists for use in the compositions and methods described herein can be identified or characterized using methods known in the art, such as protein-protein binding assays, biochemical screening assays, immunoassays, and cell-based assays, which are well known in the art, including, but not limited to, those described herein in the Examples.

For example, to identify a molecule that inhibits interaction between ROBO2 and its ligand, e.g., SLIT2, binding assays can be used. For example, ROBO2 or SLIT is immobilized on a microtiter plate by covalent or non-covalent attachment. The assay is performed by adding the non-immobilized component (ligand or receptor), which can be labeled by a detectable label, to the immobilized component, in the presence or absence of a test agent. When the reaction is complete, the non-reacted components are removed and binding complexes are detected. If formation of binding complexes is inhibited by the presence of the test agent, the test agent can be deemed a candidate antagonist that inhibits binding between ROBO2 and SLIT2, for example. Cell-based or membrane-based assays can also be used to identify ROBO2 inhibitors. In other embodiments, by detecting and/or measuring levels of ROBO2 gene expression, ROBO2 inhibitor molecules that inhibit ROBO2 gene expression can be tested. ROBO2 gene expression can be detected and/or measured by a variety of methods, such as real time RT-PCR, enzyme-linked immunosorbent assay ("ELISA"), Northern blotting, or flow cytometry, and as known to one of ordinary skill in the art.

Such identified ROBO2 inhibitors can further be tested using in vivo animal models of chronic kidney disease, such as glomerular and interstitial injury models (e.g., animal models of lupus nephritis, including mice of the NZB, (NZB×NZW) F1 hybrid (termed NZB/W), and congenic derivatives thereof, MRL/lpr and BXSB strains), animal models of aging (e.g., aged Sprague Dawley rats and aged C57BL/6 mice); spontaneously hypertensive rats (SHR); Buffalo/mna rats, which are a model of human idiopathic nephrotic syndrome; Munich Wistar Fromter (MWF) rats, which are a genetic model related to a congenital deficit in nephron number being predisposed to the development of hypertension and salt sensitivity in adulthood; primary podocyte-specific genetic FSGS models; HIV-associated nephropathy (HIVAN) transgenic mouse models; animal models of Alport syndrome, which comprise mutations of the α3, α4, or α5 chains of type IV collagen (COL4A3, COL4A4, and COL4A5); immune-induced models, such as the Thy-1 nephritis model, which is an experimental rat model of mesangioproliferative glomerulonephritis (MsPGN), anti-glomerular basement membrane (GBM) models; and non-immune induced models.

As used herein, in regard to a ROBO2 inhibitor, "selectively binds" or "specifically binds" or "specific for" refers to the ability of a ROBO2 inhibitor as described herein, such as, for example, a ROBO2 antagonist antibody or ROBO2 antigen-binding fragment thereof, to bind to a target, i.e., ROBO2, with a $K_D$ $10^{-5}$ M (10000 nM) or less, e.g., $10^{-6}$ M or less, $10^{-7}$ M or less, $10^{-8}$ M or less, $10^{-9}$ M or less, $10^{-10}$ M or less, $10^{-11}$ M or less, or $10^{-12}$ M or less. For example, if a ROBO2 inhibitor/antagonist described herein binds to ROBO2 with a $K_D$ of $10^{-5}$ M or lower, but not to a related molecule, such as, for example, other ROBO family members, then the agent is said to specifically bind ROBO2. Specific binding can be influenced by, for example, the affinity and avidity of, for example, the ROBO2 inhibitor/antagonist antibody or antigen-binding fragment thereof and the concentration of polypeptide agent. The person of ordinary skill in the art can determine appropriate conditions under which the polypeptide agents described herein selectively bind the targets using any suitable methods, such as titration of a polypeptide agent in a suitable cell binding assay.

In regard to the methods of treating chronic kidney disease by inhibiting ROBO2 activity, the term "chronic kidney disease" or CKD refers to renal diseases that slowly and progressively worsen over time due to the progressive loss of nephrons and consequent loss of renal function. In the early stages, there may be no symptoms. The loss of function usually takes months or years to occur. It may be so slow that symptoms do not appear until kidney function is less than one-tenth of normal. The final stage of chronic kidney disease is called end-stage renal disease (ESRD). At this stage, the kidneys are no longer able to remove enough wastes and excess fluids from the body. The patient needs dialysis or a kidney transplant. Diabetes, which leads to diabetic nephropathy, and high blood pressure are the two most common causes of chronic kidney disease and account for most cases. Other diseases and conditions that can damage the kidneys and lead to chronic kidney disease, include: autoimmune disorders (such as systemic lupus erythematosus and scleroderma); birth defects of the kidneys (such as polycystic kidney disease); certain toxic chemicals; glomerulonephritis; injury or trauma; kidney stones and infection; problems with the arteries leading to or inside the kidneys; some pain medications and other drugs (such as cancer drugs); reflux nephropathy (in which the kidneys are damaged by the backward flow of urine into the kidneys); etc. As used herein, "proteinuria" refers to the presence of an excess of serum proteins in the urine. Proteinuria can, in some embodiments, be indicative of kidney disease, but, by itself, is not conclusive.

Accordingly, in some embodiments of these aspects and all such aspects described herein, the subject having or at risk for a chronic kidney disease has diabetic nephropathy.

By "reduce" or "inhibit" in terms of the chronic kidney disease and proteinuria treatment methods described herein is meant the ability to cause an overall decrease preferably of 20% or greater, 30% or greater, 40% or greater, 45% or greater, more preferably of 50% or greater, of 55% or greater, of 60% or greater, of 65% or greater, of 70% or greater, and most preferably of 75% or greater, 80% or greater, 85% or greater, 90% or greater, or 95% or greater, for a given parameter or symptom of a chronic kidney disease. Reduce or inhibit can refer to, for example, symptoms of the disorder being treated, for example, high blood pressure, protein in the urine, etc.

High blood pressure is almost always present during all stages of chronic kidney disease. A nervous system exam may show signs of nerve damage. The health care provider may hear abnormal heart or lung sounds when listening with a stethoscope. The early symptoms of chronic kidney disease are also symptoms of other illnesses. These symptoms can be the only signs of kidney disease until the condition is more advanced. Symptoms of chronic kidney disease can include: appetite loss; general ill feeling and fatigue; headaches; itching (pruritus) and dry skin; nausea; weight loss without trying to lose weight; etc. Other symptoms that can develop, especially when kidney function has gotten worse, include: abnormally dark or light skin; bone pain; brain and nervous system symptoms; drowsiness and confusion; problems concentrating or thinking; numbness in the hands, feet, or other areas; muscle twitching or cramps; breath odor; easy bruising, bleeding, or blood in the stool; excessive thirst; frequent hiccups; low level of sexual interest and impotence; stopping of menstrual periods (amenorrhea); shortness of breath; sleep problems, such as insomnia, restless leg syndrome, and obstructive sleep apnea; swelling of the feet and hands (edema); vomiting, typically in the morning.

Accordingly, in some embodiments of the methods described herein, an effective amount of a composition comprising a ROBO2 inhibitor described herein is administered to a subject in order to alleviate a symptom of chronic kidney disease. As used herein, "alleviating a symptom chronic kidney disease" is ameliorating any condition or symptom associated with the chronic kidney disease. Alternatively, alleviating a symptom of a chronic kidney disease can involve reducing one or more symptoms of the chronic kidney disease in the subject relative to an untreated control suffering from chronic kidney disease or relative to the subject prior to the treatment. As compared with an equivalent untreated control, or the subject prior to the treatment with the ROBO2 inhibitor, such reduction or degree of prevention is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or more, as measured by any standard technique. Desirably, the chronic kidney disease is significantly reduced or undetectable, as detected by any standard method known in the art, in which case the chronic kidney disease is considered to have been treated. A patient who is being treated for a chronic kidney disease is one who a medical practitioner has diagnosed as having such a condition. Diagnosis can be by any suitable means known to one of ordinary skill in the art. Diagnosis and monitoring can involve, for example, detecting the level of specific proteins or molecules in a urine, blood, or serum sample, such as, for example, albumin, calcium, cholesterol, complete blood count (CBC), electrolytes, magnesium, phosphorous, potassium, sodium, or any combination thereof; assays to detect, for example, creatinine clearance; creatinine levels; BUN (blood urea nitrogen); through the use of specific techniques or procedures, such as an abdominal CT scan, abdominal MRI, abdominal ultrasound, kidney biopsy, kidney scan, kidney ultrasound; via detection of changes in results of assays or tests for erythropoietin, PTH; bone density test, or Vitamin D; or any combination of such detection methods and assays.

The terms "subject" and "individual" as used in regard to any of the methods described herein are used interchangeably herein, and refer to an animal, for example a human, recipient of the ROBO2 inhibitors described herein. For treatment of disease states which are specific for a specific animal such as a human subject, the term "subject" refers to that specific animal. The terms "non-human animals" and "non-human mammals" are used interchangeably herein, and include mammals such as rats, mice, rabbits, sheep, cats, dogs, cows, pigs, and non-human primates. The term "subject" also encompasses any vertebrate including but not limited to mammals, reptiles, amphibians and fish. However, advantageously, the subject is a mammal such as a human, or other mammals such as a domesticated mammal, e.g. dog, cat, horse, and the like.

In some embodiments of these methods and all such methods described herein, the method further comprises administering to the subject an additional therapeutic agent, in addition to the ROBO2 inhibitor. Such an additional therapeutic agent can be co-administered with the ROBO2 inhibitor. As used herein, the phrase "co-administering" or to "co-administer" means the administration of a ROBO2 inhibitor described herein and another compound, e.g., a therapeutic agent, separately, simultaneously, and/or sequentially over a period of time as determined by a qualified care giver.

In some such embodiments, the additional therapeutic agent is an angiotensin-converting enzyme (ACE) inhibitor, an angiotensin II receptor blocker (ARB), or a mineralocorticoid receptor (MR) antagonist.

ACE inhibitors for use with the ROBO2 inhibitors described herein include, but are not limited to, benazepril (marketed in the U.S. as LOTENSIN™), captopril (marketed in the U.S. as CAPOTEN™), enalapril/enalaprilat (marketed in the U.S. as VASOTEC™ oral and injectable), fosinopril (marketed in the U.S. as MONOPRIL™), lisinopril (marketed in the U.S. as ZESTRIL™ and PRINIVIL™), moexipril (marketed in the U.S. as UNIVASC™), perindopril (marketed in the U.S. as ACEON™), quinapril (marketed in the U.S. as ACCUPRIL™), ramipril (marketed in the U.S. as ALTACE™), and trandolapril (marketed in the U.S. as MAVIK™). ARBs for use with the ROBO2 inhibitors described herein include candesartan (marketed in the U.S. as ATACAND™), irbesartan (marketed in the U.S. as AVAPRO™), olmesartan (marketed in the U.S. as BENICAR™), losartan (marketed in the U.S. as COZAAR™), valsartan (marketed in the U.S. as DIOVAN™), telmisartan (marketed in the U.S. as MICARDIS™), and eprosartan (marketed in the U.S. as TEVETEN™).

In some embodiments of these methods and all such methods described herein, the method further comprises administering to the subject an effective amount of a diuretic, in addition to the ROBO2 inhibitor. Diuretics include, but are not limited to, torsemide (marketed in the U.S. as DEMADEX™), furosemide (marketed in the U.S. as LASIX™), bumetanide (marketed in the U.S. as BUMEX™), ethacrynic acid (marketed in the U.S. as EDECRIN™), torsemide (marketed in the U.S. as DEMADEX™), amiloride, (marketed in the U.S. as MIDAMOR™), acetazolamide (marketed in the U.S. as DIAMOX™), pamabrom (marketed in the U.S. as AQUABAN™), mannitol (marketed in the U.S. as ARIDOL™ or OSMITROL™), traimterene (marketed in the U.S. as DYRENIUM™), spironolactone (marketed in the U.S. as ALDACTONE™), amiloride (marketed in the U.S. as MIDAMOR™), indapamide (marketed in the U.S. as LOZOL™), hydrochlorothiazide (marketed in the U.S. as HYDRODIURIL™), metolazone (marketed in the U.S. as ZAROXOLYN™ or MYKROX™), methylclothiazide (marketed in the U.S. as AQUATENSEN™ or ENDURON™), hydrocholorthiazide (marketed in the U.S. as AQUAZIDE H™ or ESIDRIX™ or MICROZIDE™), chlorothiazide (marketed in the U.S. as DIURIL™), bendroflumethiazide (marketed in the U.S. as NATURETIN™), polythiazide (marketed in the U.S. as RENESE™), hydroflumethiazide (marketed in the U.S. as SALURON™), and chlorthalidone (marketed in the U.S. as THALITONE™). For a complete listing also see, e.g., Physician's Desk Reference, 2012 Edition, PDR Network (2011).

As used herein, in regard to any of the compositions and methods comprising ROBO-2 inhibitors or combination treatments thereof described herein, the terms "treat," "treatment," "treating," or "amelioration" refer to therapeutic treatments, wherein the object is to reverse, alleviate, ameliorate, inhibit, slow down or stop the progression or severity of a condition associated with, a disease or disorder. The term "treating" includes reducing or alleviating at least one adverse effect or symptom of a condition, disease or disorder associated with a chronic kidney disease, such as, but not limited to, diabetic nephropathy. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The term "treatment" of a disease also includes providing relief from the symptoms or side-effects of the disease (including palliative treatment).

The term "effective amount" as used herein refers to the amount of a ROBO-2 inhibitor described herein, needed to alleviate at least one or more symptom of the disease or disorder being treated, and relates to a sufficient amount of pharmacological composition to provide the desired effect. The term "therapeutically effective amount" therefore refers to an amount of the ROBO-2 inhibitor described herein, using the methods as disclosed herein, that is sufficient to provide a particular effect when administered to a typical subject. An effective amount as used herein would also include an amount sufficient to delay the development of a symptom of the disease, alter the course of a symptom disease (for example but not limited to, slow the progression of a symptom of the disease), or reverse a symptom of the disease. Thus, it is not possible to specify the exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the ROBO-2 inhibitor described herein, which achieves a half-maximal inhibition of measured function or activity) as determined in cell culture, or in an appropriate animal model. Levels in plasma can be measured, for example, by high performance liquid chromatography. The effects of any particular dosage can be monitored by a suitable bioassay. The dosage can be determined by a physician and adjusted, as necessary, to suit observed effects of the treatment. Depending on the type and severity of the chronic kidney disease, about 1 µg/kg to 100 mg/kg (e.g., 0.1-20 mg/kg) of a ROBO2 inhibitor described herein is an initial candidate dosage range for administration to the subject, whether, for example, by one or more separate administrations, or by continuous infusion.

Modes of Administration

The ROBO2 inhibitors or combination treatments thereof described herein can be administered to a subject in need thereof by any appropriate route which results in an effective treatment in the subject. As used herein, the terms "administering," and "introducing" are used interchangeably and refer to the placement of a ROBO-2 inhibitor into a subject by a method or route which results in at least partial localization of such agents at a desired site, such that a desired effect(s) is produced.

In some embodiments, the ROBO2 inhibitor is administered to a subject having a chronic kidney disease by any mode of administration that delivers the agent systemically or to a desired surface or target, and can include, but is not limited to, injection, infusion, instillation, and inhalation administration. To the extent that polypeptide agents can be protected from inactivation in the gut, oral administration forms are also contemplated. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments, the ROBO-2 inhibitors for use in the methods described herein are administered by intravenous infusion or injection.

The phrases "parenteral administration" and "administered parenterally" as used herein, refer to modes of administration other than enteral and topical administration, usually by injection. The phrases "systemic administration," "administered systemically", "peripheral administration" and "administered peripherally" as used herein refer to the administration of the ROBO-2 inhibitor, other than directly into a target site, tissue, or organ, such as a tumor site, such that it enters the subject's circulatory system and, thus, is subject to metabolism and other like processes.

For the clinical use of the methods described herein, administration of the ROBO-2 inhibitors described herein, can include formulation into pharmaceutical compositions or pharmaceutical formulations for parenteral administration, e.g., intravenous; mucosal, e.g., intranasal; ocular, or other mode of administration. In some embodiments, the ROBO-2 inhibitors described herein can be administered along with any pharmaceutically acceptable carrier compound, material, or composition which results in an effective treatment in the subject. Thus, a pharmaceutical formulation for use in the methods described herein can contain a ROBO-2 inhibitor, as described herein, in combination with one or more pharmaceutically acceptable ingredients.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent, media, encapsulating material, manufacturing aid (e.g., lubricant, talc magnesium, calcium or zinc stearate, or steric acid), or solvent encapsulating material, involved in maintaining the stability, solubility, or activity of, a ROBO-2 inhibitor. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) excipients, such as cocoa butter and suppository waxes; (8) oils, such as peanut oil, cottonseed oil, safflower oil, sesame oil, olive oil, corn oil and soybean oil; (9) glycols, such as propylene glycol; (10) polyols, such as glycerin, sorbitol, mannitol and polyethylene glycol (PEG); (11) esters, such as ethyl oleate and ethyl laurate; (12) agar; (13) buffering agents, such as magnesium hydroxide and aluminum hydroxide; (14) alginic acid; (15) pyrogen-free water; (16) isotonic saline; (17) Ringer's solution; (19) pH buffered solutions; (20) polyesters, polycarbonates and/or polyanhydrides; (21) bulking agents, such as polypeptides and amino acids (22) serum components, such as serum albumin, HDL and LDL; (23) C2-C12 alcohols, such as ethanol; and (24) other non-toxic compatible substances employed in pharmaceutical formulations. Release agents, coating agents, preservatives, and antioxidants can also be present in the formulation. The terms such as "excipient", "carrier", "pharmaceutically acceptable carrier" or the like are used interchangeably herein.

The ROBO-2 inhibitors described herein can be specially formulated for administration of the compound to a subject in solid, liquid or gel form, including those adapted for the following: (1) parenteral administration, for example, by subcutaneous, intramuscular, intravenous or epidural injection as, for example, a sterile solution or suspension, or sustained-release formulation; (2) topical application, for example, as a cream, ointment, or a controlled-release patch or spray applied to the skin; (3) intravaginally or intrarectally, for example, as a pessary, cream or foam; (4) ocularly; (5) transdermally; (6) transmucosally; or (79) nasally. Additionally, a ROBO-2 inhibitor can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960.

Further embodiments of the formulations and modes of administration of the compositions comprising the ROBO-2 inhibitors described herein, that can be used in the methods described herein are described below.

Parenteral Dosage Forms.

Parenteral dosage forms of the ROBO-2 inhibitors can also be administered to a subject with a chronic kidney condition by various routes, including, but not limited to, subcutaneous, intravenous (including bolus injection), intramuscular, and intraarterial. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, controlled-release parenteral dosage forms, and emulsions.

Suitable vehicles that can be used to provide parenteral dosage forms of the disclosure are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

In some embodiments, compositions comprising an effective amount of a ROBO2 inhibitor are formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington's Pharmaceutical Sciences, 18th ed., Mack Publishing, Easton, Pa. (1990).

Due to their ease of administration, tablets and capsules represent the most advantageous solid oral dosage unit forms, in which case solid pharmaceutical excipients are used. If desired, tablets can be coated by standard aqueous or nonaqueous techniques. These dosage forms can be prepared by any of the methods of pharmacy. In general, pharmaceutical compositions and dosage forms are prepared by uniformly and intimately admixing the active ingredient(s) with liquid carriers, finely divided solid carriers, or both, and then shaping the product into the desired presentation if necessary. In some embodiments, oral dosage forms are not used for the antibiotic agent.

Typical oral dosage forms of the compositions comprising an effective amount of a ROBO2 inhibitor are prepared by combining the pharmaceutically acceptable salt of the ROBO2 inhibitor in an intimate admixture with at least one excipient according to conventional pharmaceutical compounding techniques. Excipients can take a wide variety of forms depending on the form of the composition desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, microcrystalline cellulose, kaolin, diluents, granulating agents, lubricants, binders, and disintegrating agents.

Binders suitable for use in the pharmaceutical formulations described herein include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical formulations described herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions described herein is typically present in from about 50 to about 99 weight percent of the pharmaceutical composition.

Disintegrants are used in the oral pharmaceutical formulations described herein to provide tablets that disintegrate when exposed to an aqueous environment. A sufficient amount of disintegrant that is neither too little nor too much to detrimentally alter the release of the active ingredient(s) should be used to form solid oral dosage forms of the ROBO2 inhibitors described herein. The amount of disintegrant used varies based upon the type of formulation, and is readily discernible to those of ordinary skill in the art. Disintegrants that can be used to form oral pharmaceutical formulations include, but are not limited to, agar, alginic acid, calcium carbonate, microcrystalline cellulose, croscarmellose sodium, crospovidone, polacrilin potassium, sodium starch glycolate, potato or tapioca starch, other starches, pre-gelatinized starch, clays, other algins, other celluloses, gums, and mixtures thereof.

Lubricants that can be used to form oral pharmaceutical formulations of the ROBO2 inhibitors described herein, include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL® 200, manufactured by W. R. Grace Co. of Baltimore, Md.), a coagulated aerosol of synthetic silica (marketed by Degussa Co. of Piano, Tex.), CAB-O-SIL® (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

In other embodiments, lactose-free pharmaceutical formulations and dosage forms are provided, wherein such compositions preferably contain little, if any, lactose or other mono- or di-saccharides. As used herein, the term "lactose-free" means that the amount of lactose present, if any, is insufficient to substantially increase the degradation rate of an active ingredient. Lactose-free compositions of the disclosure can comprise excipients which are well known in the art and are listed in the USP (XXI)/NF (XVI), which is incorporated herein by reference.

The oral formulations of the ROBO2 inhibitors further encompass, in some embodiments, anhydrous pharmaceutical compositions and dosage forms comprising the ROBO2 inhibitors described herein as active ingredients, since water can facilitate the degradation of some compounds. For example, the addition of water (e.g., 5%) is widely accepted in the pharmaceutical arts as a means of simulating long-term storage in order to determine characteristics such as shelf life or the stability of formulations over time. See, e.g., Jens T. Carstensen, Drug Stability: Principles & Practice, 379-80 (2nd ed., Marcel Dekker, NY, N.Y.: 1995). Anhydrous pharmaceutical compositions and dosage forms described herein can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected. Anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials) with or without desiccants, blister packs, and strip packs.

Aerosol Formulations.

A ROBO-2 inhibitor can be packaged in a pressurized aerosol container together with suitable propellants, for example, hydrocarbon propellants like propane, butane, or isobutane with conventional adjuvants. A ROBO-2 inhibitor can also be administered in a non-pressurized form such as in a nebulizer or atomizer. A ROBO-2 inhibitor can also be administered directly to the airways in the form of a dry powder, for example, by use of an inhaler.

Suitable powder compositions include, by way of illustration, powdered preparations of a ROBO-2 inhibitor, thoroughly intermixed with lactose, or other inert powders acceptable for intrabronchial administration. The powder compositions can be administered via an aerosol dispenser or encased in a breakable capsule which can be inserted by the subject into a device that punctures the capsule and blows the powder out in a steady stream suitable for inhalation. The compositions can include propellants, surfactants, and co-solvents and can be filled into conventional aerosol containers that are closed by a suitable metering valve.

Aerosols for the delivery to the respiratory tract are known in the art. See for example, Adjei, A. and Garren, J. Pharm. Res., 1: 565-569 (1990); Zanen, P. and Lamm, J.-W. J. Int. J. Pharm., 114: 111-115 (1995); Gonda, I. "Aerosols for delivery of therapeutic and diagnostic agents to the respiratory tract," in Critical Reviews in Therapeutic Drug Carrier Systems, 6:273-313 (1990); Anderson et al., Am. Rev. Respir. Dis., 140: 1317-1324 (1989)) and have potential for the systemic delivery of peptides and proteins as well (Patton and Platz, Advanced Drug Delivery Reviews, 8:179-196 (1992)); Timsina et. al., Int. J. Pharm., 101: 1-13 (1995); and Tansey, I. P., Spray Technol. Market, 4:26-29 (1994); French, D. L., Edwards, D. A. and Niven, R. W., Aerosol Sci., 27: 769-783 (1996); Visser, J., Powder Technology 58: 1-10 (1989)); Rudt, S, and R. H. Muller, J. Controlled Release, 22: 263-272 (1992); Tabata, Y, and Y. Ikada, J. Biomed. Mater. Res., 22: 837-858 (1988); Wall, D. A., Drug Delivery, 2: 10 1-20 1995); Patton, J. and Platz, R., Adv. Drug Del. Rev., 8: 179-196 (1992); Bryon, P., Adv. Drug. Del. Rev., 5: 107-132 (1990); Patton, J. S., et al., Controlled Release, 28: 15 79-85 (1994); Damms, B. and Bains, W., Nature Biotechnology (1996); Niven, R. W., et al., Pharm. Res., 12(9); 1343-1349 (1995); and Kobayashi, S., et al., Pharm. Res., 13(1): 80-83 (1996), contents of all of which are herein incorporated by reference in their entirety.

The formulations of the ROBO-2 inhibitors described herein further encompass anhydrous pharmaceutical compositions and dosage forms comprising the disclosed compounds as active ingredients, since water can facilitate the degradation of some compounds. For example, the addition of water (e.g., 5%) is widely accepted in the pharmaceutical arts as a means of simulating long-term storage in order to determine characteristics such as shelf life or the stability of formulations over time. See, e.g., Jens T. Carstensen, Drug Stability: Principles & Practice, 379-80 (2nd ed., Marcel Dekker, NY, N.Y.: 1995). Anhydrous pharmaceutical compositions and dosage forms of the disclosure can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected. Anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials) with or without desiccants, blister packs, and strip packs.

Controlled and Delayed Release Dosage Forms.

In some embodiments of the aspects described herein, a ROBO-2 inhibitor can be administered to a subject by controlled- or delayed-release means. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2)

reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. (Kim, Cherng-ju, Controlled Release Dosage Form Design, 2 (Technomic Publishing, Lancaster, Pa.: 2000)). Controlled-release formulations can be used to control a compound of formula (I)'s onset of action, duration of action, plasma levels within the therapeutic window, and peak blood levels. In particular, controlled- or extended-release dosage forms or formulations can be used to ensure that the maximum effectiveness of a compound of formula (I) is achieved while minimizing potential adverse effects and safety concerns, which can occur both from under-dosing a drug (i.e., going below the minimum therapeutic levels) as well as exceeding the toxicity level for the drug.

A variety of known controlled- or extended-release dosage forms, formulations, and devices can be adapted for use with the ROBO-2 inhibitors described herein. Examples include, but are not limited to, those described in U.S. Pat. Nos. 3,845,770; 3,916,899; 3,536,809; 3,598,123; 4,008,719; 5674,533; 5,059,595; 5,591,767; 5,120,548; 5,073,543; 5,639,476; 5,354,556; 5,733,566; and 6,365,185 B1, each of which is incorporated herein by reference in their entireties. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of the disclosed compounds and thus effect controlled delivery of the drug. Examples of specific anion exchangers include, but are not limited to, DUO-LITE® A568 and DUOLITE® AP143 (Rohm & Haas, Spring House, Pa. USA).

In some embodiments of the methods described herein, a ROBO-2 inhibitor for use in the methods described herein is administered to a subject by sustained release or in pulses. Pulse therapy is not a form of discontinuous administration of the same amount of a composition over time, but comprises administration of the same dose of the composition at a reduced frequency or administration of reduced doses. Sustained release or pulse administrations are particularly preferred when the disorder occurs continuously in the subject, for example where the subject has chronic kidney disease. Each pulse dose can be reduced and the total amount of a ROBO-2 inhibitor described herein administered over the course of treatment to the subject or patient is minimized.

The interval between pulses, when necessary, can be determined by one of ordinary skill in the art. Often, the interval between pulses can be calculated by administering another dose of the composition when the composition or the active component of the composition is no longer detectable in the subject prior to delivery of the next pulse. Intervals can also be calculated from the in vivo half-life of the composition. Intervals can be calculated as greater than the in vivo half-life, or 2, 3, 4, 5 and even 10 times greater the composition half-life. Various methods and apparatus for pulsing compositions by infusion or other forms of delivery to the patient are disclosed in U.S. Pat. Nos. 4,747,825; 4,723,958; 4,948,592; 4,965,251 and 5,403,590.

In some embodiments, sustained-release preparations comprising the ROBO-2 inhibitor can be prepared. Suitable examples of sustained-release preparations include semipermeable matrices of solid hydrophobic polymers containing the inhibitor, in which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT (injectable microspheres composed of lactic acid-glycolic acid copolymer and leuprolide acetate), and poly-D-(−)-3-hydroxybutyric acid.

The formulations comprising the ROBO-2 inhibitors to be used for in vivo administration are preferably sterile. This is readily accomplished by filtration through, for example, sterile filtration membranes, and other methods known to one of skill in the art.

Also provided herein, in some aspects, are assays, methods, and systems for determining whether an individual has a chronic kidney disease or a pre-disposition for a chronic kidney disease or proteinuria based on expression profiles or sequence information of ROBO2 as a biomarker indicative of chronic kidney disease or a pre-disposition for a chronic kidney disease or proteinuria. As demonstrated herein, ROBO2 is useful as a biomarker to identify a subject having chronic kidney disease or at high risk for chronic kidney disease or proteinuria or to monitor the effects of treatment on the progression of chronic kidney disease or proteinuria.

As used herein, a "biomarker" refers to an organic biomolecule which is differentially present in a sample taken from a subject of one phenotypic status (e.g., having a disease) as compared with another phenotypic status (e.g., not having the disease). A biomarker is differentially present between different phenotypic statuses if the mean or median expression level of the biomarker in the different groups is calculated to be statistically significant. Common tests for statistical significance include, among others, t-test, ANOVA, Kruskal-Wallis, Wilcoxon, Mann-Whitney and odds ratio. Biomarkers, alone or in combination, provide measures of relative risk that a-subject belongs to one phenotypic status or another. As such, they are useful as markers for disease (diagnostics), therapeutic effectiveness of a drug (theranostics) and of drug toxicity.

ROBO2 expression for use in the assays described herein can be detected by any suitable method, including detection or protein levels or detection of mRNA expression levels. ROBO2 polypeptide can be detected in any form that may be found in a biological sample obtained from a subject, or in any form that may result from manipulation of the biological sample (e.g., as a result of sample processing). Modified forms of ROBO2 can include modified proteins that are a product of allelic variants, splice variants, post-translational modification (e.g., glycosylation, proteolytic cleavage (e.g., fragments of a parent protein), glycosylation, phosphorylation, lipidation, oxidation, methylation, cysteinylation, sulphonation, acetylation, and the like), oligomerization, de-oligomerization (to separate monomers from a multimeric form of the protein), denaturation, and the like.

The assays described herein can be designed to detect all forms or particular forms of ROBO2. Where desired, differentiation between different forms of ROBO2, e.g., different isoforms, can be accomplished by use of detection methods dependent upon physical characteristics that differ between the forms, e.g., different molecular weight, different molecular size, presence/absence of different epitopes, and the like.

Accordingly, provided herein, in some aspects, are assays for the diagnosis of a subject at having chronic kidney disease or at risk for chronic kidney disease or proteinuria, the assay comprising: measuring the level of ROBO2 protein or nucleic acid in a biological sample obtained from the subject, wherein if the level of the ROBO2 in the biological sample from the subject is at the same level or greater than (e.g., greater than by a statistically significant amount) a threshold reference level for ROBO2, the subject likely is at risk for chronic kidney disease or proteinuria or has chronic kidney disease. For example, an increase in the level of ROBO2 by more than about 10%, or more than about 20%, or more than about 30%, or more than about 40%, or more than about 50%, or more than about 60%, or more, as compared to a reference threshold level of ROBO2. In some embodiments, the increase in the level of ROBO2 is at least one standard deviation greater than, or at least two standard deviations, or more, greater than a median or mean ROBO2 reference threshold level. Such median or mean ROBO2 reference levels can be obtained, for example, from five or more samples obtained from subjects not having chronic kidney disease or proteinuria, or from five or more samples obtained from the same subject at different timepoints.

In some embodiments of these assays, the amount of ROBO2 measured in a biological sample is compared to a reference threshold level, or a reference biological sample, such as biological sample obtained from an age-matched normal control (e.g., an age-matched subject not having a risk of chronic kidney disease or proteinuria), or a healthy subject, e.g., a healthy individual.

In some embodiments, the assays, systems and kits as disclosed herein are also useful for monitoring a course of treatment being administered to a subject. For example, one can measure the level of ROBO2 in a biological sample in the subject at a first timepoint (e.g., t1) and compare with the ROBO2 biomarker reference threshold level, and if the measured level for ROBO2 is the same or higher than the reference threshold level, the subject can be administered an appropriate therapeutic treatment or regimen to delay or reduce the occurrence of chronic kidney disease or proteinuria, e.g., for example, increase exercise, reduce heart pressure, adjust diet etc. as disclosed in the methods herein, and then the level of the panel of ROBO2 biomarker protein can be measured at a second (e.g., t2) and subsequent timepoints (e.g., t3, t4, t5, t5 . . . etc.), and compared to levels of tROBO2 at one or more time points (e.g., at t1 or any subsequent timepoint) or the reference threshold levels of ROBO2 to determine if the therapeutic treatment or medical treatment or regimen for the treatment to reduce the risk of, delay, or reduce the occurrence of chronic kidney disease or proteinuria is effective. In some such embodiments, the assays, systems and kits as disclosed herein can be used to monitor a therapeutic treatment in a symptomatic subject (e.g., a subject known to have chronic kidney disease or proteinuria), where an effective treatment can be a decrease in ROBO2 in the subject, or alternatively the assays, systems and kits as disclosed herein can be used to monitor the effect of prophylactic treatment in an asymptomatic subject (e.g., to prevent chronic kidney disease or proteinuria occurring in a subject), for example, where the subject has been identified to be at risk of chronic kidney disease or proteinuria according to the methods as disclosed herein, or others known in the art, or due to hereditary reasons, for example.

The term "sample" as used herein generally refers to any material containing nucleic acid, either DNA or RNA, or amino acids. Generally, such material will be in the form of a blood sample, stool sample, tissue sample, cells, bacteria, histology section, or buccal swab. Samples can be prepared, for example samples can be fresh, fixed, frozen, or embedded in paraffin. The term "biological sample" as used herein refers to a cell or population of cells or a quantity of tissue or fluid from a subject. Most often, the sample has been removed from a subject, but the term "biological sample" can also refer to cells or tissue analyzed in vivo, i.e. without removal from the subject. Often, a "biological sample" will contain cells from the animal, but the term can also refer to non-cellular biological material, such as non-cellular fractions of blood, saliva, or urine, that can be used to measure gene expression levels. Biological samples include, but are not limited to, tissue biopsies, scrapes, whole blood, plasma, serum, urine, saliva, cell culture, or cerebrospinal fluid. Biological samples also include tissue biopsies, cell culture. A biological sample or tissue sample can refers to a sample of tissue or fluid isolated from an individual, including but not limited to, for example, urine, blood, plasma, serum, kidney biopsy, stool, sputum, spinal fluid, pleural fluid, nipple aspirates, lymph fluid, the external sections of the skin, respiratory, intestinal, and genitourinary tracts, tears, saliva, milk, cells (including but not limited to blood cells), tumors, organs, and also samples of an in vitro cell culture constituent. In some embodiments, where a urine sample is obtained, the urine sample is centrifuged to pellet any kidney cells, on which the assays and methods described herein can be performed. In some embodiments, the sample is from a kidney biopsy, such as a core needle biopsy of a kidney or portion thereof, such as a podocyte sample. In addition, fine needle aspirate samples are used. In some embodiments, the biological samples can be prepared, for example biological samples can be fresh, fixed, frozen, or embedded in paraffin. The sample can be obtained by removing a sample of cells from a subject, but can also be accomplished by using previously isolated cells (e.g. isolated by another person), or by performing the methods described herein in vivo.

The term "expression" as used herein refers to interchangeably to the expression of a polypeptide or protein or expression of a polynucleotide or expression of a gene. Expression also refers to the expression of pre-translational modified and post-translationally modified proteins, as well as expression of pre-mRNA molecules, alternatively spliced and mature mRNA molecules. Expression of a polynucleotide can be determined, for example, by measuring the production of RNA transcript molecules, for example messenger RNA (mRNA) transcript levels. Expression of a protein or polypeptide can be determined, for example, by immunoassay using an antibody(ies) that bind with the polypeptide. The term "encode" as it is applied to polynucleotides refers to a polynucleotide which is said to "encode" a polypeptide or protein if, in its native state or when manipulated by methods well known to those skilled in the art, it can be transcribed to produce the RNA which can be translated into an amino acid sequence to generate the polypeptide and/or a fragment thereof. The antisense strand is the complement of such a nucleic acid, and the encoding sequence can be deduced therefrom. The term "endogenously expressed" or "endogenous expression" refers to the expression of a gene product at normal levels and under normal regulation for that cell type.

Detection methods that can be used with the assays, methods, and systems described herein to measure levels of ROBO2 protein or nucleic acid in a sample or biological sample include optical methods, electrochemical methods (voltametry and amperometry techniques), atomic force microscopy, and radio frequency methods, e.g., multipolar resonance spectroscopy. Optical methods include microscopy, both confocal and non-confocal, detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

In those embodiments of the assays, methods, and systems described herein in which the level of ROBO2 protein is determined, such as, for example, the level of a protein of SEQ ID NO: 1 or SEQ ID NO: 3, one can use any proteomic approach commonly known to persons of ordinary skill in the art to measure the level of biomarker proteins in a biological sample. The measurement can be either quantitative or qualitative, so long as the measurement is capable of determining or indicating whether the level of ROBO2 protein in the biological sample is the same as, or above or below a reference threshold value for ROBO2 protein.

The measured level of ROBO2 protein can, in some embodiments, be a primary measurement of the level of ROBO2 protein measuring the quantity of ROBO2 protein itself, such as by detecting the number of ROBO2 protein molecules in the sample) or it can be, in some embodiments, a secondary measurement of ROBO2 protein (a measurement from which the quantity of ROBO2 protein can be but not necessarily deduced, such as a measure of functional activity or a measure of nucleic acid, such as mRNA, encoding ROBO2 protein). Qualitative data can also be derived or obtained from primary measurements.

In some embodiments of the assays and methods described herein, ROBO2 protein levels can be measured using an affinity-based measurement technology. "Affinity" as relates to an antibody is a term well understood in the art and means the extent, or strength, of binding of antibody to the binding partner, such as a biomarker as described herein (or epitope thereof). Affinity can be measured and/or expressed in a number of ways known in the art, including, but not limited to, equilibrium dissociation constant ($K_D$ or Kd), apparent equilibrium dissociation constant ($K_{D'}$ or $K_{d'}$), and $IC_{50}$ (amount needed to effect 50% inhibition in a competition assay; used interchangeably herein with "30"). It is understood that, for purposes of this invention, an affinity is an average affinity for a given population of antibodies which bind to an epitope.

Affinity-based measurement technology utilizes a molecule that specifically binds to the biomarker protein being measured (an "affinity reagent," such as an antibody or aptamer), although other technologies, such as spectroscopy-based technologies (e.g., matrix-assisted laser desorption ionization-time of flight, MALDI-TOF spectroscopy) or assays measuring bioactivity (e.g., assays measuring mitogenicity of growth factors) can also be used. Affinity-based technologies for use with the assays and methods described herein can include antibody-based assays (immunoassays) and assays utilizing aptamers (nucleic acid molecules which specifically bind to other molecules), such as ELONA. Additionally, assays utilizing both antibodies and aptamers are also contemplated (e.g., a sandwich format assay utilizing an antibody for capture and an aptamer for detection). A wide variety of affinity-based assays are also known in the art.

Affinity-based assays typically utilize at least one epitope derived from the biomarker protein, i.e., ROBO2, and many affinity-based assay formats utilize more than one epitope (e.g., two or more epitopes are involved in "sandwich" format assays; at least one epitope is used to capture the biomarker protein, and at least one different epitope is used to detect the marker).

Affinity-based assays can be in competition or direct reaction formats, utilize sandwich-type formats, and can further be heterogeneous (e.g., utilize solid supports) or homogenous (e.g., take place in a single phase) and/or utilize immunoprecipitation. Many assays involve the use of labeled affinity reagent (e.g., antibody, polypeptide, or aptamer); the labels can be, for example, enzymatic, fluorescent, chemiluminescent, radioactive, or dye molecules. Assays which amplify the signals from the probe are also known; examples of which are assays which utilize biotin and avidin, and enzyme-labeled and mediated immunoassays, such as ELISA and ELONA assays. For example, the biomarker concentrations from biological fluid samples may be measured by LUMINEX® assay or ELISA. Either of the biomarker or reagent specific for the biomarker can be attached to a surface and levels can be measured directly or indirectly.

In some embodiments of the assays, methods, and systems described herein, ROBO2 protein levels can be measured using an immunoassay affinity-based measurement technology.

Immunoassay technologies can include any immunoassay technology which can quantitatively or qualitatively measure the level of ROBO2 protein in a biological sample. Suitable immunoassay technologies include, but are not limited to radioimmunoassay, ELISA (enzyme-linked immunosorbant assay), "sandwich" immunoassays, immunoradiometric assays, immunodiffusion assays, in situ immunoassays (using colloidal gold, enzyme or radioisotope labels, for example), western blot analysis, immunoprecipitations, immunofluorescence assays, immunoelectrophoresis assays, fluoroimmunoassay (FiA), immunoradiometric assay (IRMA), immunoenzymometric assay (IEMA), immunoluminescence assay and immunofluorescence assay (Madersbacher S, Berger P. Antibodies and immunoassays. Methods 2000; 21:41-50), chemiluminescent assay, immuno-PCR, and western blot assay. Likewise, aptamer-based assays which can quantitatively or qualitatively measure the level of a biomarker in a biological sample can be used in the assays, methods, and systems described herein. Generally, aptamers can be substituted for antibodies in nearly all formats of immunoassay, although aptamers allow additional assay formats (such as amplification of bound aptamers using nucleic acid amplification technology such as PCR (U.S. Pat. No. 4,683,202) or isothermal amplification with composite primers (U.S. Pat. Nos. 6,251,639 and 6,692,918).

In some embodiments of the assays, methods, and systems described herein, where ROBO2 protein levels are measured using an immunoassay affinity-based measurement technology, the immunoassay is performed by measuring the extent of the protein/antibody interaction of the biomarker/antibody interaction. Any known method of immunoassay can be used.

In some embodiments, a binding partner, e.g., an antibody or a ligand binding to the ROBO2 protein in the binding assay, is preferably a labeled specific binding partner, but not necessarily an antibody. The binding partner is usually labeled itself, but alternatively it can be detected by a secondary reaction in which a signal is generated, e.g. from another labeled substance.

Thus, the antibody which specifically binds to ROBO2 protein can be used in the assays, methods, and systems described herein to determine the presence and/or amount of ROBO2 protein n a biological sample, which can be used to detect the increased or decreased concentration of ROBO2 protein present in a diagnostic sample. Such antibodies can be raised by any of the methods well known in the immunodiagnostics field. The antibodies can be anti-ROBO2 protein antibodies to any biologically relevant state of the protein. Thus, for example, they could be raised against the unglycosylated form of ROBO2 protein, which exists in the body in a glycosylated form, or against a peptide carrying a relevant epitope of ROBO2 protein.

In some embodiments of these assays, method, and systems, an amplified assay form can be used, whereby an enhanced "signal" is produced from a relatively low level of protein to be detected. One particular form of an amplified immunoassay is enhanced chemiluminescent assay. For example, the antibody is labeled with horseradish peroxidase, which participates in a chemiluminescent reaction with luminol, a peroxide substrate and a compound which enhances the intensity and duration of the emitted light, typically 4-iodophenol or 4-hydroxycinnamic acid.

In some embodiments of these assays, method, and systems, an amplified immunoassay can be used comprising immuno-PCR. In this technique, the antibody is covalently linked to a molecule of arbitrary DNA comprising PCR primers, whereby the DNA with the antibody attached to it is amplified by the polymerase chain reaction. See E. R. Hendrickson et al., Nucleic Acids Research 23: 522-529 (1995).

Accordingly, in all embodiments of the assays, method, and systems described herein, the level of ROBO2 protein can be determined using a protein-binding agent, also referred to herein as "protein-binding entity" or an "affinity reagent" can be used, in particular, antibodies. For instance, the affinity reagents, in particular, antibodies such as anti-biomarker antibodies can be used in an immunoassay, particularly in an ELISA (Enzyme Linked Immunosorbent Assay). In embodiments where the level of a biomarker protein can be measured in a biological sample using methods commonly known in the art, and including, for example but not limited to isoform-specific chemical or enzymatic cleavage of isoform proteins, immunobloting, immunohistochemical analysis, ELISA, and mass spectrometry.

In some embodiments of the assays, methods, and systems described herein, ROBO2 protein levels are measured using "Enzyme-Linked Immunosorbent Assay (ELISA)." ELISA is a technique for detecting and measuring the concentration of an antigen using a labeled (e.g. enzyme linked) form of the antibody. There are different forms of ELISA, which are well known to those skilled in the art. The standard techniques known in the art for ELISA are described in "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. 1984, J. Clin. Chem. Clin. Biochem., 22:895-904.

In some embodiments of the assays, methods, and systems described herein, ROBO2 protein levels are measured using a sandwich assay ELISA. In a "sandwich ELISA", an antibody (e.g. anti-enzyme) is linked to a solid phase (i.e. a microtiter plate) and exposed to a biological sample containing antigen (e.g. enzyme). The solid phase is then washed to remove unbound antigen. A labeled antibody (e.g. enzyme linked) is then bound to the bound-antigen (if present) forming an antibody-antigen-antibody sandwich. Accordingly, using this method, a first antibody to ROBO2 protein is bound to the solid phase such as a well of a plastics microtiter plate, and incubated with the sample and with a labeled second antibody specific to ROBO2 protein to be assayed. Examples of enzymes that can be linked to the antibody are alkaline phosphatase, horseradish peroxidase, luciferase, urease, and B-galactosidase. The enzyme linked antibody reacts with a substrate to generate a colored reaction product that can be measured.

In some embodiments of the assays, methods, and systems described herein, ROBO2 protein levels are measured using an antibody capture assay or competitive ELISA. In a "competitive ELISA", antibody is incubated with a sample containing antigen (i.e. enzyme). The antigen-antibody mixture is then contacted with a solid phase (e.g. a microtiter plate) that is coated with antigen (i.e., enzyme). The more antigen present in the sample, the less free antibody that will be available to bind to the solid phase. A labeled (e.g., enzyme linked) secondary antibody is then added to the solid phase to determine the amount of primary antibody bound to the solid phase. Accordingly, in some such embodiments, a biological test sample is allowed to bind to a solid phase, and the anti-ROBO2 protein antibody (e.g., antibodies that specifically bind ROBO2 protein) can be added and allowed to bind. After washing away unbound material, the amount of antibody bound to the solid phase is determined using a labeled second antibody, anti- to the first.

In some embodiments of these assays, method, and systems, a label is preferably an enzyme. The substrate for the enzyme can be, for example, color-forming, fluorescent or chemiluminescent.

In some embodiments of the assays, methods, and systems described herein, ROBO2 protein levels are measured using immunohistochemistry. In an "immunohistochemistry assay" a section of tissue is tested for specific proteins by exposing the tissue to antibodies that are specific for the protein that is being assayed. The antibodies are then visualized by any of a number of methods to determine the presence and amount of the protein present. Examples of methods used to visualize antibodies are, for example, through enzymes linked to the antibodies (e.g., luciferase, alkaline phosphatase, horseradish peroxidase, or beta-galactosidase), or chemical methods (e.g., DAB/Substrate chromagen). The sample is then analyzed microscopically, most preferably by light microscopy of a sample stained with a stain that is detected in the visible spectrum, using any of a variety of such staining methods and reagents known to those skilled in the art.

In some embodiments of the assays, methods, and systems described herein, ROBO2 protein levels are measured using radioimmunoassays. A radioimmunoassay is a technique for detecting and measuring the concentration of an antigen, i.e., ROBO2, using a labeled (e.g. radioactively or fluorescently labeled) form of the antigen. Examples of radioactive labels for antigens include 3H, 14C, and 125I. The concentration of ROBO2 in a biological sample is measured by having the ROBO2 in the biological sample compete with the labeled (e.g. radioactively) ROBO2 for binding to an antibody to ROBO2. To ensure competitive binding between the labeled ROBO2 and the unlabeled ROBO2, the labeled ROBO2 is present in a concentration sufficient to saturate the binding sites of the antibody. The higher the concentration of ROBO2 in the sample, the lower the concentration of labeled ROBO2 that will bind to the antibody.

In some embodiments of the assays, methods, and systems described herein, ROBO2 protein levels are measured using an immunoradiometric assay (IRMA). IRMA is an immunoassay in which the antibody reagent is radioactively labeled. An IRMA requires the production of a multivalent antigen conjugate, by techniques such as conjugation to a protein e.g., rabbit serum albumin (RSA). The multivalent antigen conjugate must have at least 2 antigen residues per molecule and the antigen residues must be of sufficient distance apart to allow binding by at least two antibodies to the antigen. For example, in an IRMA the multivalent antigen conjugate can be attached to a solid surface such as a plastic sphere. Unlabeled "sample" antigen and antibody to antigen which is radioactively labeled are added to a test tube containing the multivalent antigen conjugate coated sphere. The antigen in the sample competes with the multivalent antigen conjugate for antigen antibody binding sites. After an appropriate incubation period, the unbound reactants are removed by washing and the amount of radioactivity on the solid phase is determined. The amount of bound radioactive antibody is inversely proportional to the concentration of antigen in the sample.

Other techniques can be used to detect the level of ROBO2 protein in a biological sample can be performed according to a practitioner's preference, and based upon the present disclosure and the type of biological sample (i.e. plasma, urine, tissue sample etc.). One such technique is Western blotting (Towbin et at., Proc. Nat. Acad. Sci. 76:4350 (1979)), wherein a suitably treated sample is run on an SDS-PAGE gel before being transferred to a solid support, such as a nitrocellulose filter. Detectably labeled anti-ROBO2 antibodies or protein binding molecules can then be used to assess the level of ROBO2 protein, where the intensity of the signal from the detectable label corresponds to the amount of ROBO2 protein. Levels of the amount of ROBO2 protein present can also be quantified, for example by densitometry.

In some embodiments of the assays, methods, and systems described herein, ROBO2 protein levels are measured using mass spectrometry such as MALDI/TOF (time-of-flight), SELDI/TOF, liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, or tandem mass spectrometry (e.g., MS/MS, MS/MS/MS, ESI-MS/MS, etc.). See for example, U.S. Patent Application Nos: 20030199001, 20030134304, 20030077616, which are incorporated herein in their entirety by reference.

In some such embodiments, these methodologies can be combined with the machines, computer systems and media to produce an automated system for determining the level of ROBO2 protein in a biological sample and analysis to produce a printable report which identifies, for example, the level of ROBO2 protein in a biological sample. In some instances, the measurement of the level of ROBO2 is done remotely from the determination and comparison modules.

Mass spectrometry methods are well known in the art and have been used to quantify and/or identify biomolecules, such as proteins (see, e.g., Li et al. (2000) Tibtech 18:151-160; Rowley et al. (2000) Methods 20: 383-397; and Kuster and Mann (1998) Curr. Opin. Structural Biol. 8: 393-400). Further, mass spectrometric techniques have been developed that permit at least partial de novo sequencing of isolated proteins. Chait et al., Science 262:89-92 (1993); Keough et al., Proc. Natl. Acad. Sci. USA. 96:7131-6 (1999); reviewed in Bergman, EXS 88:133-44 (2000).

In certain embodiments, a gas phase ion spectrophotometer is used. In other embodiments, laser-desorption/ionization mass spectrometry is used to analyze the sample. Modern laser desorption/ionization mass spectrometry ("LDI-MS") can be practiced in two main variations: matrix assisted laser desorption/ionization ("MALDI") mass spectrometry and surface-enhanced laser desorption/ionization ("SELDI"). In MALDI, the analyte is mixed with a solution containing a matrix, and a drop of the liquid is placed on the surface of a substrate. The matrix solution then co-crystallizes with the biological molecules. The substrate is inserted into the mass spectrometer. Laser energy is directed to the substrate surface where it desorbs and ionizes the biological molecules without significantly fragmenting them. See, e.g., U.S. Pat. No. 5,118,937 (Hillenkamp et al.), and U.S. Pat. No. 5,045,694 (Beavis & Chait) which are incorporated herein by reference.

In SELDI, the substrate surface is modified so that it is an active participant in the desorption process. In one variant, the surface is derivatized with adsorbent and/or capture reagents that selectively bind the protein of interest. In another variant, the surface is derivatized with energy absorbing molecules that are not desorbed when struck with the laser. In another variant, the surface is derivatized with molecules that bind the protein of interest and that contain a photolytic bond that is broken upon application of the laser. In each of these methods, the derivatizing agent generally is localized to a specific location on the substrate surface where the sample is applied. See, e.g., U.S. Pat. No. 5,719,060 and WO 98/59361 which are incorporated herein by reference. The two methods can be combined by, for example, using a SELDI affinity surface to capture an analyte and adding matrix-containing liquid to the captured analyte to provide the energy absorbing material.

For additional information regarding mass spectrometers, see, e.g., Principles of Instrumental Analysis, 3rd edition, Skoog, Saunders College Publishing, Philadelphia, 1985; and Kirk-Othmer Encyclopedia of Chemical Technology, 4th ed. Vol. 15 (John Wiley & Sons, New York 1995), pp. 1071-1094.

Detection of the level of ROBO2 protein will typically depend on the detection of signal intensity. This, in turn, can reflect the quantity and character of a polypeptide bound to the substrate. For example, in certain embodiments, the signal strength of peak values from spectra of a first sample and a second sample can be compared (e.g., visually, by computer analysis etc.), to determine the relative amounts of particular biomolecules. Software programs such as the Biomarker Wizard program (Ciphergen Biosystems, Inc., Fremont, Calif.) can be used to aid in analyzing mass spectra. The mass spectrometers and their techniques are well known to those of skill in the art.

In some embodiments of the assays, methods, and systems described herein, ROBO2 protein levels are measured using gel electrophoresis techniques, in particular SDS-PAGE (Sodium Dodecylsulfate Polyacrylamide Gel Elektrophoresis), especially two dimensional PAGE (2D-PAGE), preferably two dimensional SDS-PAGE (2D-SDS-PAGE). According to a particular example, the assay is based on 2D-PAGE, in particular, using immobilized pH gradients (IPGs) with a pH range preferably over pH 4-9.

In some embodiments of the assays, methods, and systems described herein, ROBO2 protein levels are measured using gel electrophoresis techniques, in particular, the above mentioned techniques combined with other protein separation methods, particularly methods known to those skilled in the art, in particular, chromatography and/or size exclusion.

In some embodiments of the assays, methods, and systems described herein, ROBO2 protein levels are measured using resonance techniques, in particular, plasma surface resonance.

In some embodiments of the assays, methods, and systems described herein, ROBO2 protein levels are measured using a protein biochip. A biochip generally comprises a solid substrate having a substantially planar surface, to which a capture reagent (e.g., an adsorbent or affinity reagent) is attached. Frequently, the surface of a biochip comprises a plurality of addressable locations having bound capture reagent bound. The biochip may also include bound capture reagent that serves as a control. Protein biochips are biochips adapted for the capture of polypeptides. Many protein biochips are described in the art. These include, for example, protein biochips produced by Ciphergen Biosystems, Inc. (Fremont, Calif.), Zyomyx (Hayward, Calif.), Invitrogen (Carlsbad, Calif.), Biacore (Uppsala, Sweden) and Procognia (Berkshire, UK). Examples of such protein biochips are described in the following patents or published patent applications: U.S. Pat. No. 6,225,047 (Hutchens & Yip); U.S. Pat. No. 6,537,749 (Kuimelis and Wagner); U.S. Pat. No. 6,329,209 (Wagner et al.); PCT International Publication No. WO 00156934 (Englert et al.); PCT International Publication No. WO 031048768 (Boutell et al.) and U.S. Pat. No. 5,242,828 (Bergstrom et al.).

The reference threshold levels or values of ROBO2 protein levels used for comparison with the level of ROBO2 protein from a subject can vary, depending on the aspect or embodiment described herein being practiced, as will be understood throughout this specification, and below. A reference threshold value can be based on an individual sample value, such as for example, a value obtained from a biological sample from the subject being tested, but at an earlier point in time (e.g., at a first timepoint (t1), e.g., a first biomarker level measured, or at a second timepoint (t2), e.g.,). A reference threshold value can also be based on a pool of samples, for example, value(s) obtained from samples from a pool of subjects being tested. For example, in some embodiments, reference threshold values for ROBO2 protein are based on measured the 50% value (e.g., median) of ROBO2 protein measured in subjects known to have chronic kidney disease or proteinuria. For example, subjects in the top 50% (e.g., at or above the median level) for ROBO2 protein can be selected to be at risk of having chronic kidney disease or proteinuria. Reference value(s) can also be based on a pool of samples including or excluding the sample(s) to be tested. The reference value can be based on a large number of samples, such as from population of healthy subjects of the chronological age-matched group, or from subjects who do not have or do not have a risk of chronic kidney disease or proteinuria. In some embodiments, the reference value can be at least one, more typically at least two, standard deviations above the mean or median of any of these assays or a predetermined mean or median.

For assessing the risk of a subject likely to experience or have chronic kidney disease or proteinuria by the assays, methods, and systems as disclosed herein, a "reference threshold value" is typically a predetermined reference threshold level, such as the median urine, serum or blood ROBO2 protein obtained from a population of healthy subjects that are in the chronological age group matched with the chronological age of the tested subject. As indicated earlier, in some situations, the reference samples can also be gender matched, and/or matched based on ethnicity. In some embodiments, the reference threshold value for ROBO2 protein is the median level for that biomarker in a type of biological sample, e.g., urine, blood, serum, in a panel subjects for the same ethnicity, e.g., Caucasian, Black, Hispanic, Asian, and Asian-Indian, Pakistani, Middle Eastern and/or Pacific Islander.

For assessing the risk of a subject likely to experience or have chronic kidney disease or proteinuria by the assays, methods, and systems as disclosed herein, the reference threshold level for ROBO2 protein can be a predetermined level, such as an average or median of levels obtained from a population of healthy subjects that are in the chronological age group matched with the chronological age of the tested subject. Alternately, the reference threshold level for ROBO2 protein can be a historical reference level for the particular subject that was obtained from a sample derived from the same subject, but at an earlier point in time, and/or when the subject did not have a risk of chronic kidney disease or proteinuria. In some instances, the reference threshold level for ROBO2 protein can be a historical reference level of ROBO2 protein for a particular group of subjects whom have all had chronic kidney disease or proteinuria, due to, for example, diabetes.

In some embodiments, healthy subjects are selected as the control subjects. In some embodiments, controls are age-matched controls. Healthy subject can be used to obtain a reference threshold level ROBO2 protein in, for example, a urine or serum sample. A "healthy" subject or sample from a "healthy" subject or individual as used herein is the same as those commonly understood to one skilled in the art. For example, one may use methods commonly known to evaluate kidney function, as described herein, to select control subjects as healthy subjects for diagnosis and treatment methods described herein. In some embodiments, subjects in good health with no signs or symptom suggesting chronic kidney disease can be recruited as healthy control subjects. The subjects are evaluated based on extensive evaluations consisted of medical history, family history, physical and renal examinations by clinicians, laboratory tests. Examples of analyses of chronic kidney disease and/or proteinuria include, but are not limited to detecting the level of specific proteins or molecules in a urine, blood, or serum sample, such as, for example, albumin, calcium, cholesterol, complete blood count (CBC), electrolytes, magnesium, phosphorous, potassium, sodium, or any combination thereof; assays to detect, for example, creatinine clearance; creatinine levels; BUN (blood urea nitrogen); through the use of specific techniques or procedures, such as an abdominal CT scan, abdominal MRI, abdominal ultrasound, kidney biopsy, kidney scan, kidney ultrasound; via detection of changes in results of assays or tests for erythropoietin, PTH; bone density test, or Vitamin D; or any combination of such detection methods and assays.

Age-matched populations (from which reference values can be obtained) are ideally the same chronological age as the subject or individual being tested, but approximately age-matched populations are also acceptable. Approximately age-matched populations may be within 1, 2, 3, 4, or 5 years of the chronological age of the individual tested, or can be groups of different chronological ages which encompass the chronological age of the individual being tested.

A subject that is compared to its "chronological age matched group" is generally referring to comparing the subject with a chronological age-matched within a range of 5 to 20 years. Approximately age-matched populations can be in 2, 3, 4, 5, 6, 7, 8, 9, 10 or 15, or 20 year increments (e.g. a "5 year increment" group can serve as the source for reference values for a 62 year old subject might include 58-62 year old individuals, 59-63 year old individuals, 60-64 year old individuals, 61-65 year old individuals, or 62-66 year old individuals). In a broader definition, where there are larger gaps between different chronological age groups, for example, when there are few different chronological age groups available for reference values, and the gaps between different chronological age groups exceed the 2, 3, 4, 5, 6, 7, 8, 9, 10 or 15, or 20 year increments described herein, then the "chronological age matched group" can refer to the age group that is in closer match to the chronological age of the subject (e.g. when references values available for an older age group (e.g., 80-90 years) and a younger age group (e.g., 20-30 years), a chronological age matched group for a 51 year old can use the younger age group (20-30 years), which is closer to the chronological age of the test subject, as the reference level.

Other factors to be considered while selecting control subjects include, but not limited to, species, gender, ethnicity, and so on. Hence, in some embodiments, a reference level can be a predetermined reference level, such as an average or median of levels obtained from a population of healthy control subjects that are gender-matched with the gender of the tested subject. In some embodiments, a reference level can be a predetermined reference level, such as an average or median of levels obtained from a population of healthy control subjects that are ethnicity-matched with the ethnicity of the tested subject (e.g., Caucasian, Black, Hispanic, Asian, and Asian-Indian, Pakistani, Middle Eastern and Pacific Islander). In other embodiments, both chronological age and gender of the population of healthy subjects are matched with the chronological age and gender of the tested subject, respectively. In other embodiments, both chronological age and ethnicity of the population of healthy subjects are matched with the chronological age and ethnicity of the tested subject, respectively. In other embodiments, chronological age, gender, and ethnicity of the population of healthy control subjects are all matched with the chronological age, gender, and ethnicity of the tested subject, respectively.

The process of comparing a level of ROBO2 protein in a biological sample from a subject and a reference threshold level for ROBO2 protein can be carried out in any convenient manner appropriate and known to one of skill in the art. Generally, values of ROBO2 protein levels determined using the assays, methods, and systems described herein can be quantitative values (e.g., quantitative values of concentration, such as milligrams of ROBO2 protein per liter (e.g., mg/L) of sample, or an absolute amount). Alternatively, values of ROBO2 protein levels can be qualitative depending on the measurement techniques, and thus the mode of comparing a value from a subject and a reference value can vary depending on the measurement technology employed. For example, the comparison can be made by inspecting the numerical data, by inspecting representations of the data (e.g., inspecting graphical representations such as bar or line graphs), and using standard deviations of, for example, at least one, or at least two standard deviations. In one example, when a qualitative assay is used to measure ROBO2 protein levels, the levels can be compared by visually comparing the intensity of the colored reaction product, or by comparing data from densitometric or spectrometric measurements of the colored reaction product (e.g., comparing numerical data or graphical data, such as bar charts, derived from the measuring device).

As described herein, ROBO2 protein levels can be measured quantitatively (absolute values) or qualitatively (relative values). In some embodiments, quantitative values of ROBO2 protein levels in the biological samples can indicate a given level (or grade) of risk of chronic kidney disease or proteinuria.

In some embodiments, the comparison is performed to determine the magnitude of the difference between the values from a subject and reference values (e.g., comparing the "fold" or percentage difference between the measured ROBO2 protein levels obtained from a subject and the reference threshold ROBO2 protein value). A fold difference can be determined by measuring the absolute concentration of the ROBO2 protein levels, and comparing that to the absolute value to the reference threshold ROBO2 protein level, or a fold difference can be measured by the relative difference between a reference value and a sample value, where neither value is a measure of absolute concentration, and/or where both values are measured simultaneously. For example, an ELISA measures the absolute content or concentration of a protein from which a fold change is determined in comparison to the absolute concentration of the same protein in the reference. As another example, an antibody array measures the relative concentration from which a fold change is determined. Accordingly, the magnitude of the difference between the measured value and the reference value that suggests or indicates a particular diagnosis will depend on the method being practiced.

As will be apparent to those of skill in the art, when replicate measurements are taken for measurement of ROBO2 protein levels, the measured values from subjects can be compared with the reference threshold ROBO2 protein levels, and take into account the replicate measurements. The replicate measurements can be taken into account by using either the mean or median of the measured values.

In some embodiments, the process of comparing can be manual or it can, preferably, be automated. For example, an assay device (such as a luminometer for measuring chemiluminescent signals) can include circuitry and software enabling it to compare a value from a subject with a reference value for ROBO2 protein. Alternately, a separate device (e.g., a digital computer) can be used to compare the measured ROBO2 protein levels from subject(s) and the reference threshold levels for ROBO2 protein. Automated devices for comparison can include stored reference values for the ROBO2 protein, or can compare the measured ROBO2 protein levels from subject(s) with reference threshold levels for ROBO2 protein that are derived from contemporaneously measured reference samples In some embodiments, a subject tested for ROBO2 protein levels is assigned into one of two or more groups (statuses) based on the results of the assays, methods, and systems described herein. The diagnostic assays, methods, and systems described herein can be used to classify between a number of different states.

Accordingly, in some embodiments, determining whether a subject has a high risk of having chronic kidney disease or proteinuria (status: low-risk v. high risk) is performed using the diagnostic assays, methods, and systems described herein. Biomarker amounts or patterns of ROBO2 protein determined as being characteristic of various risk states, e.g., high, medium or low, are identified. The risk of developing chronic kidney disease or proteinuria is determined by measuring ROBO2 protein alone or in combination with other known biomarkers, and then either submitting them to a classification algorithm or comparing them with a reference amount (e.g., a cut off reference amount as disclosed herein) that is associated with the particular risk level.

In some embodiments, provided herein are diagnostic assays, methods, and systems for determining the severity or stage or risk of having a chronic kidney disease or proteinuria in a subject. Each stage of chronic kidney disease, for example, has a characteristic amount of ROBO2 protein or relative amounts of ROBO2 protein. The stage of a disease is determined by measuring ROBO2 protein, alone or in combination with other biomarkers, and then either submitting them to a classification algorithm or comparing them with a reference amount and/or pattern of biomarkers that is associated with the particular stage, e.g., how soon the subject will likely develop chronic kidney disease or proteinuria. For example, one can classify between likely to have chronic kidney disease or proteinuria within a year (e.g., a poor prognosis) or a subject likely to have chronic kidney disease or proteinuria in the next 5 years.

Additional embodiments of the diagnostic assays, methods, and systems relate to the communication of results or diagnoses or both to technicians, physicians or patients, for example. In certain embodiments, computers are used to communicate assay results or diagnoses or both to interested parties, e.g., physicians and their patients. In some embodiments, the assays are performed or the assay results analyzed in a country or jurisdiction which differs from the country or jurisdiction to which the results or diagnoses are communicated, for example. In some embodiments, a risk of having chronic kidney disease or proteinuria based on levels of ROBO2 protein in a biological sample from the subject is communicated to the subject after the levels or prognosis are obtained. The prognosis or diagnosis can be communicated to the subject by the subject's treating physician. Alternatively, the prognosis or diagnosis can be sent to the subject by email or communicated to the subject by phone. A computer can be used to communicate the prognosis or diagnosis by email or phone, or via the internet using a secure gateway patient log-in service. In certain embodiments, the message containing results of the prognosis or diagnostic test can be generated and delivered automatically to the subject using a combination of computer hardware and software which will be familiar to artisans skilled in telecommunications. In certain embodiments of the assays, methods, and systems described herein, all or some of the method steps, including the assaying of samples, diagnosing of diseases, and communicating of assay results or diagnoses, can be carried out in diverse (e.g., foreign) jurisdictions.

In some embodiments of the diagnostic assays, methods, and systems of qualifying or assessing a risk of chronic kidney disease or proteinuria described herein, the assays, methods, or systems further comprise managing subject treatment based on the determination of the risk of having a chronic kidney disease or proteinuria. Such management includes the actions of the physician or clinician subsequent to determining the subjects risk of having chronic kidney disease or proteinuria. For example, if a physician makes a diagnosis of the subject at risk of chronic kidney disease or proteinuria, then a certain regimen of treatment can follow. A suitable regimen of treatment can include, without limitation, a supervised exercise program; control of blood pressure, sugar intake, and/or lipid levels; and drug therapies. In some embodiments, a diagnosis of a risk of having chronic kidney disease or proteinuria can be followed by further testing to determine whether a patient is suffering from a chronic kidney disease, or whether the patient is suffering from a related disease. Also, if the diagnostic test gives an inconclusive result on the risk of a major adverse event status, further tests may be called for. In some embodiments of the diagnostic assays, methods, and systems of qualifying or assessing a risk of chronic kidney disease or proteinuria described herein, if a physician makes a diagnosis of the subject not being at risk of chronic kidney disease or proteinuria, then no treatment is provided.

The assay and ROBO2 detection methods described herein can be automated using robotics and computer directed systems. A biological sample, such as a urine, plasma, or blood sample, can be injected into a system, such as a microfluidic device entirely run by a robotic station from sample input to output of the result.

Accordingly, also provided herein, in some aspects are systems (and computer readable medium for causing computer systems) to perform a method for determining whether an individual has a chronic kidney disease or proteinuria or a pre-disposition for a chronic kidney disease or proteinuria based on expression profiles or sequence information.

In some aspects, provided herein are systems for assessing if a subject has or is at increased risk for chronic kidney disease or proteinuria, the systems comprising: (a) a determination module configured to receive a at least one biological sample and perform at least one analysis on said biological sample to measure a level of ROBO2 in the biological sample or determine the expression ratio of ROBO2 relative to a pre-determined or threshold reference level and to output said measured level or expression ratio; (b) a storage device configured to store data output information from the determination module; (c) a comparison module adapted to receive input from the storage device and compare the data stored on the storage device with at least one reference threshold ROBO2 level, wherein if the measured ROBO2 protein level is at least the same or higher than the reference threshold level, the comparison module provides information to an output module that the biological sample is associated with a subject that deviates from the reference threshold biomarker level; and (d) an output module for displaying the information to the user.

In all aspects of the invention, methods to determine the levels of ROBO2 protein can be performed using an automated machine or system. Such machines and systems generate a report, such as displaying a report on a visible screen or a printable report which indicates the levels of ROBO2 protein and/or report an increase or the same as a reference threshold level for ROBO2 protein, and/or if the subject from which the sample was obtained is at risk of chronic kidney disease or proteinuria.

Accordingly, some embodiments described herein also provide for a machine, computer systems and computer readable media for performing the steps of (i) determining the levels of ROBO2 protein, and (ii) indicating or reporting whether a subject is at risk of having chronic kidney disease or proteinuria.

Embodiments of these aspects are described through functional modules, which are defined by computer executable instructions recorded on computer readable media and which cause a computer to perform method steps when executed. The modules have been segregated by function for the sake of clarity. However, it should be understood that the modules need not correspond to discreet blocks of code and the described functions can be carried out by the execution of various code portions stored on various media and executed at various times. Furthermore, it should be appreciated that the modules can perform other functions, thus the modules are not limited to having any particular functions or set of functions.

The computer readable media can be any available tangible media that can be accessed by a computer. Computer readable media includes volatile and nonvolatile, removable and non-removable tangible media implemented in any method or technology for storage of information such as computer readable instructions, data structures, program modules or other data. Computer readable media includes, but is not limited to, RAM (random access memory), ROM (read only memory), EPROM (erasable programmable read only memory), EEPROM (electrically erasable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and non-volatile memory, and any other tangible medium which can be used to store the desired information and which can accessed by a computer including and any suitable combination of the foregoing.

Computer-readable data embodied on one or more computer-readable media, or computer readable medium, can define instructions, for example, as part of one or more programs, that, as a result of being executed by a computer, instruct the computer to perform one or more of the functions described herein (e.g., in relation to a system, or computer readable medium), and/or various embodiments, variations and combinations thereof. Such instructions can be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable media on which such instructions are embodied can reside on one or more of the components of either of the system, or computer readable medium described herein, can be distributed across one or more of such components, and can be in transition there between.

The computer-readable media can be transportable such that the instructions stored thereon can be loaded onto any computer resource to implement the aspects of the present invention discussed herein. In addition, it should be appreciated that the instructions stored on the computer readable media, or the computer-readable medium, described above, are not limited to instructions embodied as part of an application program running on a host computer. Rather, the instructions can be embodied as any type of computer code (e.g., software or microcode) that can be employed to program a computer to implement aspects of the present invention. The computer executable instructions can be written in a suitable computer language or combination of several languages. Basic computational biology methods are known to those of ordinary skill in the art and are described in, for example, Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., $2^{nd}$ ed., 2001).

The functional modules of certain embodiments of the aspects described herein include a determination module, a storage device, a comparison module and a display module. The functional modules can be executed on one, or multiple, computers, or by using one, or multiple, computer networks or computer systems.

In some aspects, provided herein are computer systems that can be used to determine if a subject is likely to have or be at risk of chronic kidney disease or proteinuria. In some embodiments, a computer system is connected to a determination module and is configured to obtain output data from a determination module regarding a biological sample, where the determination module is configured to detect the levels of ROBO2 protein in a biological sample obtained from the subject; and where the computer system comprises (a) a storage device configured to store data output from the determination module as well as reference data; where the storage device is connected to (b) a comparison module which in some embodiments, is adapted to compare the output data stored on the storage device with stored reference data, and in alternative embodiments, adapted to compare the output data with itself, where the comparison module produces report data and is connected to (c) a display module for displaying a page of retrieved content (i.e. report data from the comparison module) for the user on a client computer, wherein the retrieved content can indicate the levels of ROBO2, and/or likelihood of the subject experiencing chronic kidney disease or proteinuria in the future.

In some embodiments, the determination module has computer executable instructions to provide expression data, sequence information, information related to sequence information in computer readable form. As used herein, "sequence information" refers to any nucleotide and/or amino acid sequence, including but not limited to full-length nucleotide and/or amino acid sequences, partial nucleotide and/or amino acid sequences, or mutated sequences. Moreover, information "related to" the sequence information includes detection of the presence or absence of a sequence (e.g., detection of a mutation or deletion), determination of the concentration of a sequence in the sample (e.g., amino acid sequence expression levels, or nucleotide (RNA or DNA) expression levels), and the like. The term "sequence information" is intended to include the presence or absence of post-translational modifications (e.g. phosphorylation, glycosylation, summylation, farnesylation, and the like).

As an example, determination modules for determining ROBO2 sequence or nucleic acid expression information can include known systems for automated sequence analysis including but not limited to Hitachi FMBIO® and Hitachi FMBIO® II Fluorescent Scanners (available from Hitachi Genetic Systems, Alameda, Calif.); SPECTRUMEDIX® SCE 9610 Fully Automated 96-Capillary Electrophoresis Genetic Analysis Systems (available from SpectruMedix LLC, State College, Pa.); ABI PRISM® 377 DNA Sequencer, ABI® 373 DNA Sequencer, ABI PRISM® 310 Genetic Analyzer, ABI PRISM® 3100 Genetic Analyzer, and ABI PRISM® 3700 DNA Analyzer (available from Applied Biosystems, Foster City, Calif.); Molecular Dynamics FLUORIMAGER™ 575, SI Fluorescent Scanners, and Molecular Dynamics FLUORIMAGER™ 595 Fluorescent Scanners (available from Amersham Biosciences UK Limited, Little Chalfont, Buckinghamshire, England); GENOMYXSC™ DNA Sequencing System (available from Genomyx Corporation (Foster City, Calif.); and PHARMACIA ALF™ DNA Sequencer and Pharmacia ALFEXPRESS™ (available from Amersham Biosciences UK Limited, Little Chalfont, Buckinghamshire, England).

In some embodiments for determining sequence or protein information, determination modules include systems for protein and DNA analysis. For example, mass spectrometry systems including Matrix Assisted Laser Desorption Ionization—Time of Flight (MALDI-TOF) systems; SELDI-TOF-MS ProteinChip array profiling systems, e.g. Machines with CIPHERGEN PROTEIN BIOLOGY SYSTEM II™ software; systems for analyzing gene expression data (see for example U.S. 2003/0194711); systems for array based expression analysis, for example HT array systems and cartridge array systems available from Affymetrix (Santa Clara, Calif. 95051) AutoLoader, COMPLETE GENECHIP® Instrument System, Fluidics Station 450, Hybridization Oven 645, QC Toolbox Software Kit, Scanner 3000 7G, Scanner 3000 7G plus Targeted Genotyping System, Scanner 3000 7G Whole-Genome Association System, GENETITAN™ Instrument, GeneChip® Array Station, HT Array; an automated ELISA system (e.g. DSX® or DS2® form Dynax, Chantilly, Va. or the ENEASYSTEM III®, TRITURUS®, THE MAGO® Plus); Densitometers (e.g. X-Rite-508-Spectro Densitometer®, The HYRYS™ 2 densitometer); automated Fluorescence in situ hybridization systems (see for example, U.S. Pat. No. 6,136,540); 2D gel imaging systems coupled with 2-D imaging software; microplate readers; Fluorescence activated cell sorters (FACS) (e.g. Flow Cytometer FACSVantage SE, Becton Dickinson); radio isotope analyzers (e.g. scintillation counters), or a combination thereof.

In some embodiments of this aspect and all other aspects of the present invention a variety of software programs and formats can be used to store the biomarker protein level information on the storage device. Any number of data processor structuring formats (e.g., text file or database) can be employed to obtain or create a medium having recorded thereon the sequence information or expression level information.

The ROBO2 expression information or information related to ROBO2 expression information determined in the determination module can be read by the storage device. As used herein the "storage device" is intended to include any suitable computing or processing apparatus or other device configured or adapted for storing data or information. Examples of electronic apparatus suitable for use with the present invention include stand-alone computing apparatus, data telecommunications networks, including local area networks (LAN), wide area networks (WAN), cloud storage systems, Internet, Intranet, and Extranet, and local and distributed computer processing systems. Storage devices also include, but are not limited to: magnetic storage media, such as floppy discs, hard disc storage media, magnetic tape, optical storage media such as CD-ROM, DVD, electronic storage media such as RAM, ROM, EPROM, EEPROM and the like, cloud storage systems, general hard disks and hybrids of these categories such as magnetic/optical storage media. The storage device is adapted or configured for having recorded thereon sequence information or expression level information. Such information may be provided in digital form that can be transmitted and read electronically, e.g., via the Internet, via a cloud system, on diskette, via USB (universal serial bus), or via any other suitable mode of communication.

As used herein, "expression level information" refers to any nucleotide and/or amino acid expression level information, including but not limited to full-length nucleotide and/or amino acid sequences, partial nucleotide and/or amino acid sequences, or mutated sequences. Moreover, information "related to" the expression level information includes detection of the presence or absence of a sequence (e.g., presence or absence of an amino acid sequence, nucleotide sequence, or post translational modification), determination of the concentration of a sequence in the sample (e.g., amino acid sequence levels, or nucleotide (RNA or DNA) expression levels, or level of post translational modification), and the like.

As used herein, "stored" refers to a process for encoding information on the storage device. Those skilled in the art can readily adopt any of the presently known methods for recording information on known media to generate manufactures comprising the sequence information or expression level information.

A variety of software programs and formats can be used to store the sequence information or expression level information on the storage device. Any number of data processor structuring formats (e.g., text file or database) can be employed to obtain or create a medium having recorded thereon the sequence information or expression level information.

By providing sequence information or expression level information in computer-readable form, one can use the sequence information or expression level information in readable form in the comparison module to compare a specific sequence or expression profile with the reference data within the storage device. For example, search programs can be used to identify fragments or regions of the sequences that match a particular sequence (reference data, e.g., sequence information obtained from a control sample) or direct comparison of the determined expression level can be compared to the reference data expression level (e.g., expression level information obtained from a control sample). The comparison made in computer-readable form provides a computer readable comparison result which can be processed by a variety of means. Content based on the comparison result can be retrieved from the comparison module to indicate a specific disease or disorder, such as chronic kidney disease or proteinuria.

In some embodiments, the reference data stored in the storage device to be read by the comparison module is ROBO2 sequence or expression information data obtained from a control biological sample of the same type as the biological sample to be tested. Alternatively, the reference data are a database, e.g., a part of the entire genome sequence of an organism, or a protein family of sequences, or an expression level profile (RNA, protein or peptide). In some embodiments, the reference data are sequence information or expression level profiles that are indicative of a specific disease or disorder, such as chronic kidney disease or proteinuria.

In some embodiments, the reference data are electronically or digitally recorded and annotated from databases including, but not limited to GenBank (NCBI) protein and DNA databases such as genome, ESTs, SNPS, Traces, Celara, Ventor Reads, Watson reads, HGTS, and the like; Swiss Institute of Bioinformatics databases, such as ENZYME, PROSITE, SWISS-2DPAGE, Swiss-Prot and TrEMBL databases; the Melanie software package or the ExPASy WWW server, and the like; the SWISS-MODEL, Swiss-Shop and other network-based computational tools; the Comprehensive Microbial Resource database (available from The Institute of Genomic Research). The resulting information can be stored in a relational data base that may be employed to determine homologies between the reference data or genes or proteins within and among genomes.

By providing the levels of ROBO2 in readable form in the comparison module, it can be used to compare with the reference threshold levels of ROBO2 within the storage device. The comparison made in computer-readable form provides computer readable content which can be processed by a variety of means.

The "comparison module" can use a variety of available software programs and formats for the comparison operative to compare ROBO2 sequence or expression level information determined in the determination module to reference ROBO2 sequence or expression level data. In some embodiments, the comparison module is configured to use pattern recognition techniques to compare ROBO2 sequence or expression level data from one or more entries to one or more reference data patterns. The comparison module can be configured using existing commercially-available or freely-available software for comparing patterns, and can be optimized for particular data comparisons that are conducted. The comparison module provides computer readable information related to the sequence information that can include, for example, detection of the presence or absence of a sequence (e.g., detection of a mutation or deletion (protein or DNA), information regarding distinct alleles, detection of post-translational modification, or omission or repetition of sequences); determination of the concentration of a sequence in the sample (e.g., amino acid sequence/protein expression levels, or nucleotide (RNA or DNA) expression levels, or levels of post-translational modification), or determination of an expression profile.

In some embodiments, the comparison module permits the comparison of levels of ROBO2 from the output data of the determination module with reference threshold level data for each ROBO2.

In some embodiments, the comparison module performs comparisons with mass-spectometry spectra, for example comparisons of peptide fragment sequence information can be carried out using spectra processed in MATLB with script called "Qcealign" (see for example WO2007/022248, herein incorporated by reference) and "Qpeaks" (Spectrum Square Associates, Ithaca, N.Y.), or Ciphergen Peaks 2.1™ software. The processed spectra can then be aligned using alignment algorithms that align sample data to the control data using minimum entropy algorithm by taking baseline corrected data (see for example WIPO Publication WO2007/022248, herein incorporated by reference). The comparison result can be further processed by calculating ratios. Protein expression profiles can be discerned.

Any available comparison software can be used, including but not limited to, the Ciphergen Express (CE) and Biomarker Patterns Software (BPS) package, Ciphergen Biosystems, Inc., CA, USA. Comparative analysis can be done with protein chip system software (e.g. The Proteinchip suite for Bio-Rad Laboratories).

The comparison module, or any other module described herein, can include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application can include a configuration file which contains pointers and addresses to the various software entities that comprise the server as well as the various external and internal databases which must be accessed to service user requests. The Configuration file also directs requests for server resources to the appropriate hardware—as can be necessary should the server be distributed over two or more separate computers. In some embodiments, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). Thus, in some preferred embodiments, users can directly access data (via Hypertext links for example) residing on Internet databases using a HTML interface provided by Web browsers and Web servers.

In some embodiments, the comparison module compares gene expression profiles. For example, detection of gene expression profiles can be determined using Affymetrix Microarray Suite software version 5.0 (MAS 5.0) (available from Affymetrix, Santa Clara, Calif.) to analyze the relative abundance of a gene or genes on the basis of the intensity of the signal from probe sets, and the MAS 5.0 data files can be transferred into a database and analyzed with Microsoft Excel and GeneSpring 6.0 software (available from Agilent Technologies, Santa Clara, Calif.). The detection algorithm of MAS 5.0 software can be used to obtain a comprehensive overview of how many transcripts are detected in given samples and allows a comparative analysis of 2 or more microarray data sets.

In some embodiments, the comparison module compares protein expression profiles. Any available comparison software can be used, including but not limited to, the Ciphergen Express (CE) and Biomarker Patterns Software (BPS) package (available from Ciphergen Biosystems, Inc., Freemont, Calif.). Comparative analysis can be done with protein chip system software (e.g., The Proteinchip Suite (available from Bio-Rad Laboratories, Hercules, Calif.). Algorithms for identifying expression profiles can include the use of optimization algorithms such as the mean variance algorithm (e.g. JMP Genomics algorithm available from JMP Software Cary, N.C.).

The comparison module provides computer readable comparison result that can be processed in computer readable form by predefined criteria, or criteria defined by a user, to provide a content based in part on the comparison result that can be stored and output as requested by a user using a display module. The display module enables display of a content based in part on the comparison result for the user, wherein the content is a signal indicative of a chronic kidney disease or proteinuria. Such signal, can be for example, a display of content indicative of the presence or absence of a chronic kidney disease or proteinuria on a computer monitor, a printed page of content indicating the presence or absence of a chronic kidney disease or proteinuria from a printer, or a light or sound indicative of the presence or absence of a chronic kidney disease or proteinuria.

The content based on the comparison result can include an expression profile of one or more proteins, or an expression profile of one or more genes. In some embodiments, the content based on the comparison result is merely a signal indicative of the presence or absence of a chronic kidney disease or proteinuria based on ROBO2 protein levels.

In some embodiments, the content based on the comparison result is displayed a on a computer monitor. In one embodiment of the invention, the content based on the comparison result is displayed through printable media. In one embodiment of the invention, the content based on the comparison result is displayed as an indicator light or sound. The display module can be any suitable device configured to receive from a computer and display computer readable information to a user. Non-limiting examples include, for example, general-purpose computers such as those based on Intel PENTIUM-type processor, Apple computer and tablet devices, Motorola PowerPC, Sun UltraSPARC, Hewlett-Packard PA-RISC processors, any of a variety of processors available from Advanced Micro Devices (AMD) of Sunnyvale, Calif., or any other type of processor, visual display devices such as tablet devices, smartphone mobile devices, flat panel displays, cathode ray tubes and the like, as well as computer printers of various types.

In some embodiments, a World Wide Web browser is used for providing a user interface for display of the content based on the comparison result. It should be understood that other modules of the invention can be adapted to have a web browser interface. Through the Web browser, a user may construct requests for retrieving data from the comparison module. Thus, the user will typically point and click to user interface elements such as buttons, pull down menus, scroll bars and the like conventionally employed in graphical user interfaces. The requests so formulated with the user's Web browser are transmitted to a Web application which formats them to produce a query that can be employed to extract the pertinent information related to the sequence information, e.g., display of an indication of the presence or absence of mutation or deletion (DNA or protein); display of expression levels of an amino acid sequence (protein); display of nucleotide (RNA or DNA) expression levels; display of expression, SNP, or mutation profiles, or haplotypes, or display of information based thereon. In one embodiment, the sequence information of the reference sample data is also displayed.

In some embodiments, the display module displays the comparison result and whether the comparison result is indicative of a disease, e.g., whether the expression profile of ROBO2 is indicative of chronic kidney disease or proteinuria.

In some embodiments, the content based on the comparison result that is displayed is a signal (e.g. positive or negative signal) indicative of the presence or absence of a chronic kidney disease or proteinuria, thus only a positive or negative indication can be displayed.

Thus, provided herein are systems (and computer readable medium for causing computer systems) to perform assays and methods for determining whether an individual has a chronic kidney disease or proteinuria or a pre-disposition, for a chronic kidney disease or proteinuria based on expression profiles or sequence information.

Systems and computer readable medium, are merely an illustrative embodiments of the invention for performing assays and methods of determining whether an individual has a specific disease or disorder or a pre-disposition, for a specific disease or disorder based on expression profiles or sequence information, and is not intended to limit the scope of the invention. Variations of systems, and computer readable medium, are possible and are intended to fall within the scope of the invention.

The modules of the system or used in the computer readable medium, can assume numerous configurations. For example, function can be provided on a single machine or distributed over multiple machines.

Figure 5A:
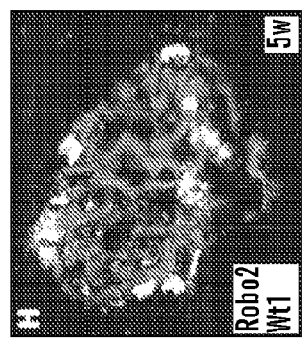
FIGS. 5A-5M demonstrate that Robo2 is expressed in the developing and adult glomeruli.
Figure 5B:
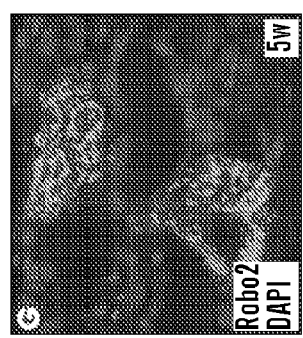
Figures 5G, 5H:
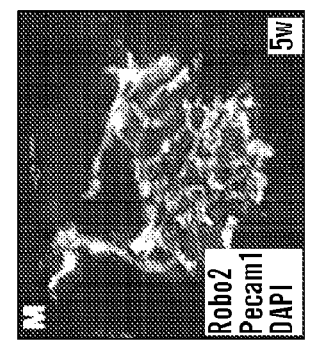
Figure 5C:
Figures 5I, 5J, 5K:
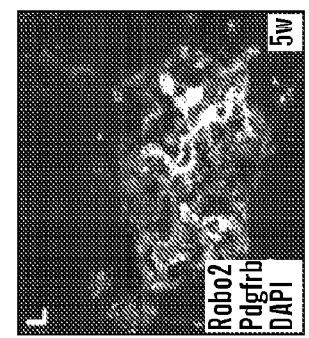
Figures 5D, 5E, 5F:
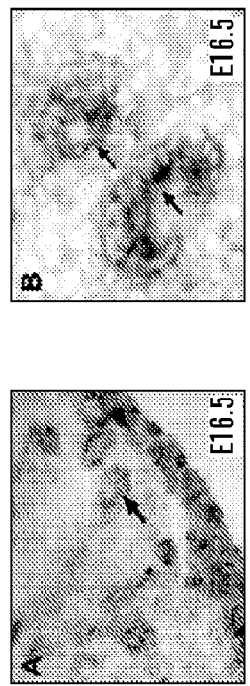
Figures 5L, 5M:
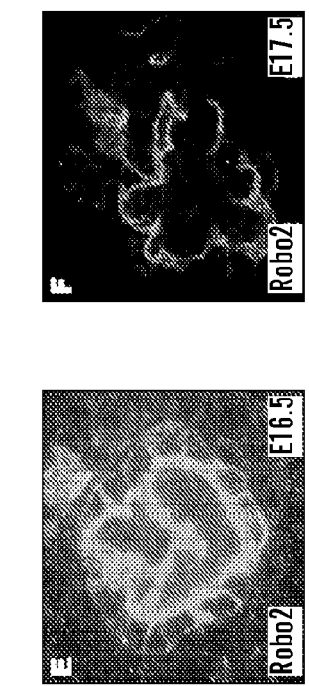

Robo2 is a Podocyte Protein Localized to the Basal Cell Surface of Mouse Podocyte During kidney development, Robo2 mRNA is expressed in the metanephric mesenchyme surrounding the arborizing ureteric bud and later in the proximal end of the S-shaped body (Piper et al., 2000), the location of primordial podocytes. To investigate whether Robo2 is also involved in podocyte maturation, in addition to its role in early kidney induction, we performed in situ hybridization and found Robo2 mRNA was expressed in the capillary loop stage of developing glomeruli of mouse embryos at embryonic day 16.5 (E16.5) (FIGS. 5A and 5B). Robo2 protein became detectable by immunofluorescence staining in the developing glomerulus around E14.5 and reached peak expression at E16.5 (FIGS. 5C-5E). Although the expression decreased after E17.5 during development (FIG. 5F), specific Robo2 expression was maintained in glomeruli after birth and was detectable in adult mice at 5 weeks of age (FIGS. 5G, 5H, 5L-5M).

Figure 1B:
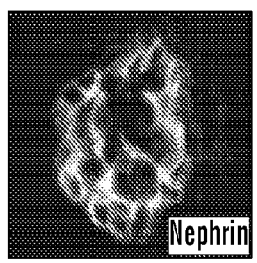
Figure 1C:
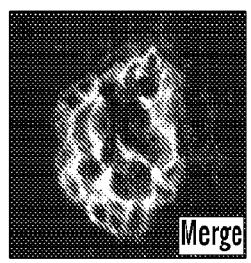
Figure 1D:
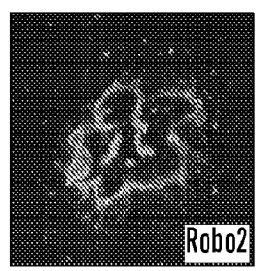
(FIGS. 1D-1F) Robo2 co-localizes with podocyte slit-diaphragm protein podocin.
Figure 1E:
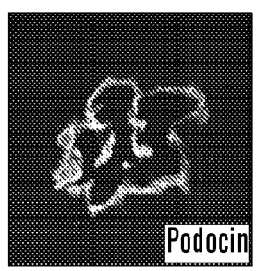
Figure 1F:
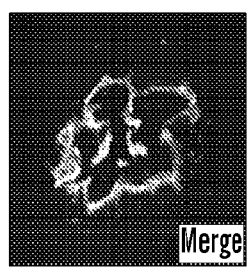
Figure 1G:
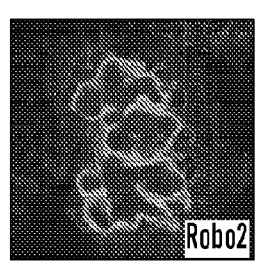
(FIGS. 1G-1I) Robo2 co-localizes with adaptor protein Nck in glomeruli.
Figure 1H:
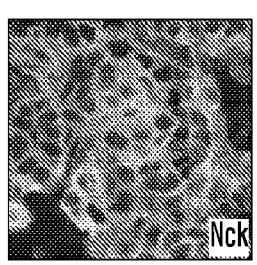
Figure 1I:
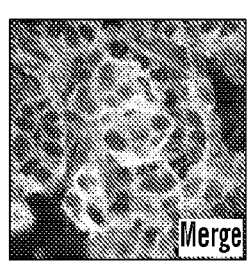
Figure 1J:
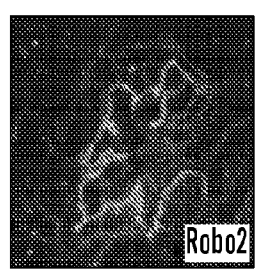
(FIGS. 1J-1L) Robo2 is expressed on the basal podocyte surface adjacent to glomerular basement membrane protein nidogen.
Figure 1K:
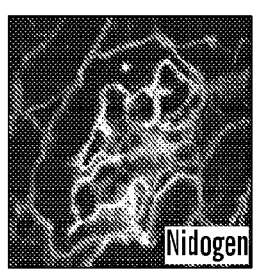
Figure 1L:
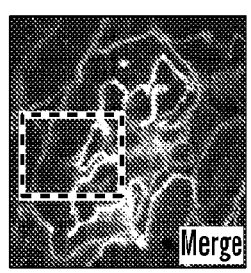
Figure 1M:
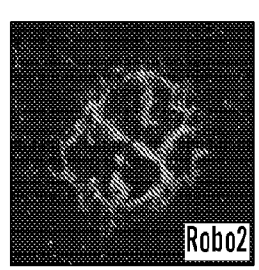
(FIGS. 1M-1O) Robo2 does not co-localize with glomerular endothelial cell protein marker Pecam1.
Figure 1N:
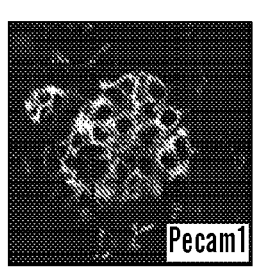
Figure 1O:
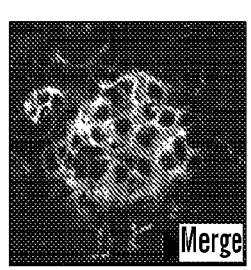
Figure 1P:
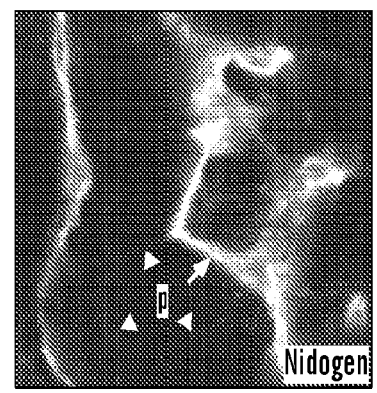
(FIG. 1P) The enlarged region boxed in (FIG. 1L) shows that Robo2 is expressed predominantly on the basal cell surface (arrow) of podocytes (p) adjacent to glomerular basement membrane marker nidogen. Robo2 is weakly expressed in the apical and lateral cell surfaces (arrowheads) of podocytes.
Figure 1Q:
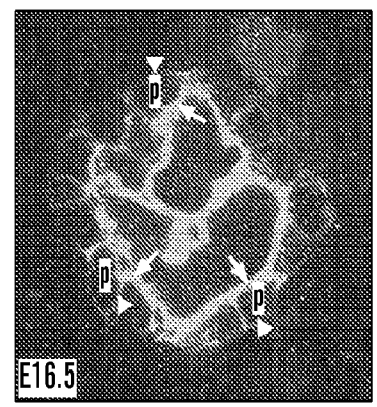
(FIG. 1Q) Robo2 is expressed predominantly on the basal cell surface (arrows) of podocytes (p) and is weakly expressed on the apical or lateral cell surfaces (arrowheads).
Figure 1R:
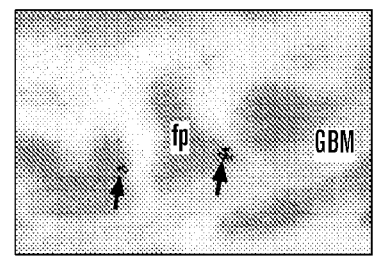

To determine the cellular localization of Robo2 in the developing glomerulus, we performed dual-label immunohistochemistry with glomerular cell type specific markers. We found that Robo2 protein was co-localized with nephrin (FIGS. 1A-1C) and podocin (FIGS. 1D-1F), two podocyte slit-diaphragm associated proteins. Robo2 was also co-expressed in the glomeruli with the nephrin-interacting adaptor protein Nck (FIGS. 1G, 1I) and with WT1, a constituent of podocyte nuclei (FIGS. 5H-5K). Dual-labeling with antibodies against nidogen, a basement membrane marker (FIGS. 1J-1L and 1P) and Pecam1, an endothelial cell marker (FIGS. 1M-1O, 5M) showed that Robo2 was localized adjacent to the external surface of the glomerular basement membrane and absent from endothelial cells. High-resolution confocal microscopy further demonstrated that subcellular Robo2 was most abundant on the basal surface of podocytes (FIG. 1Q). Immunogold electron microscopy of postnatal mouse kidneys with an antibody against the cytoplasmic domain established that Robo2 was localized to podocyte foot processes close to the cytoplasmic face of the slit-diaphragms (FIG. 1R). These results demonstrate that Robo2 is a podocyte protein and its basal subcellular localization in the foot processes indicates that it plays a role in regulating podocyte foot process structure.

Robo2 Intracellular Domain Interacts Directly with SH3 Domains of Adaptor Protein Nck Nephrin extracellular domain engagement leads to tyrosine phosphorylation of its intracellular domain by Src kinases and recruitment of the SH2 domain of the adaptor protein Nck, which in turn induces actin polymerization (Jones et al., 2006; Verma et al., 2006). Nck bears one SH2 domain in the C-terminus and three SH3 domains near the N-terminus. Actin polymerization is mediated by the SH3 domains of Nck (Rivera et al., 2004), which can recruit various cytoskeleton regulators including N-WASP and Pak (Jones et al., 2006). Previous studies have shown that the SH3 domains of the *Drosophila* Nck homolog Dreadlock (Dock) also directly interact with the intracellular domain of Robo to inhibit actin polymerization (Fan et al., 2003; Yang and Bashaw, 2006).

Figure 2A:
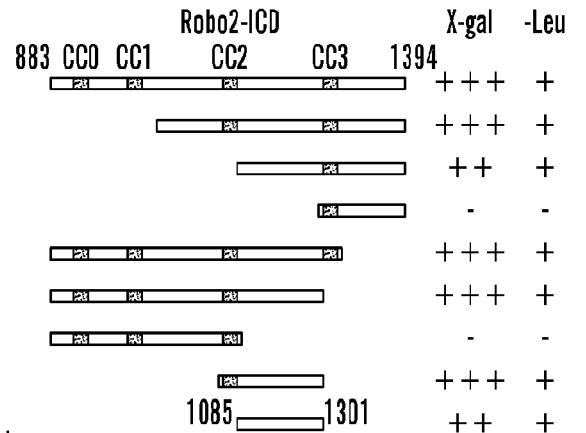
FIGS. 2A-2J demonstrate that Robo2 interacts with the adapter protein Nck and forms a complex with nephrin.
Figure 2B:
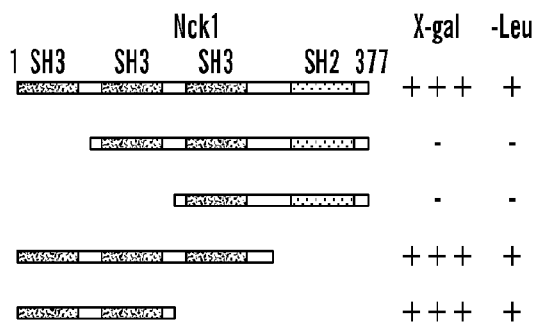
Figure 2C:
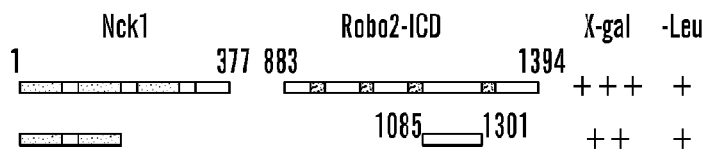

We tested whether mammalian Nck can also interact directly with Robo2 in the podocyte to regulate the F-actin cytoskeleton. To answer this question, we used a yeast two-hybrid assay to examine if Robo2 interacted with Nck. Since two mammalian Ncks (i.e. Nck1, Nck2) share similar structure and function in kidney development (Jones et al., 2006), we used Nck1 in this study and observed that the intracellular domain of Robo2 directly interacted with Nck1 (FIGS. 2A-2C). Binding site mapping in Robo2 for Nck1 showed that the sequence from amino acid 1085 to 1301, which contains 4 proline-rich motifs, was crucial for the interaction (FIGS. 2A and 2C). Absence of this proline-rich region prevented its interaction with Nck1 (FIG. 2A). Binding site mapping in Nck1 for Robo2 showed that the first two SH3 domains were required for its interaction with Robo2 because deleting either or both of them abrogated the interaction (FIG. 2B). Thus Robo2 and Nck1 interaction was mediated by two well-characterized protein domains, the SH3 domains and proline-rich motifs (FIG. 2C). CD2AP, another podocyte adaptor protein, also bears three SH3 domains in its N-terminus (Shih et al., 2001), but we did not detect any interaction between CD2AP and Robo2 in either the yeast two-hybrid or co-precipitation assays. These observations indicate that the binding between Robo2 and Nck1 in the podocyte is a specific interaction.

Full-Length Robo2 Forms a Complex with Nephrin Through Nck

Figure 2D:
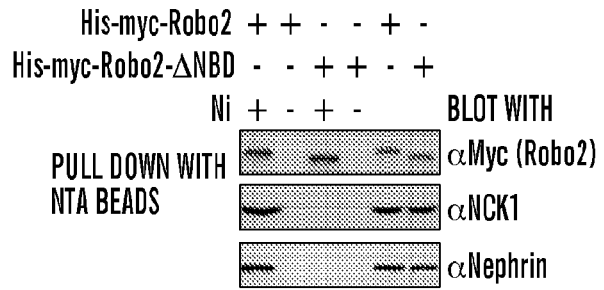
Figure 2E:
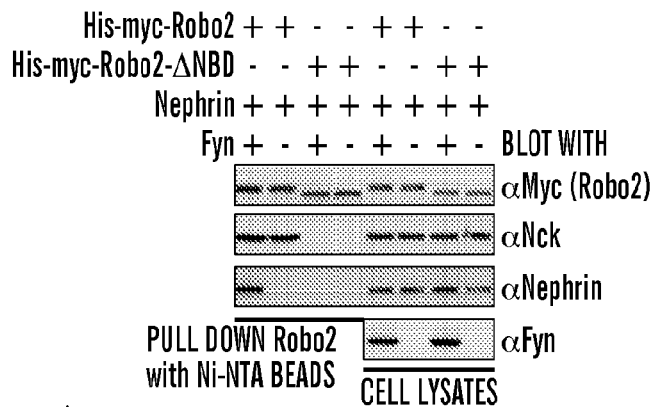
Figure 2F:
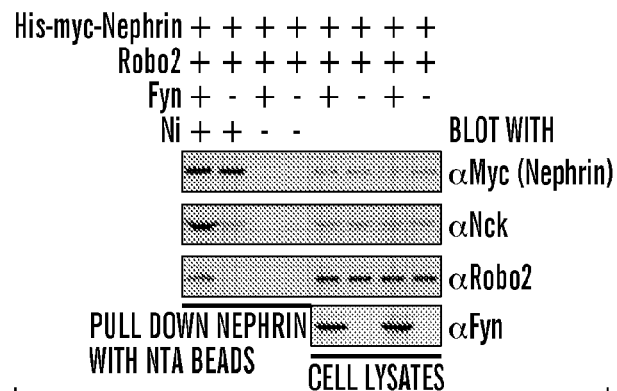
Figures 2G, 2H:
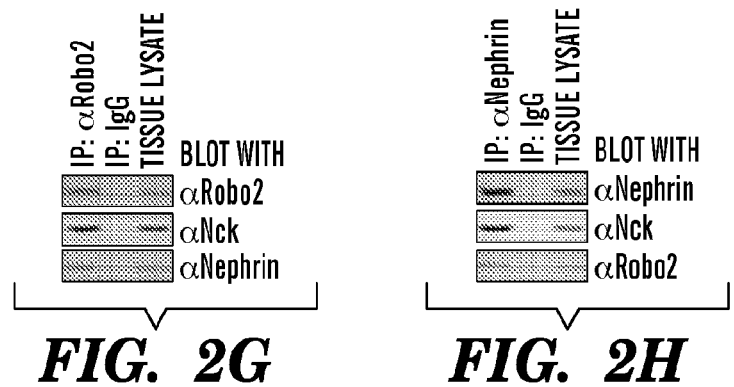

We confirmed the interaction between Robo2 and Nck by pull down and co-precipitation assays. His- and myc-tagged human full-length Robo2 (His-myc-Robo2) or his- and myc-tagged human Robo2 with a deletion of the Nck1 binding domain (His-myc-Robo2-ΔNBD) were expressed in HEK cells. Transfected HEK cells were stimulated with Slit2 conditioned medium (prepared from Slit2 stably transfected cells) to activate Robo2 and increase Nck binding (Fan et al., 2003). Nck was pulled down with His-mycRobo2 from the HEK cell lysates using Ni-NTA beads but not with His-myc-Robo2-ΔNBD (FIG. 2D). Since the SH2 domain of Nck interacts with phosphotyrosines in the nephrin cytoplasmic domain (NCD) (Jones et al., 2006; Verma et al., 2006), we examined whether Robo2 formed a complex with nephrin through Nck using a co-precipitation assay. To establish proof of principle, we co-expressed Robo2 and nephrin in HEK cells with Fyn kinase to increase nephrin phosphorylation (Verma et al., 2006). Pull-down of His-myc-Robo2 from the HEK cell lysates with Ni-NTA beads co-precipitated Nck and nephrin when Fyn was expressed (FIG. 2E). In the reverse order, pulling down His-myc-nephrin co-precipitated Nck and Robo2 when Fyn kinase was expressed (FIG. 2F). Furthermore, the precipitates prepared with the anti-Nck antibody contained both Robo2 and nephrin when Fyn was over-expressed (FIG. 6A). These data indicate that nephrin, Nck, and Robo2 form a complex in vitro. To validate these findings in vivo, we immunoprecipitated Robo2 from newborn mouse kidney lysates and found that Nck and nephrin were co-precipitated (FIG. 2G). Conversely, the precipitates prepared with the anti-nephrin antibody also contained Nck and Robo2 (FIG. 2H). Since nephrin is uniquely expressed in podocytes, and Nck and Robo2 are also localized in these cells in the kidney, these results indicate that nephrin, Nck, and Robo2 are able to form a complex in podocytes.

Figure 2I:
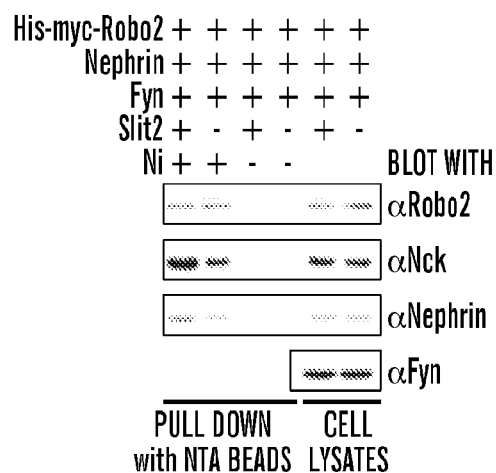
Figure 2J:
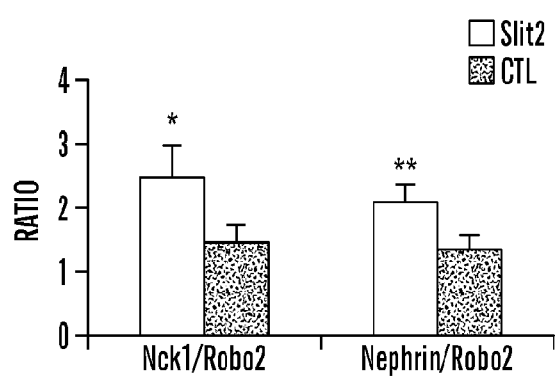

To determine the role of Slit2 in the formation of the Robo2-Nck-nephrin protein complex, His-myc-Robo2, nephrin, and Fyn were co-expressed in HEK cells that were stimulated with Slit2 conditioned medium or control conditioned medium without Slit2 prior to co-precipitation (FIG. 2I). We observed that Slit2 stimulation increased Robo2 binding to Nck and complex formation with nephrin. Both ratios of Nck1 versus Robo2 and nephrin versus Robo2 were increased after Slit2 stimulation (FIG. 2J). Consistent with this finding, we observed that Slit2 was strongly expressed in newborn mouse glomeruli (FIGS. 6B, 6C).

Slit2-Robo2 Signaling Inhibits Nephrin-Induced Actin Polymerization

Since Slit binds Robo to recruit Dock and srGAPs to inhibit actin polymerization (Fan et al., 2003), we wished to test whether Robo2 also recruits Nck to inhibit actin polymerization in mammalian cells, an opposite role to nephrin that promotes actin polymerization. To address this question, we studied actin polymerization by analyzing F-actin tails in cells expressing the CD16/7-NCD chimeric protein as previously described (Jones et al., 2006; Verma et al., 2006). This model utilizes the extracellular and transmembrane domains of the human immunoglobulin Fc receptors CD 16 and CD7 fused to the nephrin cytoplasmic domain (NCD). CD 16/7-HA, in which NCD was replaced by an HA tag, was used as a negative control. These chimeric proteins were co-expressed with Robo2 in HEK cells and clustered by treatment with anti-CD16 antibody and a secondary antibody conjugated to rhodamine. We first examined if clustering of the nephrin cytoplasmic domain could recruit Robo2. We observed that engagement of CD 16/7-NCD brought Robo2 into the clusters since most of the Robo2 co-localized with the CD16/7-NCD clusters (FIGS. 6D-6H). However, no colocalization of the Robo2 was observed either with the CD16/7-HA control (FIG. 6E) or with the Robo2-ΔNBD construct (FIG. 6G), in which the Robo2 Nck binding domain (NBD) was deleted. Interestingly, in the absence of Slit2, colocalization of CD16/7-NCD and Robo2 was significantly reduced (FIG. 6I). These data provide further evidence that the nephrin cytoplasmic domain is able to complex with the Robo2 intracellular domain in the presence of Slit2 and validates the model to determine if the formation of a Robo2-Nck-nephrin complex affects actin polymerization.

Figure 3A:
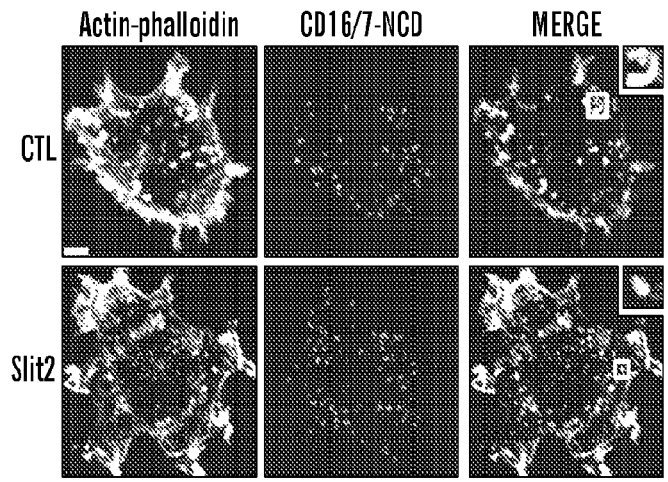
FIGS. 3A-3G demonstrate that Slit2-Robo2 signaling inhibits nephrin-mediated actin polymerization.
Figure 3B:
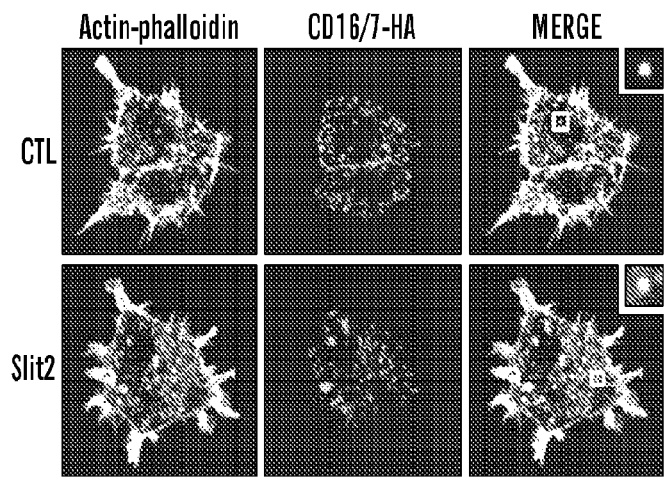
Figure 3C:
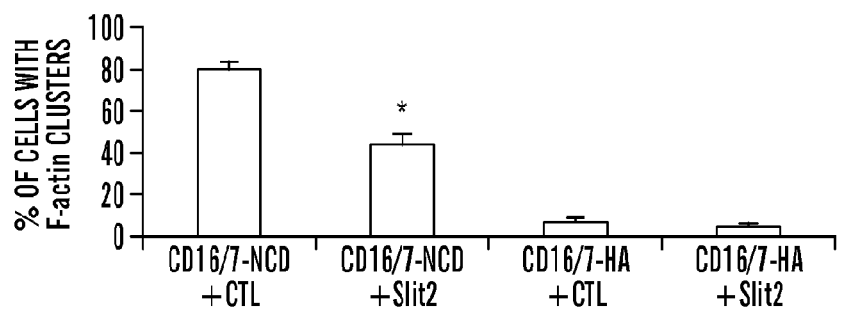
Figure 7A:
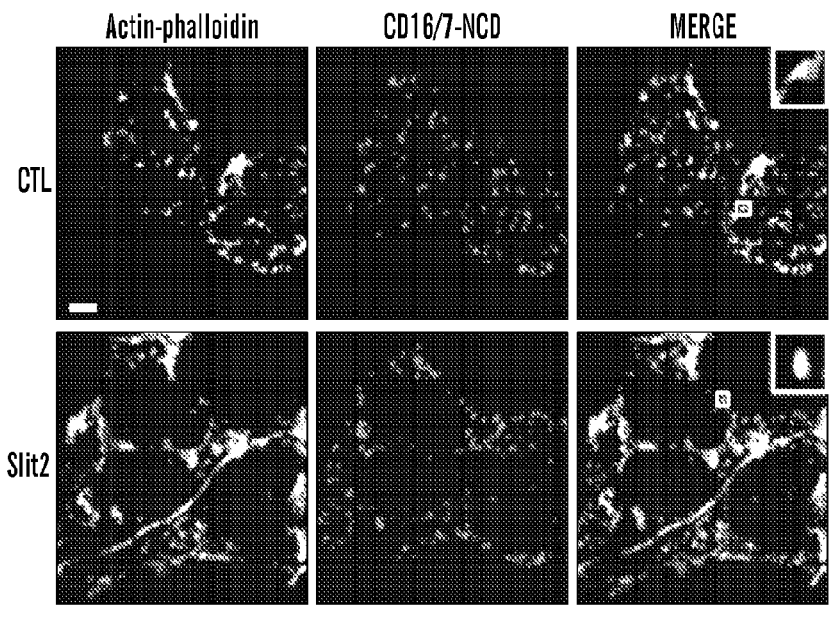
Figure 7B:
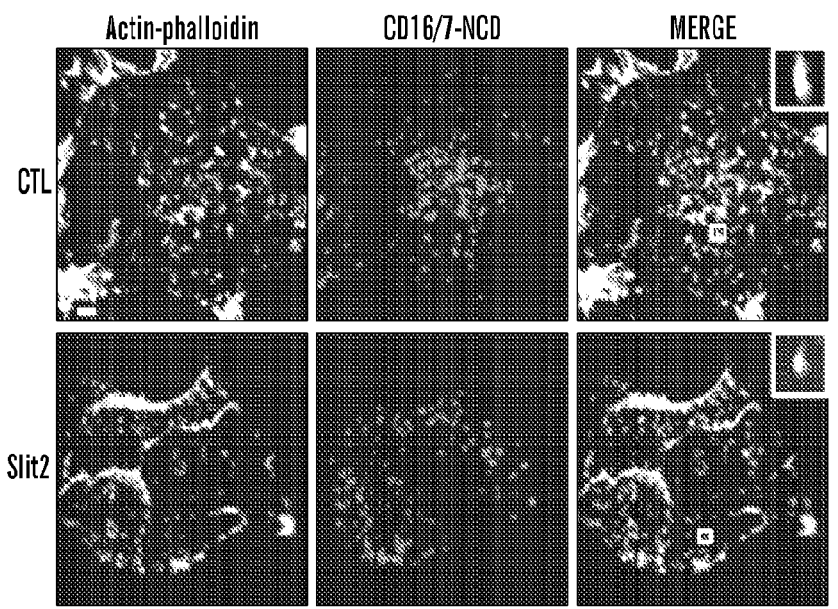

HEK cells expressing CD16/7-NCD and Robo2 were stimulated with Slit2 or control conditioned medium without Slit2 while clustered by the anti-CD16 antibody. Actin polymerization was evaluated by quantifying the number of HEK cells with visible F-actin tails (Rivera et al., 2004). We observed that ~80% of the CD16/7-NCD clustered cells formed F-actin tails that could be revealed by phalloidin staining as previously reported (Jones et al., 2006; Verma et al., 2006). Upon Slit2 stimulation, however, the number of cells with F-actin tails was significantly reduced to approximately 40% (FIGS. 3A and 3C). Only a few cells were observed to contain shorter F-actin tails when the control CD16/7-HA proteins were clustered (FIGS. 3B and 3C). To further investigate whether this inhibition of actin polymerization required Nck, we repeated this assay using Robo2 without Nck binding domain (Robo2-ΔNBD) to determine if blocking of Nck binding to Robo2 would prevent Slit2-Robo2 inhibition on nephrin-induced actin polymerization. CD16/7-NCD was co-expressed with either full-length Robo2 (FIG. 7A) or Robo2-ΔNBD (FIG. 7B) in HEK cells. We observed that deletion of Nck binding domain in Robo2 significantly compromised Slit2-Robo2 inhibition on nephrin-induced actin polymerization (FIG. 7C).

Figure 3D:
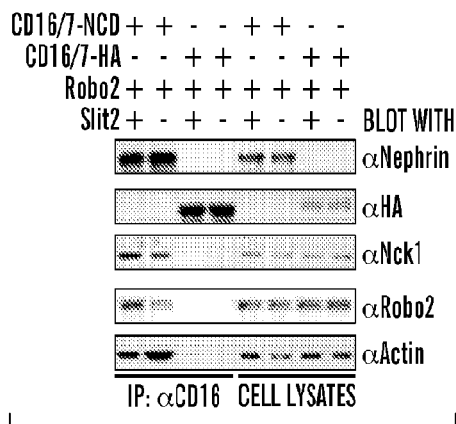
Figure 3E:
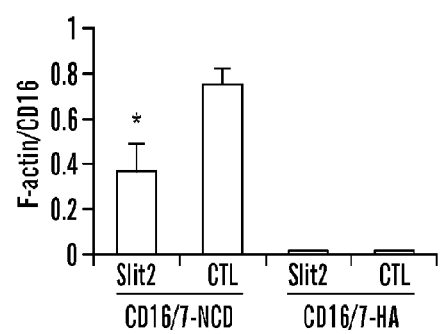
Figure 3F:
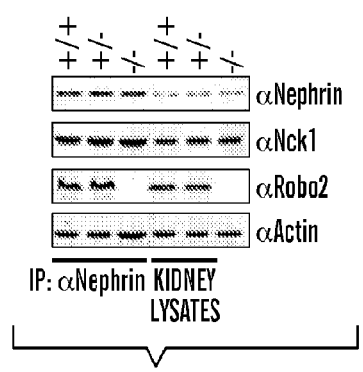
Figure 3G:
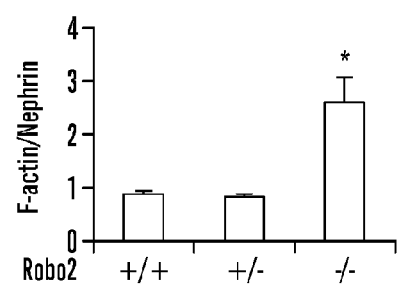

Previous study has shown that nephrin is linked to the F-actin cytoskeleton (Yuan et al., 2002). To determine if Slit2-Robo2 signaling could inhibit F-actin associated to nephrin, we immunoprecipitated CD16/7-NCD and CD16/7-HA with anti-CD16 antibody and examined the amount of F-actin in the precipitates by Western blot. We observed that the abundance of F-actin associated with nephrin was significantly reduced upon Slit2 stimulation (FIGS. 3D and 3E). Conversely, in vivo immunoprecipitation assay showed that F-actin associated with nephrin immunoprecipitated by an anti-nephrin antibody from Robo2 newborn null mouse kidneys was significantly increased compared with that from wild type or Robo2 heterozygous mouse kidneys (FIGS. 3F and 3G). Taken together, these results indicate that Slit2-Robo2 signaling inhibits nephrin-induced actin polymerization.

Loss of Robo2 in Podocytes Causes Altered Foot Process Structure in Mice

We and others have previously shown that almost all Robo2 homozygous null mice in mixed genetic background die shortly after birth due to a severe CAKUT phenotype (Grieshammer et al., 2004; Lu et al., 2007; Wang et al., 2011). After breeding mice with a Robo2$^{del5}$ mutant allele for five generations onto C57BL/6 genetic background, mating of Robo2$^{del5/+}$ heterozygous parents revealed three Robo2$^{del5/del5}$ homozygous null mice that survived to 3 weeks (among a total of 160 mice analyzed at weaning). To determine if Robo2 was required for podocyte foot process formation during development, we examined the ultrastructure of glomeruli in Robo2 null mice at birth and 3 weeks of age. Although the podocyte body, foot processes and slit-diaphragm were formed at birth, transmission electron microscopy showed focal foot process effacement in newborn Robo2$^{del5/del5}$ homozygous null mice (FIGS. 8A-8F). By scanning electron microscopy, we observed irregular interdigitating foot processes in Robo2$^{del5/del5}$ homozygous null mice at birth and 3 weeks of age (FIGS. 4A-4H). These findings indicate that Robo2 is required for normal podocyte foot process patterning during kidney development.

To examine the role of Robo2 in the maintenance of foot process structure in mature glomeruli, we generated podocyte specific Robo2 knockout mice by crossing conditional Robo2$^{flox/flox}$ mice with Robo2$^{del5/+}$; Tg$^{Nphs2-Cre/+}$ heterozygous mice carrying a podocin-Cre transgene. Twenty podocyte specific Robo2 mutant mice with Robo2$^{del5/flox}$; Tg$^{Nphs2-Cre/+}$ genotype and 20 littermate control mice were analyzed up to one year of age. Podocyte specific Robo2 knockout mice were viable and fertile. However, they displayed unusually broad podocyte foot processes and focal segmental foot process effacement at one month (FIGS. 4I-4M). At 6 weeks of age the mutant mice developed significant microalbuminuria, which was detected by both ELISA and Western blot analyses (FIGS. 4N and 4O). In addition, scanning electron microscopy revealed foot process patterning defects in Robo2 podocyte specific knockout mice. Instead of orderly zipper-like interdigitating secondary foot processes in the wild-type, Robo2 podocyte specific knockout mice displayed irregular and disorganized foot process interdigitation patterning at one month (FIGS. 8G-8J). These defects became more obvious over time. At seven months of age, overtly disorganized, shorter, and meandering foot processes were observed in Robo2 podocyte specific knockout mice (FIGS. 8K-8N), which were similar to the phenotype of three-week old Robo2 null mice. Although Robo2 podocyte specific knockout mice displayed normal podocyte number, matrix deposition was significantly increased in glomeruli (FIGS. 8O-8T, Tables 1 and 2). These morphological changes indicate that Robo2 plays a role in regulating and maintain glomerular podocyte foot process structure.

Loss of Robo2 Alleviates the Podocyte Structural Defect in Nephrin Null Mice

Figure 4P:
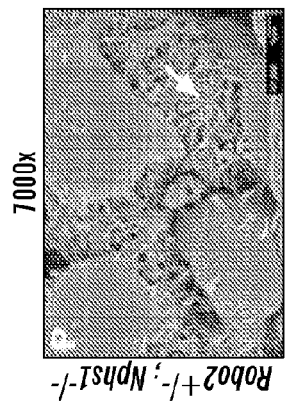
(FIGS. 4P and 4Q) Representative scanning electron microscope images show disrupted interdigitating podocyte foot processes that resemble disorganized cellular protrusions (arrows) in the Nphs1−/− single homozygous newborn mouse kidney. Scale bars: 1 μm.
Figure 4Q:
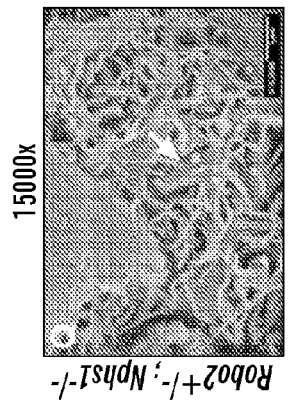
Figure 4T:
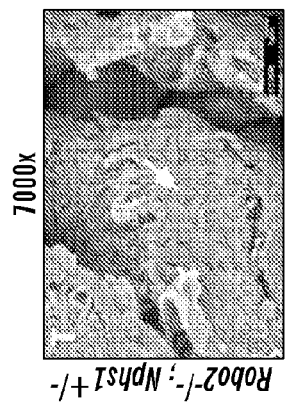
(FIGS. 4T and 4U), Glomeruli from Robo2−/− single homozygous newborn mice display irregular and broader foot processes but extensive interdigitating pattern formation (arrows).
Figure 4U:
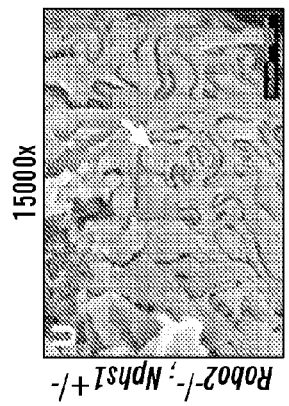
Figure 4R:
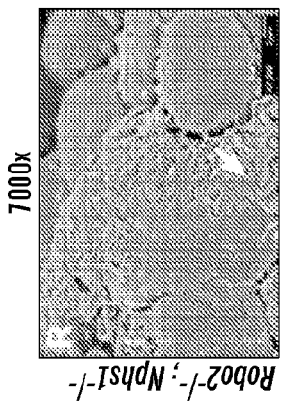
(FIGS. 4R and 4S) Glomeruli from Nphs1−/−Robo2−/− double homozygous newborn mice exhibit restored interdigitating foot processes (arrows), indicating alleviation of nephrin null phenotype by knocking out Robo2.
Figure 4S:
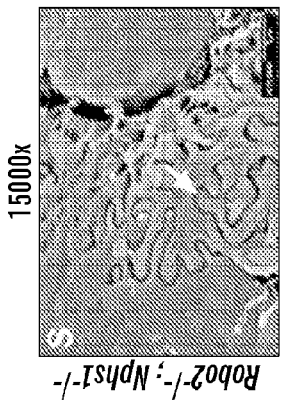
Figure 4V:
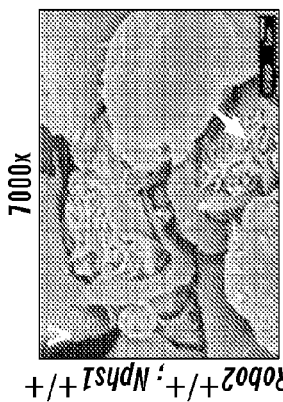
Figure 4W:
Figure 8G:
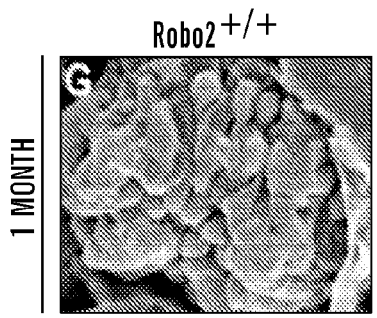
(FIGS. 8G-8N) Abnormal podocyte foot process patterns in Robo2 podocyte-specific knockout mice.
Figure 8H:
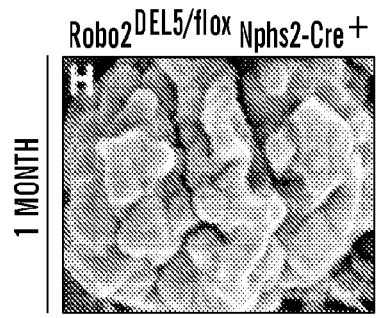
Figure 8I:
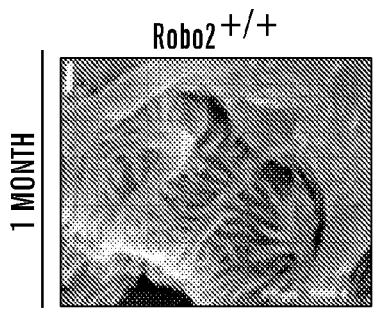
Figure 8J:
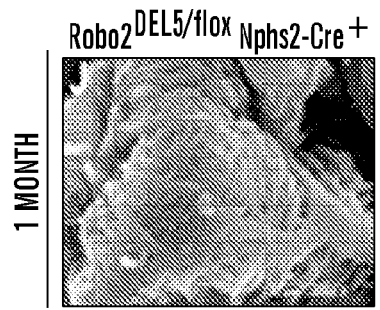
Figure 8K:
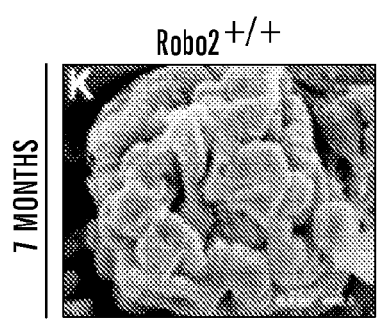
Figure 8L:
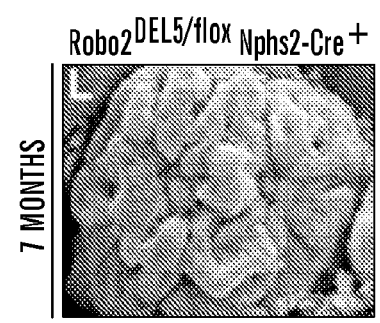
Figure 8M:
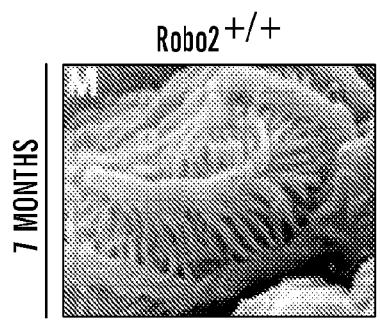
Figure 8N:
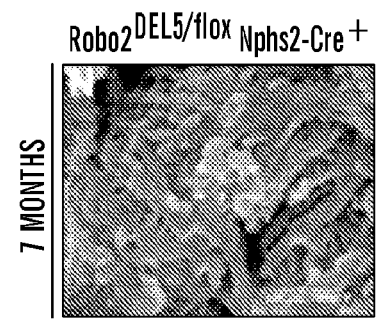
Figure 8O:
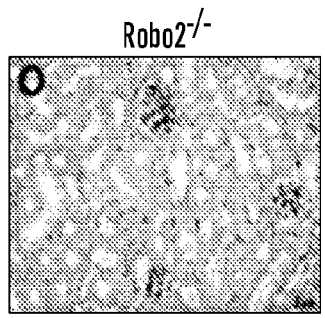
(FIGS. 8O-8T) Glomerular morphology in Robo2 podocyte-specific knockout mice.
Figure 8P:
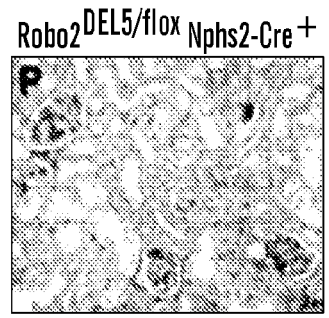
Figure 8Q:
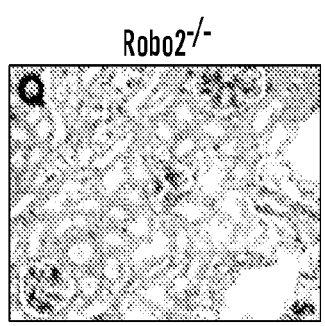
Figure 8R:
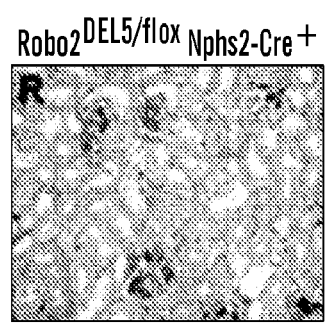
Figure 8S:
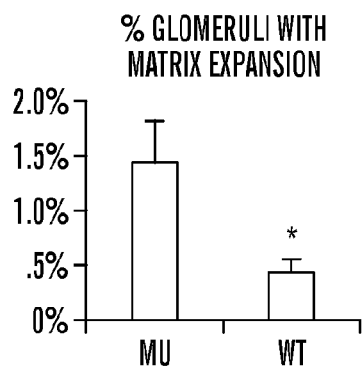
Figure 8T:
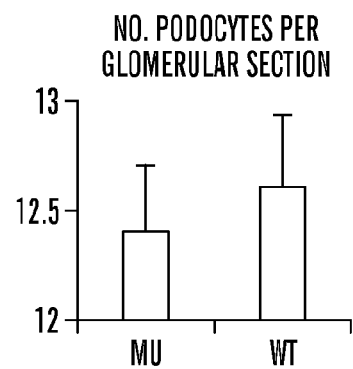
Figure 8U:
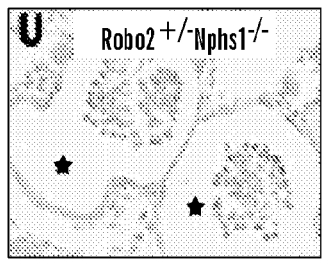
(FIGS. 8U-8Y) Glomerular phenotype in Robo2 and Nphs1 double knockout mice.
Figure 8V:
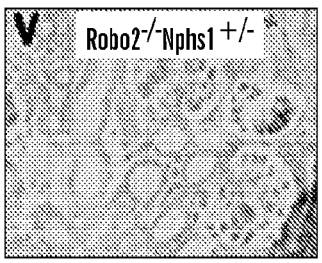
Figure 8W:
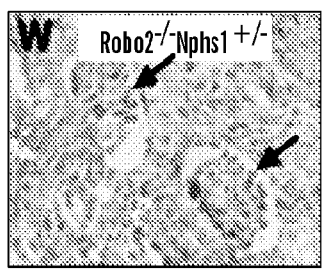
Figure 8X:
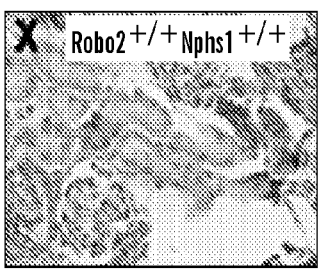
Figure 8Y:
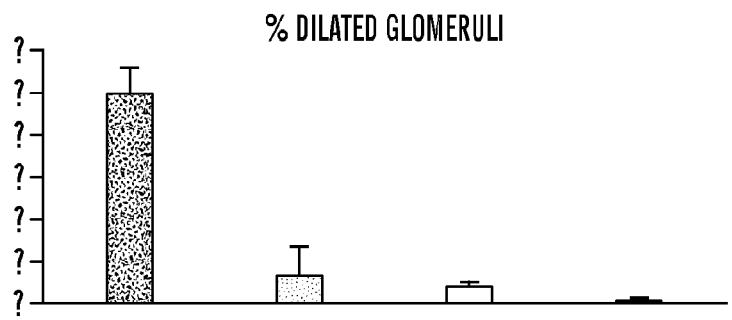

Nephrin homozygous mice develop a characteristic phenotype with dilation of the Bowman's space, abnormally broad foot processes, absence of glomerular slit-diaphragms, and significant proteinuria (Done et al., 2008; Hamano et al., 2002). Since Robo2 formed a complex with nephrin, and Slit2-Robo2 signaling inhibited nephrin-induced actin polymerization, we wondered if loss of Robo2 would modify the podocyte phenotype in nephrin null mice. To test this hypothesis of a possible genetic interaction between Robo2 and nephrin, we generated both germline Robo2$^{-/-}$; Nphs1$^{-/-}$ and podocyte specific Robo2$^{flox/flox}$; Tg$^{Nphs2-Cre/+}$; Nphs1$^{-/-}$ double Robo2-nephrin knockout mice. Like Nphs1$^{-/-}$ single homozygote, both Robo2$^{-/-}$; Nphs1$^{-/-}$ (4/4, 100%) and Robo2$^{flox/flox}$; Tg$^{Nphs2-Cre/+}$; Nphs1$^{-/-}$ (3/3, 100%) double knockout mice died within 10 hours after birth. Histological analysis, however, revealed that the morphology of glomeruli in the Robo2$^{-/-}$; Nphs1$^{-/-}$ double homozygous mice appeared relatively normal compared with the phenotype in Nphs1$^{-/-}$ single nephrin homozygous mice, which had a dilated Bowman's space (FIGS. 8U-8X). The number of glomeruli with dilated Bowman's space was significantly reduced in Robo2$^{-/-}$; Nphs1$^{-/-}$ double homozygous mice (2/55, 3.6%) compared with nephrin single null mice (31/122, 25.4%) (FIG. 8Y and Table 3). In addition, analysis of glomerular ultrastructure by scanning electron microscopy showed that the interdigitating podocyte foot process structure was observed in only 1 (6.67%) of 15 glomeruli from nephrin single homozygous mice (FIGS. 4P and 4Q) compared with 100% in Robo2$^{-/-}$ single homozygotes (FIGS. 4T and 4U) and wild-type controls (FIGS. 4V and 4W). Remarkably, the interdigitating pattern of the podocyte foot processes was restored in 12 (75%) of 16 glomeruli from Robo2$^{-/-}$; Nphs1$^{-/-}$ double homozygous newborn mouse kidneys (FIGS. 4R and 4S, Table 4), indicating that a concomitant loss of Robo2 and nephrin alleviated the podocyte foot process structural phenotype in these mice. These findings indicate that the Robo2-Nck-nephrin physical interactions described above have a substantial effect on podocyte foot process morphology in vivo when the levels of expression of Robo2 and nephrin are genetically altered.

Podocytes exhibit a remarkable degree of plasticity. During development they differentiate from simple cuboidal epithelial cells into the elaborate process-bearing cells that we recognize as mature podocytes (Reeves et al., 1978). This plasticity is retained after maturation. It is seen most graphically as reversible foot process effacement following experimental surface charge neutralization with protamine sulfate and restoration with heparin (Seiler et al., 1975) and during relapse and remission of proteinuria in children with minimal change disease (Nachman et al., 2008). More subtle changes in foot processes probably occur under physiological conditions in response to positive and negative signals in the form of hemodynamic, hormonal or paracrine stimuli. Given the abundance of F-actin in the foot processes, it is likely, without wishing to be bound or limited by theory, that such stimuli bring about those subtle changes in response to positive and negative signals transduced to the F-actin cytoskeleton. Too much and unbalanced positive signals may lead to disease phenotype. Indeed, although a physiological ligand has yet to be identified, it is clear that clustering and phosphorylation of nephrin induces actin polymerization by recruiting Nck, a mechanism that can be involved in the proteinuria induced in rats by a nephritogenic monoclonal antibody to the extracellular domain of nephrin (Topham et al., 1999) and in cases of congenital nephrotic syndrome that develop anti-nephrin alloantibodies after renal transplantation (Patrakka et al., 2002).

Figure 8Z:
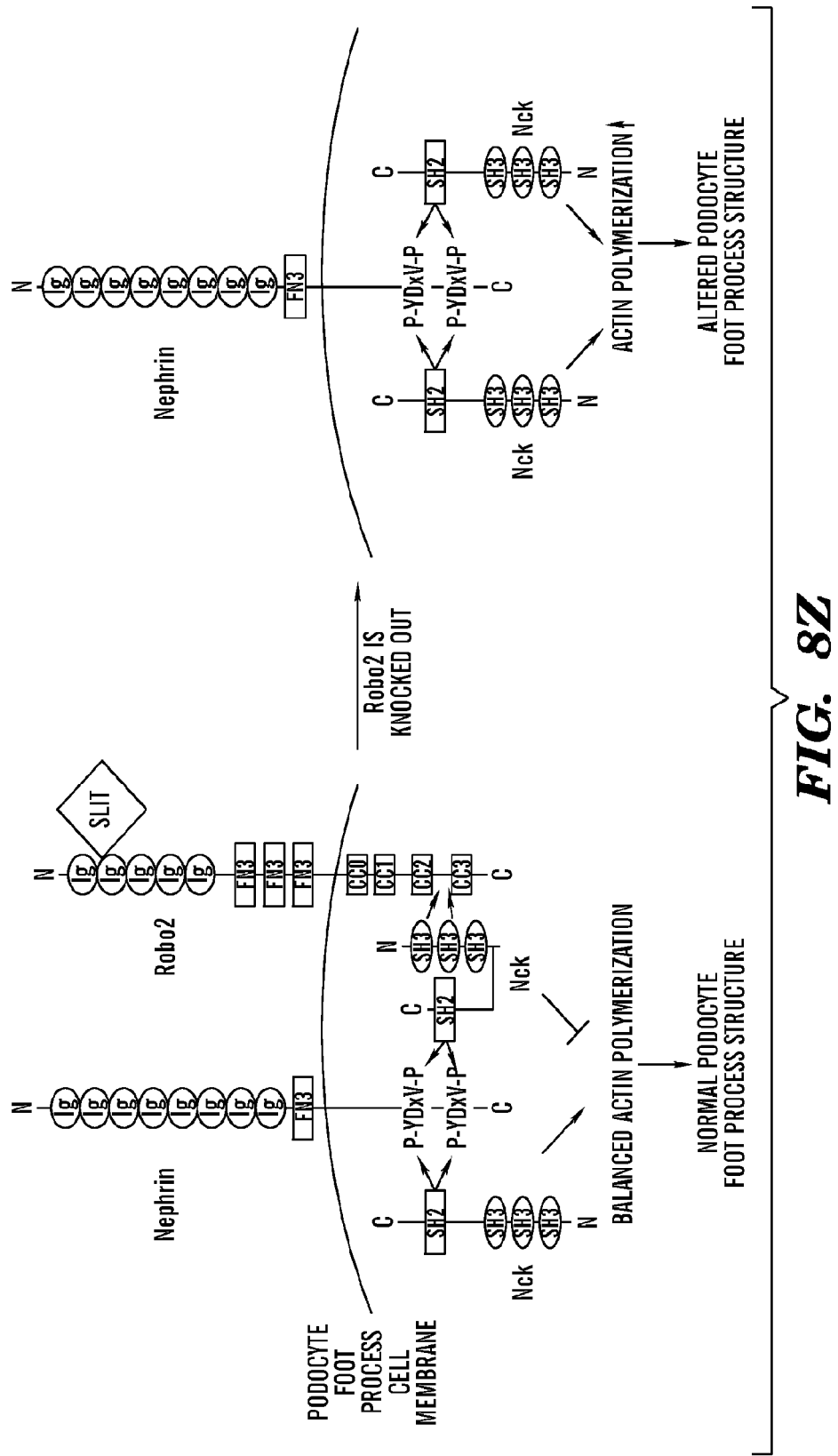

Our studies described herein reveal another level of negative regulation of podocyte actin polymerization in which Robo2, when bound by Slit, inhibits nephrin-induced actin polymerization. We propose, without wishing to be bound or limited by theory, that Slit-Robo2 signaling can inhibit nephrin-induced actin polymerization to maintain normal podocyte foot process structure as follows: Under physiological conditions (e.g. during foot process development), nephrin engagement leads to phosphorylation of the intracellular Y1191/1208/1232 to which the Nck SH2 domain binds (Jones et al., 2006; Verma et al., 2006). Nck in turn recruits cytoskeleton regulators such as N-WASP through its SH3 domains to promote actin polymerization for podocyte foot-process extension or spreading (FIG. 8Z). Local secretion and binding of Slit increases the interaction of Robo2 with Nck through its proline rich region and the first two SH3 domains of Nck. Sequestering the first two SH3 domains of Nck by Robo2 would inhibit nephrin-Nck mediated actin polymerization and decrease F-actin associated with nephrin to maintain a dynamic and balanced F-actin cytoskeleton and normal podocyte foot process structure (FIG. 8Z). In addition to direct inhibition of nephrin induced actin polymerization through Nck, Slit-Robo2 signaling can inactivate actin polymerization through other pathways, such as recruiting Ena, Abl, srGAPs to negatively regulate F-actin cytoskeleton as previously reported (Bashaw et al., 2000; Wong et al., 2001). In the absence of Slit2-Robo2 signaling (e.g., when Robo2 is knocked out), the inhibitory effects of Robo2 on nephrin induced polymerization is lost. The SH3 domains of Nck are able to interact with downstream cytoskeletal regulators to increase actin polymerization (FIG. 8Z), which can explain the altered podocyte foot process structure identified in Robo2 mutant mice. Our results described herein thus support a mechanism whereby Slit-Robo signaling can regulate podocyte plasticity by negatively regulating F-actin cytoskeleton, which is similar to the role of Slit-Robo signaling in axon growth cone pathfinding (Guan and Rao, 2003). The pathological finding of increased matrix deposition in the Robo2 mutant mouse glomeruli likely represents a secondary response.

Although it is clear from our studies described herein that Robo2 localizes to the basal surface of podocytes and forms a complex with other established foot process slit-diaphragm proteins through its intracellular domain, it remains uncertain if it actually forms part of the slit-diaphragm itself. Interestingly, the extracellular domain of Robo2 resembles that of nephrin, which has eight immunoglobulin (Ig)-like motifs and one fibronectin domain whereas Robo2 has five Ig-like motifs and three fibronectin domains (FIG. 8Z) (Tryggvason et al., 2006). We have tested the interaction between the intracellular domain of Robo2 and the cytoplasmic domain of nephrin in the yeast two-hybrid assay. Our biochemical data (FIGS. 2E and 2F) also did not support a direct interaction between these two receptors in vitro. However, it is possible that the extracellular domain of Robo2 can associate with the extracellular domain of nephrin in vivo on the cell membranes of adjacent foot processes through a trans-interaction in the slit-diaphragm.

We found that Robo2 homozygous null and podocyte specific knockout mice developed an altered foot process interdigitating pattern, a phenotype that is different from that of the nephrin null mice (Hamano et al., 2002; Done, 2008). This is not surprising since nephrin and Robo2 play opposite roles in regulating podocyte F-actin cytoskeleton. While nephrin signaling induces localized actin polymerization, Slit2-Robo2 signaling acts as a negative regulator on actin polymerization to maintain podocyte foot process plasticity and dynamics. It is noteworthy that a similar foot process organization defect is observed in mice in which the actin-depolymerizing factor Cofilin-1, another negative regulator of the F-actin cytoskeleton in podocytes, is knocked out (Garg et al., 2010). This indicates that the absence of either an actin polymerization promoting factor such as nephrin signaling or an inhibitory factor such as Robo2 signaling will affect the normal structure of podocytes. Thus the balance between positive and negative F-actin cytoskeleton regulators in podocytes is important to maintain normal foot process structure. Regaining this balance by knocking out both positive (nephrin) and negative (Robo2) signals can explain the restoration of podocyte foot process interdigitation and milder glomerular phenotype in the Robo2-nephrin double knockout mice. Our studies described herein demonstrate the dual roles of nephrin as an essential component of the slit-diaphragm to control glomerular permselectivity on the one hand (Tryggvason et al., 2006) and as a regulator of foot process morphology through its interaction with the actin cytoskeleton (Jones et al., 2006; Verma et al., 2006) on the other. While Robo2 signaling clearly counters the positive signaling effects of nephrin on the foot processes, it remains to be determined if it also influences slit-diaphragm integrity.

Accordingly, as described herein, we have identified Robo2 as a new component of the podocyte intercellular junction in the kidney. We have demonstrated interactions between Robo2 and nephrin using biochemical, functional, and genetic techniques and have shown that Slit2-Robo2 signaling inhibits nephrin-induced actin dynamics. Our results indicate that Robo2 signaling acts as a negative regulator on nephrin to modulate podocyte foot process architecture. This study extends our understanding of the role of Slit-Robo signaling and identifies a novel crosstalk mechanism by which guidance cue receptor Robo might influence F-actin cytoskeleton dynamics.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology, and molecular biology can be found in The Merck Manual of Diagnosis and Therapy, 18th Edition, published by Merck Research Laboratories, 2006 (ISBN 0-911910-18-2); Robert S. Porter et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006. Definitions of common terms in molecular biology are found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl Eds., Academic Press Inc., San Diego, USA (1987); Current Protocols in Molecular Biology (CPMB) (Fred M. Ausubel, et al. ed., John Wiley and Sons, Inc.), Current Protocols in Protein Science (CPPS) (John E. Coligan, et. al., ed., John Wiley and Sons, Inc.) and Current Protocols in Immunology (CPI) (John E. Coligan, et. al., ed. John Wiley and Sons, Inc.), which are all incorporated by reference herein in their entireties.

As used herein, the term "comprising" means that other elements can also be present in addition to the defined elements presented. The use of "comprising" indicates inclusion rather than limitation.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Further, unless otherwise required by context, singular terms shall include pluralities and plural terms shall include the singular. As used in this specification and the appended claims, the singular forms "a," "an," and the include plural references unless the context clearly dictates otherwise. Thus for example, references to "the method" includes one or more methods, and/or steps of the type described herein and/or which will become apparent to those persons skilled in the art upon reading this disclosure and so forth.

Other than in the operating examples, or where otherwise indicated, all numbers expressing quantities of ingredients or reaction conditions used herein should be understood as modified in all instances by the term "about." The term "about" when used in connection with percentages can mean±1%.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

All patents and other publications identified are expressly incorporated herein by reference for the purpose of describing and disclosing, for example, the methodologies described in such publications that could be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Embodiments of the various aspects described herein can be illustrated by the following numbered paragraphs:

2. A method for the treatment of chronic kidney disease in a subject in need thereof, comprising administering to a subject having or at risk for a chronic kidney disease a therapeutically effective amount of a composition comprising a ROBO2 inhibitor.
3. A method for the reduction of proteinuria in a subject in need thereof, comprising administering to a subject having or at risk for proteinuria a therapeutically effective amount of a composition comprising a ROBO2 inhibitor.
4. The method of any one of paragraphs for 2, wherein the ROBO2 inhibitor is a blocking antibody or antigen-binding fragment thereof specific for ROBO2, an antisense molecule specific for ROBO2, a short interfering RNA (siRNA) specific for ROBO2, a small molecule inhibitor of ROBO2, a ROBO2 inhibitory polypeptide, or a ROBO2 structural analog.
5. The method of any one of paragraphs 1-3, wherein the ROBO2 inhibitor blocks or reduces binding of ROBO2 to SLIT, to Nck, or to both.
6. The method of any one of paragraphs 1-4, wherein the ROBO2 inhibitor is specific for the Ig1 SLIT binding domain, the Ig1 and Ig2 SLIT binding domains, the Nck intracellular binding domain, or any combination thereof.
7. The method of paragraph 3, wherein the ROBO2 inhibitory polypeptide is a dominant negative ROBO2 fusion protein, a polypeptide comprising a ROBO2 extracellular domain without the intracellular domain, or a polypeptide comprising a ROBO2 intracellular domain without the extracellular domain.
8. The method of any one of paragraphs 1-6, wherein the subject having or at risk for a chronic kidney disease has diabetic nephropathy or high blood pressure.
9. The method of any one of paragraphs 1-7, further comprising administering to the subject an additional therapeutic agent.
10. The method of paragraph 8, wherein the additional therapeutic agent is an angiotensin-converting enzyme (ACE) inhibitor or an angiotensin II receptor blocker (ARB).
11. A method comprising:
    a. assaying a biological test sample from a subject to determine an expression level of ROBO2 polypeptide or an RNA encoding a ROBO2 polypeptide;
    b. determining whether the expression level of ROBO2 polypeptide or the expression level of the RNA encoding a ROBO2 polypeptide in the biological test sample is above a reference threshold level; and
    c. diagnosing the subject as in need of treatment or therapy for chronic kidney disease.
12. The method of paragraph 10, wherein assaying the expression level of ROBO2 polypeptide is performed using an antibody or antigen-binding fragment thereof specific for the ROBO2 polypeptide.
13. The method of paragraph 10, wherein assaying the expression level of the RNA encoding a ROBO2 polypeptide is performed using PCR or a hybridization assay.
14. The method of any one of paragraphs 10-12, wherein the biological test sample is a kidney biopsy, urine, blood, serum sample, or cells pelleted from a urine sample.
15. The method of any one of paragraphs 10-13, wherein the expression level of ROBO2 polypeptide or the expression level of the RNA encoding a ROBO2 polypeptide is at least 20% above the reference threshold level.
16. The method of any one of paragraphs 10-13, wherein the expression level of ROBO2 polypeptide or the expression level of the RNA encoding a ROBO2 polypeptide is at least two standard deviations above the reference threshold level.
17. An assay comprising:
    a. contacting a biological test sample isolated from a subject with a reagent that detects ROBO2 polypeptide or an RNA encoding a ROBO2 polypeptide; and
    b. measuring the level of ROBO2 polypeptide or an RNA encoding a ROBO2 polypeptide,
    c. wherein an increased level of said ROBO2 polypeptide or said RNA encoding a ROBO2 polypeptide, relative to a normal biological sample, identifies a subject having chronic kidney disease and/or progression of chronic kidney disease or proteinuria.
18. The assay of paragraph 16, wherein detecting the expression level of ROBO2 polypeptide is performed using an antibody or antigen-binding fragment thereof specific for the ROBO2 polypeptide.
19. The assay of paragraph 16, wherein detecting the expression level of the RNA encoding a ROBO2 polypeptide is performed using PCR or a hybridization assay.

20. The assay of any one of paragraphs 16-18, wherein the biological test sample is a kidney biopsy, urine, blood, serum sample, or cells pelleted from a urine sample.
21. The assay of any one of paragraphs 16-19, wherein the expression level of ROBO2 polypeptide or the expression level of the RNA encoding a ROBO2 polypeptide is at least 20% above the reference threshold level.
22. The assay of any one of paragraphs 16-19, wherein the expression level of ROBO2 polypeptide or the expression level of the RNA encoding a ROBO2 polypeptide is at least two standard deviations above the reference threshold level.
23. The assay of any one of paragraphs 16-21, wherein the subject has been diagnosed with diabetes or high blood pressure.
24. A system for determining if a subject is at risk for chronic kidney disease or proteinuria, or has chronic kidney disease comprising:
    a. a measuring module configured to determine the expression level of ROBO2 polypeptide or the expression level of the RNA encoding a ROBO2 polypeptide in a biological sample obtained from a subject;
    b. a comparison module configured to receive said expression level of ROBO2 polypeptide or the expression level of the RNA encoding a ROBO2 polypeptide determined by the measuring module and perform at least one analysis to determine whether the expression level of ROBO2 polypeptide or the expression level of the RNA encoding a ROBO2 polypeptide is greater than a pre-determined reference level or ratio, and to provide a retrieved content; and
    c. a display module for displaying a content based the data output from said comparison module, wherein the content comprises a signal indicative that the expression level or ratio of ROBO2 polypeptide or RNA is greater than the pre-determined reference level or ratio, or a signal indicative that the level or expression ratio of ROBO2 is not greater than the reference level or pre-determined ratio.
25. The system of paragraph 23, wherein the content displayed on said display module further comprises a signal indicative of the subject being recommended to receive a particular treatment regimen.
26. A system for determining if a subject is at risk for chronic kidney disease or proteinuria, or has chronic kidney disease comprising:
    a. a determination module configured to receive at least one test sample obtained from a subject and perform at least one analysis on said at least one test sample to determine the presence or absence of either of the following conditions:
        i. an expression ratio of ROBO2 greater than a pre-determined ratio, or
        ii. an expression level of ROBO2 greater than a pre-determined level
    b. a storage device configured to store data output from said determination module; and
    c. a display module for displaying a content based on the data output from said determination module, wherein the content comprises a signal indicative that the expression ratio of ROBO2 is greater than the pre-determined ratio or level of ROBO2 greater than a pre-determined level, or a signal indicative that the expression ratio of ROBO2 is not greater than the pre-determined ratio or not greater than a pre-determined level.
27. The system of paragraph 25, wherein the content displayed on said display module further comprises a signal indicative of the subject being recommended to receive a particular treatment regimen.
28. A method for treating a human subject with a risk of chronic kidney disease or proteinuria, comprising administering a treatment or therapy to prevent the occurrence of chronic kidney disease or proteinuria to a human subject who is determined to have a level of ROBO2 protein above a reference threshold level.
29. The method of paragraph 27, wherein the level of ROBO2 protein is at least 20% above the reference level.
30. The method of paragraph 27, wherein the level of ROBO2 protein is at least two standard deviations above the reference level.
31. The method of any one of paragraphs 27-29, wherein the treatment or therapy to prevent the occurrence of chronic kidney disease or proteinuria comprises a ROBO2 inhibitor.
32. The method of paragraph 30, wherein the ROBO2 inhibitor is a blocking antibody or antigen-binding fragment thereof specific for ROBO2, an antisense molecule specific for ROBO2, a short interfering RNA (siRNA) specific for ROBO2, a small molecule inhibitor of ROBO2, a ROBO2 inhibitory polypeptide, or a ROBO2 structural analog.
33. The method of any one of paragraphs 30-31, wherein the ROBO2 inhibitor blocks or reduces binding of ROBO2 to SLIT, to Nck, or to both.
34. The method of any one of paragraphs 30-32, wherein the ROBO2 inhibitor is specific for the Ig1 SLIT binding domain, the Ig1 and Ig2 SLIT binding domains, the Nck intracellular binding domain, or any combination thereof.
35. The method of paragraph 31, wherein the ROBO2 inhibitory polypeptide is a dominant negative ROBO2 fusion protein, a polypeptide comprising a ROBO2 extracellular domain without the intracellular domain, or a polypeptide comprising a ROBO2 intracellular domain without the extracellular domain.
36. A ROBO2 inhibitor for use in treating a chronic kidney disease.
37. A ROBO2 inhibitor for use in treating proteinuria.
38. The use of any one of paragraphs 35 or 36, wherein the ROBO2 inhibitor is a blocking antibody or antigen-binding fragment thereof specific for ROBO2, an antisense molecule specific for ROBO2, a short interfering RNA (siRNA) specific for ROBO2, a small molecule inhibitor of ROBO2, a ROBO2 inhibitory polypeptide, or a ROBO2 structural analog.
39. The use of any one of paragraphs 35-37, wherein the ROBO2 inhibitor blocks or reduces binding of ROBO2 to SLIT, to Nck, or to both.
40. The use of any one of paragraphs 35-38, wherein the ROBO2 inhibitor is specific for the Ig1 SLIT binding domain, the Ig1 and Ig2 SLIT binding domains, the Nck intracellular binding domain, or any combination thereof.
41. The use of paragraph 37, wherein the ROBO2 inhibitory polypeptide is a dominant negative ROBO2 fusion protein, a polypeptide comprising a ROBO2 extracellular domain without the intracellular domain, or a polypeptide comprising a ROBO2 intracellular domain without the extracellular domain.

42. The use of any one of paragraphs 35-40, wherein the chronic kidney disease or proteinuria is caused by diabetic nephropathy or high blood pressure.

This invention is further illustrated by the following examples which should not be construed as limiting.

EXAMPLES

Tissue In Situ Hybridization, Immunohistochemistry, and Immunogold Electron Microscopy In situ hybridization analysis was performed with digoxigenin-labeled Robo2 riboprobes as previously described (Grieshammer et al., 2004). Immunohistochemistry was performed on mouse embryonic kidney tissues fixed in 4% paraformaldehyde and in adult mouse kidney tissues fixed in methanol. For immunogold electron microscopy, wild-type mouse kidneys were dissected and fixed in paraformaldehyde-lysine-periodate (PLP). Ultrathin sections of the mouse kidney were prepared and incubated with goat anti-Robo2 antibody (DAKO Corporation) and a secondary antibody coupled to 10 nm colloidal gold (Ted Pella).

Yeast Two-Hybrid, Co-Precipitation, and Actin Polymerization Assays

The DUPLEX-A™ yeast two-hybrid system (OriGene Tech) was used to characterize Robo2 and Nck1 interaction according to manufacturer's instructions. Cell culture, His-tagged protein co-precipitation, and immunoprecipitaion were performed as previously reported (Fan et al., 2003). For endogenous immunoprecipitation, mouse newborn kidneys were utilized. CD16 antibody-mediated crosslinking of CD16/7 fusion proteins and the actin polymerization assay were performed as previously described (Jones et al., 2006; Rivera et al., 2004; Verma et al., 2006).

Knockout Mouse Study, Transmission and Scanning Electron Microscopy, and Kidney Glomerular Analysis Mouse protocols were approved by the Institutional Animal Care and Use Committee (IACUC) at Boston University Medical Center (#14388). The generation and genotyping of Robo2$^{flox}$ conditional allele, Robo2$^{del5}$ (also called Robo2$^-$ interchangeably in this paper) germline mutant allele, and Robo2$^+$ wild-type allele were described previously (Lu et al., 2007; Wang et al., 2011). To generate Robo2-nephrin double knockout mice, Robo2$^{+/-}$ mice were crossed with Nphs1$^{+/-}$ mice that were generated previously (Hamano et al., 2002). For transmission electron microscopy, kidneys were fixed, incubated in 2% glutaraldehyde in 0.15 M sodium cacodylate, dehydrated in graded ethanol, embedded in Epon, sectioned, and stained with uranyl acetate and lead citrate. Ultrathin kidney sections were examined using a JEM-1011 electron microscope. For scanning electron microscopy, kidneys were prepared following the standard protocol. For kidney pathological studies, kidneys were fixed in 4% paraformaldehyde, paraffin embedded, sectioned, and stained using standard Periodic acid-Schiff (PAS) or eosin hematoxylin (H&E) methods. For quantification of podocyte number, WT1 was used as a podocyte nuclear marker and immunoperoxidase staining was performed on kidney sections following the standard protocol. WT1 positive podocyte nuclei in each glomerular cross section were counted. For proteinuria analysis, "spot" urine specimens from 6 weeks old mice were examined using a murine albuminuria ELISA quantitation kit (Exocell) according to manufacturer's instruction and urine dipstick (Multistix, Bayer, Ind.) as a screening method.

Tissue In Situ Hybridization and Immunohistochemistry

In situ hybridization analysis was performed with digoxigenin-labeled Robo2 riboprobes as previously described (Grieshammer et al., 2004). The Robo2 cDNA was linearized with NotI and probes were generated using the DIG DNA labeling and detection kit (Roche Applied Science). Hybridization was performed on 4% paraformaldehyde fixed OCT embedded mouse embryonic kidney frozen sections. Immunohistochemistry was performed on mouse embryonic kidney tissues fixed in 4% paraformaldehyde followed by 30% sucrose cryoprotection (Mugford et al., 2008) and in adult mouse kidney tissues fixed in methanol. Mouse kidneys embedded in OCT compound were frozen and sectioned using Cryostat at 8-10 µm. Sections were stained with primary antibodies and followed by an appropriate FITC or Cy3 conjugated secondary antibodies. The primary antibodies used in this study include the ones against ROBO2 (R&D System, Abnova, Santa Cruz Biotechnology), nephrin (custom synthesized) (Topham et al., 1999), Nck (Upstate/Millipore), podocin (Sigma), nidogen (Santa Cruz Biotechnology), Pecam1 (BD Biosciences), WT1 (Santa Cruz Biotechnology), SLIT2 (Santa Cruz Biotechnology), PDGFR beta (Cell Signaling), Synaptopodin (Santa Cruz Biotechnology). Images were obtained using a Perkin Elmer UltraView LCI multi-point spinning disc laser-scanning confocal microscope and a Zeiss LSM 510 confocal laser scanning microscope with a 60× oil immersion objective.

Immunogold Electron Microscopy

Wild-type mouse kidneys were dissected and fixed in paraformaldehyde-lysine-periodate (PLP) at 4° C. overnight. The tissue was washed in 1×PBS and dehydrated in graded ethanol and embedded in LR White resin (Electron Microscopy Sciences). Ultrathin sections of the mouse kidney were prepared and transferred to Formvar-coated gold grids, and blocked with 1% bovine serum albumin and 5% normal goat serum in 1×PBS. The sections were then incubated with goat anti-Robo2 antibody with a 1:50 dilution in DAKO (DAKO Corporation) at 4° C. overnight. Non-immune serum was used as a control. After three washes with 1×PBS, sections were incubated with a IgG secondary antibody coupled to 10 nm colloidal gold (Ted Pella) for 2 hours at room temperature. Sections were finally post-fixed with 1% glutaraldehyde and contrasted with uranyl acetate. Sections were examined with a JEM-1011 transmission electron microscope (JEOL, Tokyo, Japan) at 80 kV, and images were acquired using an AMT digital imaging system (Advanced Microscopy Techniques, Danvers, Mass.) and imported into Adobe Photoshop. Subcellular localization of Robo2 stained with gold particles in glomeruli was recognized on digital electron micrographs in comparison with control micrographs stained with non-immune serum.

Yeast Two-Hybrid Assay

The DUPLEX-A™ yeast two-hybrid system (OriGene Tech, Rockville, Md.) was used to characterize Robo2 and Nck1 interaction. The cDNAs encoding the intracellular domain of human Robo2 and its truncated forms were cloned into the pJG4-5 vector at EcoRI/XhoI sites, fusing them to the transcription activation domain of B42. The cDNAs of human Nck1 and its truncated forms were cloned into the pEG202 vector at EcoRI/XhoI to fuse them to the DNA binding domain of LexA. The lacZ gene in the construct pSH18-34 and the LEU2 gene in the EGY48 strain yeast genome were used as reporter genes. The pEG202, pSH18-34, and pJG4-5 constructs were co-transformed into yeast EGY48 cells. The interaction was considered positive if the yeast cells turned blue in the presence of X-gal and grew in the absence of leucine.

Cell Culture, DNA Constructs, Transfection, Co-Precipitation, and Western Blot Analyses HEK (293T) cells were transfected at 60% confluency using calcium phosphate transfection. To make C-terminal his- and myc-tagged fusion proteins, full-length human nephrin and Robo2 were cloned into pSecTag B vector (Invitrogen) at Hind III/EcoR1 and EcoR1/Xho1 restriction sites respectively. Robo2-ΔNBD was obtained by deleting the Nck binding domain (FIG. 2C) using QUIKCHANGE site-directed mutagenesis kit (Strategene) according to manufacturer's instructions. Non-tagged Robo2 and Nck1 were cloned into pCS2 vector (Addgene) at EcoR1/Xho1 sites, nephrin at HindIII/EcoR1 sites. Human Fyn and myc-tagged Slit2 constructs have been reported previously (Li et al., 2008; Wong et al., 2001). CD16/7-NCD and CD16/7-HA constructs were also reported previously (Verma et al., 2006). To detect Robo2 and Nck1 interaction, C-terminal His- and myc-tagged human Robo2 or Robo2-ΔNBD was expressed in HEK cells. Forty-eight hour post-transfection, cells were lysed in the lysis buffer (50 mM $NaH_2PO_4$, 300 mM NaCl, 10 mM Imidazole, 0.5% TX100, 1× protease inhibitor [pH 8.0]). Cell lysates were centrifuged for 10 min at 4° C.; supernatants were incubated with Ni-NTA resin (Qiagen) at 4° C. for 2 hours to precipitate His-Robo2, NTA resin without Ni was used as a control. The resin was washed three times with washing buffer (50 mM $NaH_2PO_4$, 300 mM NaCl, 20 mM Imidazole, 0.5% TX100 [pH 8.0]) and heated at 95° C. for 10 min. The precipitates were resolved on SDS-PAGE gels and blotted with rabbit anti-myc, rabbit monoclonal anti-Nck1 (Cell Signaling) antibodies at a 1:1000 dilution. To examine the triple interaction among Robo2, Nck1, and nephrin, His-myc-Robo2 or His-myc-Robo2-ΔNBD were co-expressed in HEK cells with human nephrin and human Fyn. His-myc-Robo2 was precipitated with Ni-NTA beads as described above. To confirm the triple interaction, His-myc-nephrin was co-expressed with Robo2, and Fyn in HEK cells and His-myc-nephrin was pulled-down by Ni-NTA beads. Precipitates were blotted with rabbit polyclonal anti-myc, rabbit monoclonal anti-Nck1, rabbit polyclonal anti-nephrin, mouse monoclonal anti-Robo2 (R&D systems), and rabbit polyclonal anti-Fyn (Santa Cruz Biotechnology) antibodies at a 1:1000 dilution. For co-immunoprecipitation of endogenous proteins, kidneys from newborn mice were homogenized in the RIPA buffer (50 mM Tris [pH 7.4], 150 mM NaCl, 0.1% SDS, 1% NP-40, 0.5% sodium deoxycholate, 1 mM $Na_3VO_4$, 1 mM NaF, 1× protease inhibitor) on ice. Samples were centrifuged for 10 min at 4° C. and the supernatant was incubated with 1 μg mouse monoclonal anti-Robo2 antibody (R&D Systems) for 1 hour at 4° C. The control goat IgG (Santa Cruz Biotechnology) was used as a control. Samples were then mixed with 30 μl of protein A/G Plus agarose bead slurry (Santa Cruz Biotechnology) and further incubated for 12 hours at 4° C. Beads were then washed three times in the RIPA buffer and proteins were eluted in 1× protein loading buffer by heating at 95° C. for 10 min. Precipitates were resolved on SDS-PAGE gels and blotted with mouse anti-Robo2, rabbit anti-nephrin, and rabbit anti-Nck1 antibodies as described above. Actin was blotted with anti-beta-actin mouse antibody from Sigma. Intensity of the bands was measured using ImageJ. For proteinuria detection, mice spot urines were collected and diluted with 1× protein loading buffer at 1:100 dilution. Urine proteins were then resolved on SDS-PAGE gels and purified albumin was used as a control (MP Biomedicals). Gels were blotted with rabbit anti-albumin polyclonal antibody (MP Biomedicals).

CD16/7-NCD Crosslinking and Actin Polymerization Assay

CD16 antibody-mediated crosslinking of CD16/7 fusion proteins has been described previously (Jones et al., 2006; Rivera et al., 2004; Verma et al., 2006). Briefly, CD16/7-NCD or CD16/7-HA was co-expressed in HEK cells with Robo2. After 24 hours, cells were transferred and seeded on glass coverslips coated with polylysine for another 24 hours. Cells were then incubated with 1 μg/ml mouse monoclonal anti-CD16 (Beckman Coulter) for 30 min at 37° C., washed once with DMEM, incubated with rhodamine-conjugated secondary antibody (Thermo Scientific) diluted in Slit2 conditioned medium (Wong et al., 2001) or control conditioned medium for 30 min and fixed in 4% paraformaldehyde in 1×PBS. F-actin was stained using FITC-conjugated phalloidin (Invitrogen) according to manufacturer's instruction. The newly formed F-actin bundles stick to the clustered nephrin (CD16/7-NCD) and look like comet tails (i.e. actin tails in the main text) under fluorescence microscope. In this experiment, we only analyzed the F-actin bundles formed by clustering of CD16/7-NCD and attached to the clusters. The cells with F-actin tails were counted and compared to the total CD16/7-NCD transfected cells. The quantification formula is: Percentage %=(number of transfected cells with F-actin tails/total number of cells transfected)×100. Images were obtained using a LSM510 confocal microscope with a 60× oil immersion objective.

Generation and Characterization of Robo2 Podocyte Specific Knockout Mice and Robo2-Nephrin Double Knockout Mice The generation and genotyping of $Robo2^{flox}$ conditional allele, $Robo2^{del5}$ (also called $Robo2^-$ interchangeably in this paper) germline mutant allele, and $Robo2^+$ wild-type allele were described previously (Lu et al., 2007; Wang et al., 2011). Standard breeding scheme was followed to generate Robo2 podocyte specific $Robo2^{del5/flox}$; $Tg^{Nphs2-Cre/+}$ knockout mice, which carry one $Robo2^{del5}$ allele and one $Robo2^{flox}$ allele. In this compound mutant, podocyte specific Cre recombinase driven by podocin promoter deletes only the $Robo2^{flox}$ allele to facilitate the penetrance of a phenotype because the other allele, $Robo2^{del5}$, has been deleted ubiquitously from germline expression. The authenticity of $Robo2^{del5/flox}$; $Tg^{Nphs2-Cre/+}$ mice was determined by tail DNA genotyping for the presence of $Robo2^{del5}$ and $Robo2^{flox}$ alleles as well as $Tg^{Nphs2-Cre}$ transgene. F2 littermates $Robo2^{flox/+}$ mice without $Robo2^{del5}$ allele and $Tg^{Nphs2-Cre}$ transgene were used as controls. To generate Robo2-nephrin double knockout mice, $Robo2^{+/-}$ heterozygous mice were crossed with $Nphs1^{+/-}$ heterozygous mice that were generated previously (Hamano et al., 2002). After the generation of $Robo2^{+/-}$; $Nphs1^{+/-}$ double heterozygous mice, the cross of double heterozygous mice was performed to generate $Robo2^{-/-}$; $Nphs1^{-/-}$ double homozygous mice as well as $Nphs1^{-/-}$ single homozygous, $Robo2^{-/-}$ single homozygous, and $Robo2^{+/+}$; $Nphs1^{+/+}$ wild-type controls. Mouse protocols were approved by the Institutional Animal Care and Use Committee (IACUC) at Boston University Medical Center (#14388).

Transmission and Scanning Electron Microscopy

For transmission electron microscopy, kidneys were dissected from Robo2 homozygous null mice and podocyte specific knockout mice, fixed in PLP at 4° C. overnight, and then incubated in 2% glutaraldehyde in 0.15 M sodium cacodylate for 6 hours. After washing in 1×PBS, fixed kidneys were dehydrated in graded ethanol, embedded in Epon, sectioned, and stained with uranyl acetate and lead citrate. Ultrathin kidney sections were prepared and examined using a JEM-1011 electron microscope. Wild-type littermates were used as controls. For scanning electron microscopy, kidney samples from Robo2 homozygous null mice, podocyte specific knockout mice, nephrin homozygous null mice, and Robo2-nephrin double homozygous mice were prepared following the protocol described previously (Friedman and Ellisman, 1981) with minor modifications. Briefly, the kidney was perfused with 2.5% glutaraldehyde and 2% paraformaldehyde solution in 0.1M cacodylate buffer (Karnovsky's fixative, Electron Microscopy Sciences), and subsequently fixed in the Karnovsky's fixative for 24 hrs followed by postfixation in 2% osmium tetraoxide solution (Electron Microscopy Sciences). Kidney samples were cryofractured, dehydrated and dried using hexamethyldisilazane (Electron Microscopy Sciences). Kidney samples were imaged using an Amray 1000A and Jeol 6340F scanning electron microscopes. Three glomeruli from each animal were examined to provide representative images.

Mice Kidney Pathology Studies, Quantification of Podocyte Number, and Proteinuria Analysis For kidney pathological studies, kidneys were dissected and fixed in 4% paraformaldehyde overnight, and then treated with a graded ethanol series for paraffin embedding. The kidney paraffin blocks were sectioned at 4 µm using a MT-920 microtome (MICROM) and stained using standard Periodic acid-Schiff (PAS) or eosin hematoxylin (H&E) methods. The glomeruli were examined and assessed for matrix deposition, segmental glomerulosclerosis, and dilatations of the Bowman's space using an Olympus BHT light microscope equipped with a SPOT digital camera system. For quantification of podocyte number, WT1 was used as a podocyte nuclear marker and immunoperoxidase staining was performed on kidney sections following the protocol described previously (Sanden et al., 2003). Briefly, paraffin embedded kidney sections from 4 one-year old $Robo2^{del5/flox}$; $Tg^{Nphs2-Cre+}$ podocyte-specific knockout mice and 4 age-matched wild-type control mice were sectioned at 4 µm and stained with WT1 antibody (Santa Cruz Biotechnology) after microwave antigen retrieval. Biotinylated secondary antibody and Vectastain ABC kit (Vector Laboratories) were used to detect WT1 signal. WT1 positive podocyte nuclei in each glomerular cross section were counted in total 165 glomeruli from four mutant mice and 166 glomeruli from four control mice. For proteinuria analysis, "spot" urine specimens from 6 weeks old mice were examined using a sensitive murine albuminuria ELISA quantitation kit (Exocell) according to manufacturer's instruction and urine dipstick (Multistix from Bayer, Ind.) as a screening method. Urine albumin was normalized with creatinine to provide an albumin/creatinine ratio. Creatinine in urine was determined using the creatinine detection kit (Sigma) according to manufacturer's instruction. Urine albumin was also examined by 12% SDS-PAGE and blotted with anti-albumin antibody (MP Biomedicals). The data from mutants and controls were analyzed using one-way ANOVA, Student t-test, and Chi-square test.

TABLE 1

Quantitative Analysis of Glomeruli with Increased Matrix Expansion in 2 to 9 Months Old Robo2 Podocyte Specific Knockout Mice (Mutant) Compared to Controls (Wild type)

| Genotype | Mouse ID# | Age (months) | Total glomeruli counted | Glomeruli with mesangial matrix expansion | % of Glomeruli with mesangial matrix expansion* |
|---|---|---|---|---|---|
| Mutant | 4048 | 2 | 96 | 13 | 12.35% |
| Mutant | 1721 | 3 | 107 | 18 | 16.82% |
| Mutant | 4005 | 6 | 103 | 17 | 16.51% |
| Mutant | 1190 | 7 | 102 | 20 | 19.61% |
| Mutant | 2396 | 9 | 80 | 14 | 17.50% |
| Mutant total | | | 488 | 82 | 16.80% |
| Wild type | 4058 | 2 | 90 | 4 | 4.44% |
| Wild type | 4052 | 3 | 105 | 6 | 5.71% |
| Wild type | 3919 | 6 | 107 | 4 | 3.74% |
| Wild type | 1191 | 7 | 103 | 5 | 4.85% |
| Wild type | 2385 | 9 | 106 | 5 | 4.72% |
| Wild type total | | | 511 | 24 | 4.70% |

*$p < 0.01$, n = 5, t-test.

TABLE 2

Quantitative Analysis of Glomeruli with Increased Matrix Expansion in 12-months-old Robo2 Podocyte-Specific Knockout Mice (Mutant) Compared to Controls (Wild type)

| Genotype | Mouse ID# | Age (months) | Total glomeruli counted | Glomeruli with mesangial matrix expansion | % of Glomeruli with mesangial matrix expansion* |
|---|---|---|---|---|---|
| Mutant | 1844 | 12 | 136 | 17 | 12.50% |
| Mutant | 1847 | 12 | 125 | 18 | 14.40% |
| Mutant | 1877 | 12 | 127 | 11 | 8.66% |
| Mutant | 1878 | 12 | 132 | 20 | 15.15% |
| Mutant | 1948 | 12 | 142 | 28 | 19.72% |
| Mutant total | | | 662 | 94 | 14.20% |
| Wild type | 1901 | 12 | 125 | 5 | 4.00% |
| Wild type | 2429 | 12 | 179 | 8 | 4.47% |
| Wild type | 2834 | 12 | 154 | 9 | 5.84% |
| Wild type | 2836 | 12 | 159 | 7 | 4.40% |
| Wild type | 2837 | 12 | 124 | 5 | 4.03% |
| Wild type total | | | 741 | 34 | 4.59% |

*$p < 0.01$, n = 5, t-test.

TABLE 3

Morphology Analysis of Glomeruli with Dilated Bowman's Space in $Nphs1^{-/-}$ Single-Homozygous ($Robo2^{+/-}$; $Nphs1^{-/-}$) Compared to $Robo2^{-/-}$; $Nphs1^{-/-}$ Double-Homozygous Newborn Mice by Histology

| Genotype | Total glomeruli counted | Glomeruli with dilated Bowman's space | % of Glomeruli with dilated Bowman's space |
|---|---|---|---|
| $Robo2^{+/-}$; $Nphs1^{-/-}$ | 122 | 31 | 25.4% |
| $Robo2^{-/-}$; $Nphs1^{-/-}$ | 55 | 2 | 3.6% |

TABLE 3-continued

Morphology Analysis of Glomeruli with Dilated Bowman's Space in Nphs1$^{-/-}$ Single-Homozygous (Robo2$^{+/-}$; Nphs1$^{-/-}$) Compared to Robo2$^{-/-}$; Nphs1$^{-/-}$ Double-Homozygous Newborn Mice by Histology

| Genotype | Total glomeruli counted | Glomeruli with dilated Bowman's space | % of Glomeruli with dilated Bowman's space |
|---|---|---|---|
| Robo2$^{-/-}$; Nphs1$^{+/-}$ | 158 | 3 | 1.9% |
| Robo2$^{+/+}$; Nphs1$^{+/+}$ | 271 | 1 | 0.4% |

Note:
The glomerulus was scored as positive with dilated Bowman's space if the glomerulus displayed similar phenotype as shown in FIG. S4U was observed, and was scored as negative if similar glomerulus as shown in FIG. 8V-8X was observed. Three mice from each genotype were analyzed. Robo2$^{-/-}$ single homozygous (Robo2$^{-/-}$; Nphs1$^{+/-}$) and wild-type (Robo2$^{+/+}$; Nphs1$^{+/+}$) were used as controls.

TABLE 4

Morphology Analysis of Glomerular Podocyte Interdigitating Foot Process (FP) Phenotype in Nphs1$^{-/-}$ Single-Homozygous (Robo2$^{+/-}$; Nphs1$^{-/-}$) Compared to Robo2$^{-/-}$; Nphs1$^{-/-}$ Double-Homozygous Newborn Mice by Scanning Electron Microscopy

| Genotype | Total glomeruli counted | Glomeruli with interdigitating FP structure | % of Glomeruli with interdigitating FP structure |
|---|---|---|---|
| Robo2$^{+/-}$; Nphs1$^{-/-}$ | 15 | 1 | 6.67% |
| Robo2$^{-/-}$; Nphs1$^{-/-}$ | 16 | 12 | 75% |
| Robo2$^{-/-}$; Nphs1$^{+/-}$ | 13 | 13 | 100% |
| Robo2$^{+/+}$; Nphs1$^{+/+}$ | 13 | 13 | 100% |

REFERENCES

Bashaw, G. J., Kidd, T., Murray, D., Pawson, T., and Goodman, C. S. (2000). Repulsive axon guidance: Abelson and Enabled play opposing roles downstream of the roundabout receptor. Cell 101, 703-715.

Dickson, B. J., and Gilestro, G. F. (2006). Regulation of commissural axon pathfinding by slit and its Robo receptors. Annu Rev Cell Dev Biol 22, 651-675.

Done, S. C., Takemoto, M., He, L., Sun, Y., Hultenby, K., Betsholtz, C., and Tryggvason, K. (2008). Nephrin is involved in podocyte maturation but not survival during glomerular development. Kidney Int 73, 697-704.

Fan, X., Labrador, J. P., Hing, H., and Bashaw, G. J. (2003). Slit stimulation recruits Dock and Pak to the roundabout receptor and increases Rac activity to regulate axon repulsion at the CNS midline. Neuron 40, 113-127.

Faul, C., Asanuma, K., Yanagida-Asanuma, E., Kim, K., and Mundel, P. (2007). Actin up: regulation of podocyte structure and function by components of the actin cytoskeleton. Trends Cell Biol 17, 428-437.

Furness, P. N., Hall, L. L., Shaw, J. A., and Pringle, J. H. (1999). Glomerular expression of nephrin is decreased in acquired human nephrotic syndrome. Nephrol Dial Transplant 14, 1234-1237.

Garg, P., Verma, R., Cook, L., Soofi, A., Venkatareddy, M., George, B., Mizuno, K., Gurniak, C., Witke, W., and Holzman, L. B. (2010). Actin-depolymerizing factor cofilin-1 is necessary in maintaining mature podocyte architecture. J Biol Chem 285, 22676-22688.

Grieshammer, U., Le, M., Plump, A. S., Wang, F., Tessier-Lavigne, M., and Martin, G. R. (2004). SLIT2-mediated ROBO2 signaling restricts kidney induction to a single site. Dev Cell 6, 709-717.

Guan, K. L., and Rao, Y. (2003). Signalling mechanisms mediating neuronal responses to guidance cues. Nat Rev Neurosci 4, 941-956.

Hamano, Y., Grunkemeyer, J. A., Sudhakar, A., Zeisberg, M., Cosgrove, D., Morello, R., Lee, B., Sugimoto, H., and Kalluri, R. (2002). Determinants of vascular permeability in the kidney glomerulus. J Biol Chem 277, 31154-31162.

Jones, N., Blasutig, I. M., Eremina, V., Ruston, J. M., Bladt, F., Li, H., Huang, H., Larose, L., Li, S. S., Takano, T., et al. (2006). Nck adaptor proteins link nephrin to the actin cytoskeleton of kidney podocytes. Nature 440, 818-823.

Lu, W., van Eerde, A. M., Fan, X., Quintero-Rivera, F., Kulkarni, S., Ferguson, H. L., Kim, H., Fan, Y., Xi, Q., Li, Q. G., et al. (2007). Disruption of ROBO2 is associated with urinary tract anomalies and confers risk of vesicoureteral reflux. Am J Hum Genet 80, 616-632.

Nachman, P. H., Jennette, J. C., and Falk, R. J. (2008). Primary glomerular disease. In Brenner & Rector's The Kidney, B. M. Brenner, ed. (Pheladelphia, Saunders), pp. 987-1066.

Patrakka, J., Ruotsalainen, V., Reponen, P., Qvist, E., Laine, J., Holmberg, C., Tryggvason, K., and Jalanko, H. (2002). Recurrence of nephrotic syndrome in kidney grafts of patients with congenital nephrotic syndrome of the Finnish type: role of nephrin. Transplantation 73, 394-403.

Piper, M., Anderson, R., Dwivedy, A., Weinl, C., van Horck, F., Leung, K. M., Cogill, E., and Holt, C. (2006). Signaling mechanisms underlying Slit2-induced collapse of Xenopus retinal growth cones. Neuron 49, 215-228.

Piper, M., Georgas, K., Yamada, T., and Little, M. (2000). Expression of the vertebrate Slit gene family and their putative receptors, the Robo genes, in the developing murine kidney. Mech Dev 94, 213-217.

Reeves, W., Caulfield, J. P., and Farquhar, M. G. (1978). Differentiation of epithelial foot processes and filtration slits: sequential appearance of occluding junctions, epithelial polyanion, and slit membranes in developing glomeruli. Lab Invest 39, 90-100.

Rivera, G. M., Briceno, C. A., Takeshima, F., Snapper, S. B., and Mayer, B. J. (2004). Inducible clustering of membrane-targeted SH3 domains of the adaptor protein Nck triggers localized actin polymerization. Curr Biol 14, 11-22.

Seiler, M. W., Venkatachalam, M. A., and Cotran, R. S. (1975). Glomerular epithelium: structural alterations induced by polycations. Science 189, 390-393.

Shih, N. Y., Li, J., Cotran, R., Mundel, P., Miner, J. H., and Shaw, A. S. (2001). CD2AP localizes to the slit diaphragm and binds to nephrin via a novel C-terminal domain. Am J Pathol 159, 2303-2308.

Topham, P. S., Kawachi, H., Haydar, S. A., Chugh, S., Addona, T. A., Charron, K. B., Holzman, L. B., Shia, M., Shimizu, F., and Salant, D. J. (1999). Nephritogenic mAb 5-1-6 is directed at the extracellular domain of rat nephrin. J Clin Invest 104, 1559-1566.

Tryggvason, K., Patrakka, J., and Wartiovaara, J. (2006). Hereditary proteinuria syndromes and mechanisms of proteinuria. N Engl J Med 354, 1387-1401.

Verma, R., Kovari, I., Soofi, A., Nihalani, D., Patrie, K., and Holzman, L. B. (2006). Nephrin ectodomain engagement results in Src kinase activation, nephrin phosphorylation, Nck recruitment, and actin polymerization. J Clin Invest 116, 1346-1359.

Wang, H., Li, Q., Liu, J., Mendelsohn, C., Salant, D. J., and Lu, W. (2011). Noninvasive assessment of antenatal hydronephrosis in mice reveals a critical role for Robo2 in maintaining anti-reflux mechanism. PLoS One 6, e24763.

Wong, K., Ren, X. R., Huang, Y. Z., Xie, Y., Liu, G., Saito, H., Tang, H., Wen, L., Brady-Kalnay, S. M., Mei, L., et al. (2001). Signal transduction in neuronal migration: roles of GTPase activating proteins and the small GTPase Cdc42 in the Slit-Robo pathway. Cell 107, 209-221.

Yuan, H., Takeuchi, E., and Salant, D. J. (2002). Podocyte slit-diaphragm protein nephrin is linked to the actin cytoskeleton. Am J Physiol Renal Physiol 282, F585-591.

Friedman, P. L., and Ellisman, M. H. (1981). Enhanced visualization of peripheral nerve and sensory receptors in the scanning electron microscope using cryofracture and osmium-thiocarbohydrazide-osmium impregnation. J Neurocytol 10, 111-131.

Li, X., Gao, X., Liu, G., Xiong, W., Wu, J., and Rao, Y. (2008). Netrin signal transduction and the guanine nucleotide exchange factor DOCK180 in attractive signaling. Nat Neurosci 11, 28-35.

Mugford, J. W., Sipila, P., Kobayashi, A., Behringer, R. R., and McMahon, A. P. (2008). Hoxd11 specifies a program of metanephric kidney development within the intermediate mesoderm of the mouse embryo. Dev Biol 319, 396-405.

Sanden, S. K., Wiggins, J. E., Goyal, M., Riggs, L. K., and Wiggins, R. C. (2003). Evaluation of a thick and thin section method for estimation of podocyte number, glomerular volume, and glomerular volume per podocyte in rat kidney with Wilms' tumor-1 protein used as a podocyte nuclear marker. J Am Soc Nephrol 14, 2484-2493.

We claim:

1. A pharmaceutical composition comprising a Roundabout 2 (ROBO2) inhibitor that inhibits ROBO2 biological activity, wherein the ROBO2 inhibitor is a soluble ROBO2 protein that (i) comprises immunoglobulin (Ig) motifs 1 and 2 of said ROBO2, (ii) does not comprise Ig motifs 3, 4, and 5 of said ROBO2, and (iii) does not comprise fibronectin type III (FNIII) repeats of said ROBO2; and a pharmaceutically acceptable carrier.

2. The pharmaceutical composition of claim 1, wherein the ROBO2 inhibitor prevents or reduces binding of the ROBO2 to SLIT2, to Nck, or to both.

3. The pharmaceutical composition of claim 1, wherein said soluble ROBO2 protein binds to SLIT with a binding affinity $K_D$ (dissociation constant) value of $10^{-8}$ M or less.

4. The pharmaceutical composition of claim 1, wherein the ROBO2 inhibitor is a dominant negative soluble ROBO2 protein that reduces the binding of ROBO2 to SLIT by at least 30%, relative to binding of ROBO2 to SLIT in the absence of said soluble ROBO2 protein.

5. The pharmaceutical composition of claim 4, wherein the ROBO2 inhibitor is a fusion polypeptide comprising the dominant negative soluble ROBO2 protein.

6. The pharmaceutical composition of claim 1, wherein the soluble ROBO2 protein comprises amino acid residues 30-129 and 135-221 of SEQ ID NO: 3.

7. The pharmaceutical composition of claim 1, wherein said soluble ROBO2 protein does not comprise the intracellular domain of said ROBO2.

8. The pharmaceutical composition of claim 7, wherein said intracellular domain comprises amino acid residues 881-1378 of SEQ ID NO: 3.

9. The pharmaceutical composition of claim 1, wherein said Ig motif 1 comprises amino acid residues 30-129 of SEQ ID NO: 3.

10. The pharmaceutical composition of claim 1, wherein said Ig motif 2 comprises amino acid residues 135-221 of SEQ ID NO: 3.

11. The pharmaceutical composition of claim 1, wherein said Ig motif 1 comprises amino acid residues 30-129 of SEQ ID NO: 3, and said Ig motif 2 comprises amino acid residues 135-221 of SEQ ID NO: 3.

* * * * *